(12) United States Patent
Hatzfeld et al.

(10) Patent No.: US 7,427,676 B2
(45) Date of Patent: Sep. 23, 2008

(54) RICE PROMOTERS

(75) Inventors: Yves Hatzfeld, Lille (FR); Willem Broekaert, Dilbeek (BE)

(73) Assignee: Crop Design N.V., Ghent (BE)

( * ) Notice: Subject to any disclaimer, the term of this patent is extended or adjusted under 35 U.S.C. 154(b) by 79 days.

(21) Appl. No.: 10/525,647

(22) PCT Filed: Feb. 4, 2004

(86) PCT No.: PCT/EP2004/050081

§ 371 (c)(1),
(2), (4) Date: Feb. 24, 2005

(87) PCT Pub. No.: WO2004/070039

PCT Pub. Date: Aug. 19, 2004

(65) Prior Publication Data

US 2006/0112442 A1    May 25, 2006

(30) Foreign Application Priority Data

Feb. 4, 2003   (EP) ................................. 03075331

(51) Int. Cl.
*C12N 15/63* (2006.01)
*C12N 15/82* (2006.01)
*C12N 5/04* (2006.01)

(52) U.S. Cl. .................. 536/24.1; 435/320.1; 435/419; 435/468

(58) Field of Classification Search ....................... None
See application file for complete search history.

(56) References Cited

U.S. PATENT DOCUMENTS

2004/0016025 A1   1/2004  Budworth et al.

FOREIGN PATENT DOCUMENTS

WO    WO 00/70067     11/2000
WO    WO 03/000898 A1   1/2003

OTHER PUBLICATIONS

Evans et al. 1992, Plant Mol. Biol. 20:1019-1028.*
Sasaki et al. 2001, Genbank accession:AP004004.*
Wu et al. 2002, Genbank accession:AF541859.*
Padgette et al 1995, Crop Sci. 35:1451-1461.*
An et al 1986, Plant Physiol. 81:301-305.*
Evans et al 1992, Plant Mol. Biol. 20:1019-1028.*
Kim et al. 1994, Plant Molecular Biology 24: 105-117.*
Fourgoux-Nicol et al. 1999, Plant Molecular Biology 40 :857-872.*
Jang et al., High-Level and Ubiquitous Expression of the Rice Cytochrome c Gene OsCc1 and Its Promoter Activity in Transgenic Plants Provides a Useful Promoter for Transgenesis of Monocots[1] Plant Physiology, Aug. 2002.
Vibok et al., Endosperm specific expression of a gliadin-actin hybrid promoter in transgenic rice (Orysa sativa L.) Cereal Reserch Communications, vol. 27, No. 3, 1999.
Xu et al., Characterization of a rice gene family encoding root-specific proteins, Plant Molecular Biology 27, pp. 237-248, 1995.
Rice HMGB1 protein recognizes DNA structures and bends DNA Efficiently, Wu et al., Elsevier Scince, Archives of Biochemstry and Physics 411 (2003) 105-111.

* cited by examiner

*Primary Examiner*—Ashwin Mehta
*Assistant Examiner*—Li Zheng
(74) *Attorney, Agent, or Firm*—Barbara E. Johnson, Esq.

(57) ABSTRACT

The invention provides several promoters isolated from *Oryza sativa*, which promoters are capable of driving and/or regulating the expression of an operably linked nucleic acid in a plant. The expression patterns of the promoters according to the invention have been studied in *Oryza sativa* and some of the promoters displayed specific activity in particular cells, tissues or organs of the plant, while others displayed constitutive expression throughout substantially the whole plant. Some promoters showed weak expression, while others were strongly active.

19 Claims, 11 Drawing Sheets

PRO0110 RCc3

PRO0005 putative beta-amylase

PRO0009 putative cellulose synthase

PRO058 proteinase inhibitor Rgpi9

PRO061 beta-expansin EXPB9

PRO0063 structural protein

PRO0081 putative caffeoyl CoA 3-O-methyltransferase

PRO0091 prolamin RP5

PRO0095 putative methionine aminopeptidase

PRO0111 uclacyanin 3-like protein

PRO0116 26S proteasome regulatory particle non-ATPase subunit 11

PRO0117 putative 40S ribosomal protein

PRO0122 chlorophyll a/b binding protein precursor (Cab27)

PRO0123 putative protochlorophyllide reductase

PRO0133 chitinase Cht-3

PRO0151 WSI18

PRO0169 aquaporine

PRO0170 high mobility group protein

PRO0171 reversibly glycosylated protein RGP1

PRO0173 cytosolic MDH

PRO0175 RAB21

PRO0177 Cdc2-1

SEQUENCE LISTING

```
<160> NUMBER OF SEQ ID NOS: 88

<210> SEQ ID NO 1
<211> LENGTH: 1264
<212> TYPE: DNA
<213> ORGANISM: Oryza sativa
<220> FEATURE:
<221> NAME/KEY: misc_feature
<223> OTHER INFORMATION: PRO0110 - RCc3

<400> SEQUENCE: 1
tcgacgctac tcaagtggtg ggaggccacc gcatgttcca acgaagcgcc aaagaaagcc      60
ttgcagactc taatgctatt agtcgcctag gatatttgga atgaaaggaa ccgcagagtt     120
tttcagcacc aagagcttcc ggtggctagt ctgatagcca aaattaagga ggatgccaaa     180
acatgggtct tggcgggcgc gaaacacctt gataggtggc ttaccttta acatgttcgg      240 gccaaaggcc ttgagacggt aaagttttct atttgcgctt gcgcatgtac aattttattc     300
ctctattcaa tgaaattggt ggctcactgg ttcattaaaa aaaaagaat ctagcctgtt      360 cgggaagaag aggattttgt tcgtgagaga gagagagaga gagagagaga gagagagaga     420
gaaggaggag gaggattttc aggcttcgca ttgcccaacc tctgcttctg ttggcccaag     480
aagaatccca ggcgcccatg ggctggcagt ttaccacgga cctacctagc ctaccttagc     540
tatctaagcg ggccgaccta gtagccacgt gcctagtgta gattaaagtt gccgggccag     600
caggaagcca cgctgcaatg gcatcttccc ctgtccttcg cgtacgtgaa aacaaaccca     660
ggtaagctta gaatcttctt gcccgttgga ctgggacacc caccaatccc accatgcccc     720
gatattcctc cggtctcggt tcatgtgatg tcctctcttg tgtgatcacg gagcaagcat     780
tcttaaacgg caaaagaaaa tcaccaactt gctcacgcag tcacgctgca ccgcgcgaag     840
cgacgcccga taggccaaga tcgcgagata aaataacaac caatgatcat aaggaaacaa     900
gcccgcgatg tgtcgtgtgc agcaatcttg gtcatttgcg ggatcgagtg cttcacagct     960
aaccaaatat tcggccgatg atttaacaca ttatcagcgt agatgtacgt acgatttgtt    1020
aattaatcta cgagccttgc tagggcaggt gttctgccag ccaatccaga tcgccctcgt    1080
atgcacgctc acatgatggc agggcagggt tcacatgagc tctaacggtc gattaattaa    1140
tcccggggct cgactataaa tacctcccta atcccatgat caaaaccatc tcaagcagcc    1200
taatcatctc cagctgatca agagctctta attagctagc tagtgattag ctgcgcttgt    1260
gatc                                                                1264

<210> SEQ ID NO 2
<211> LENGTH: 1215
<212> TYPE: DNA
<213> ORGANISM: Oryza sativa
<220> FEATURE:
<221> NAME/KEY: misc_feature
<223> OTHER INFORMATION: PRO0005 - putative beta-amylase
```

-continued

```
<400> SEQUENCE: 2
cccgatttag tagaccacat tttggcatca aaccaaaata gaccctctcc cagaatttgt      60
aaatggcttt gtggttcgtg atatcactga acctgctggg tgaataaagt aaaaaaaaaa     120
acccataaat tggccttctg caagatctcg tcgtcttgcc caaactatag ccttcgatct     180
ttccatcagg accgcatggg gggagagcag gggcaagtat gaaatggagt tcagattcag     240
attctagaac agtctgaaca tgcgacgacg acgatggcga tgtatctgaa caatctggtc     300 ctctcccctct cctcccgggc gggcttccac gcggctgagt ttcaggctcc aatctgcag     360 ctcctcccag aaccttactc tgattgattg gttcatcgtt tccatggctc caatgaatgc     420
aacgtgttgt tcagattttc tgaatcttgt tctcaatccg gagtacgtgc tgtagcagca     480 gcaatcgtgtc cctgatctga aatttttaga cactcgtaga ttcgctgatc aatcattccg     540
tcccttcgag tggtctagat tgagcttaat catcctgcta ctcgaatcaa atcttcagca     600
agtgagagct agataattca aagaaatca acatattctt cgcgaaaaaa agaaataacc      660
gatgaaacca cggtaattag gttcttcgaa tcaccgggag agtaggaaaa acgagctaa     720 aatcccacat aggaggaaac ggttaaaaac ggccactccg cgtctccgcc gcgagactag     780
ctctcgccag tccacgtagc ccaatccaca accgccacgt gctccgacaa tcccgcccgt     840
ccatcgccgc ggccccggcc tcatctcgac cactcgtttc ctcccttcac accagccacg     900
tggcactctc tcgagagctc ccgcccgcct atataaactt gttcgcgctc ggctcctcct     960
cctcatcgac ctccaccccca cattgaataa ttatttttaa taattttagt tttttttttg    1020
gctttagata tattcccaat ccccaacctc ccaataatcc gatctctccc agttctgttc    1080
ggatcaaggc tgtgtcgatc gcaaaaaaga aaaaaaaac aatttccttt tggggtggtt    1140
catctgttga tcacttcttt gtttcccgcg ttttgttggg gattcgattt tcgggttaag   1200
attttctaca cgacc                                                    1215

<210> SEQ ID NO 3
<211> LENGTH: 1038
<212> TYPE: DNA
<213> ORGANISM: Oryza sativa
<220> FEATURE:
<221> NAME/KEY: misc_feature
<223> OTHER INFORMATION: PRO0009 - putative cellulose synthase

<400> SEQUENCE: 3
gccatcgagt ggtgtgccga taccggcgcc tgttctttac agcctcagct agtgttgttg      60
tccgaggcaa tttttccgac ctattgtgtt gctttcctct ctgatagctt atggtaaaag     120
atacaaagat gttgaggagt ttgtacgcca cttaattttg ctcgtaacat acattgacaa     180
tcaagaggag ccatggcatt gcgatctgct tacacggcat attcttactg gatggtgtac     240
actacttacc cttttaatg caagcatcaa tccattgctt ttctcactgc acacctgatt     300
cgtactgaaa acgtgaaaca taaaaaaaaa acaaaaatct agctgatgtt ggctctcggg     360
gcctcgagtc tagtttgtcc tagatggcta acctgatatg tgttggtcac gctcacgttt     420
gaaccgagaa agagtgtgtg tgtgtgtgtg tcggcgtgct gctacaccag agcctccctg     480
aatcgcaatg cgtgttaacg ccagcatcgc aggatttcat ctcacttgac aggttcagat     540
ggccttcctc ctaccgtctg ccatttatac acgcagtgac ttaacgctta cacgagccgg     600
atggcccgga tctcccccct gcaccatctc accagaaaaa cggtgaggcg tcaccgcaac     660 ccaccccacca aacacatcca cgtcccttca ccgttggcct tcgattttgc ttcagctgca    720
```

-continued

| | |
|---|---|
| ctacgacccc tccaacacat ttccctcgcg tctcgttgcg atctcacctt acgacgatct | 780 |
| cgttccagca gcagcagcat cggcagcggc ggcttgcttc cgaagcgagc aatgcatggc | 840 |
| gcgcgcggcc gcgtgcgtgc gtgccttggc ttgcgctcta atcaaaccgg dacgccccaa | 900 |
| ctcacggttg gtgcgggacg ccaccccgcc accttaccgc ccccgcctcc ctgcatctga | 960 |
| tcatcaacca gctgctatat cacctagcta gccgccgcct cctcctcgcc caccaacgtc | 1020 |
| gcttccccgg cacctcac | 1038 |

<210> SEQ ID NO 4
<211> LENGTH: 1301
<212> TYPE: DNA
<213> ORGANISM: Oryza sativa
<220> FEATURE:
<221> NAME/KEY: misc_feature
<223> OTHER INFORMATION: PRO0058 - proteinase inhibitor Rgpi9

<400> SEQUENCE: 4

| | |
|---|---|
| tctcttctga agctgaagcc ctgcgaaata ggcctttaaa cgctttaagg ttactggatg | 60 |
| atcatatcgg cgtaagaccg gtttaaacat ggtttcgctt tgtgaatcca atgtgagtca | 120 |
| cgacgtgaca catggcacgt ccttggagct ttagacatat cgaatctgag cactggagtg | 180 |
| gccgagtggg tgagcggcca aatccgtttt agacagatcg cactgacacg atgttgatca | 240 |
| ttgatactaa taccattta tcaagcagta gtgttgaaaa aaaaactat gttctcttca | 300 |
| actgtgagat ttcatcccgt ttcaagatga acaagccatg catgtgagat gtgaacagaa | 360 |
| ggcagaagac agtggaaaga caggacaaat aagtgaagag ggatcaaatc aatgggcctg | 420 |
| acggtttctg aaagttgaca tggaaatcgc cggtgatcac cggtttatac gttatttaaa | 480 |
| tctgcgattt ccactttcgt ttgctttcgg ggttccaatt tgagtcacgc acatattctt | 540 |
| catcgtgctt tggatctcag caccgtagta acttttggac aaattgcatt cgccgacact | 600 |
| aataacatgt tcttttatg ctgctttaca tatactgctt atccacaccc aatcccatgt | 660 |
| tcatatatta tgagatggag ggagtaaact ttgttaacag caacattttt tatattaaag | 720 |
| catcaactaa ttaaagcaca agatacgcat gttatctcaa taaatcttcc agtgcatgta | 780 |
| taaagaagat gtcgccgcta acttagataa ttttttgtgac ttttatcctg gccggcataa | 840 |
| ttaattcttc cggaaattaa aagctagttt ttccatattc atcagtacag acaagacagc | 900 |
| atagtaagcg aagcatacct gacgtgttag ctcattgtaa ctcgatctgg aacactcgat | 960 |
| gctagataca gacagacact cctcgtgatg aacgttagca tttagcaaca tacggtgata | 1020 |
| aagcagctgg ggatcgatcc atccatccat cgtctttaca cgtacttacc ttgctaaccg | 1080 |
| cactgtcgac tcttgcatgt ttgcatgtaa tccaaatgga ccccacgtgg aacatgctca | 1140 |
| cagtgctttg cagctgcttt ccaaaatgct ttctttcact tcttccattc ctctgtccac | 1200 |
| aaaaaaagta gtgtgttctt gagcctatat aagagagggt cacacgctcc agtcgactca | 1260 |
| ccatcgatcc atctgacggt tagttccaag ggaaagaaga a | 1301 |

<210> SEQ ID NO 5
<211> LENGTH: 1243
<212> TYPE: DNA
<213> ORGANISM: Oryza sativa
<220> FEATURE:
<221> NAME/KEY: misc_feature
<223> OTHER INFORMATION: PRO0061 - beta-expansin EXPB9

<400> SEQUENCE: 5

| | |
|---|---|
| aaaaccaccg agggacctga tctgcaccgg ttttgatagt tgagggaccc gttgtgtctg | 60 |

-continued

```
gttttccgat cgagggacga aaatcggatt cggtgtaaag ttaagggacc tcagatgaac    120
ttattccgga gcatgattgg gaagggagga cataaggccc atgtcgcatg tgtttggacg    180
gtccagatct ccagatcact cagcaggatc ggccgcgttc gcgtagcacc cgcggtttga    240
ttcggcttcc cgcaaggcgg cggccggtgg ccgtgccgcc gtagcttccg ccggaagcga    300
gcacgccgcc gccgccgacc cggctctgcg tttgcaccgc cttgcacgcg atacatcggg    360
atagatagct actactctct ccgtttcaca atgtaaatca ttctactatt ttccacattc    420
atattgatgt taatgaatat agacatatat atctatttag attcattaac atcaatatga    480
atgtaggaaa tgctagaatg acttacattg tgaattgtga aatggacgaa gtacctacga    540
tggatggatg caggatcatg aaagaattaa tgcaagatcg tatctgccgc atgcaaaatc    600
ttactaattg cgctgcatat atgcatgaca gcctgcatgc gggcgtgtaa gcgtgttcat    660
ccattaggaa gtaaccttgt cattacttat accagtacta catactatat agtattgatt    720
tcatgagcaa atctacaaaa ctggaaagca ataaggaata cgggactgga aaagactcaa    780
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa   1020
gaatcgctcc cgcgcgcggc ggcggcgcgc acgtacgaat gcacgcacgc acgcccaacc   1080
ccacgacacg atcgcgcgcg acgccggcga caccggccat ccaccccgcgc cctcacctcg   1140
ccgactataa atacgtaggc atctgcttga tcttgtcatc catctcacca ccaaaaaaaa   1200
aggaaaaaaa aacaaaacac accaagccaa ataaaagcga caa                    1243
```

<210> SEQ ID NO 6
<211> LENGTH: 1019
<212> TYPE: DNA
<213> ORGANISM: Oryza sativa
<220> FEATURE:
<221> NAME/KEY: misc_feature
<223> OTHER INFORMATION: PRO0063 - structural protein

<400> SEQUENCE: 6

```
cctagctata tgcagaggtt gacaggttgt ctcttagatc gattaataat atcacattga     60
tgcaattaat tatctgagat caataaagtt tttctttatg ttaaattaat atcagtaata    120
gatgctaagt ccttcattag tagtatccca catttaatca cagttggaca cacaaaaaaa    180
aaggcaatgc cattaatatg ccatctctct tgttttccat tgcctaccaa gtgccatatg    240
atatcatcat caggcacacc aatccataac tagttcatta gagcaagttt aataatagag    300
ctaactataa gcttataatt tatattggag taaacatgta tagtaaatga gctataaggt    360
tatttctttt tttctcctcc tctctctatc tcttacctat atatttaatg tatttgtctt    420
gaagtatgtg aatagctagc tcttgtatga gagccaatcc tctgcatttt ttaaattctc    480
tttcctccac ataagcatat agttggctta tagcctgcta ttatacttgg tcttagtaca    540
ctaaccccccc ttcatgcaa tgcaagctgt ctaattaaaa gggtttcaca acattttgaa    600
tgccactact agctcccaac cacaaccaca gatctagcta gggtttgttc atttctctcc    660
tctctcctcc tcctccttc cgttgtgcca attcatccaa agtcattgag agccatacta    720
ctccatatca tattactcct acatgtgtac tacatttata ttgatgatct gtaagagcaa    780
aagtattaat ggggatcaca ggattgcagt aacagcagca ggtacccccct cctttaacat    840
```

| | |
|---|---|
| ccgcagttac gcctcccacc taccgtcttc tctgccgatc gatgacgatg agcttctcct | 900 |
| ccgctataaa tcctctcccc tcctctctcc ctcctcctcc aactccacat cgatcagcag | 960 |
| cagcagcagc ttgcacactc gagcttagct tagcttttgc aagagagatc gagctagag | 1019 |

<210> SEQ ID NO 7
<211> LENGTH: 1212
<212> TYPE: DNA
<213> ORGANISM: Oryza sativa
<220> FEATURE:
<221> NAME/KEY: misc_feature
<223> OTHER INFORMATION: PRO0081 - putative caffeoyl-CoA
    3-O-methyltransferase

<400> SEQUENCE: 7

| | |
|---|---|
| atggtgccat gtcaataaga catcataata gaaactacac tccacaaccc atagtttctt | 60 |
| aaagtgggtc attaataaat acatcatcta tcttttctat caatcatatt tattctttat | 120 |
| ctattatgac ggcactattt tctcccaatg taaaacttga taatgtctag tgcataggtt | 180 |
| ctcgtgttga agctgtttct tacatgagac ccagtttctt cttctctcca ctctctctta | 240 |
| attaatataa tgtcacataa gttaaaagtt ctagtaaata ataatatagt taatgacata | 300 |
| gacaacatcc tagatgtagg gttaggagtc ttcggacagt agcaaccctg ttttgactcc | 360 |
| ttttttggct gcccatccac agtcgccacc agaaaattca ctgtgcccaa atcaatggaa | 420 |
| gcgcctacta gatccatcca tcttcgtgac agctccgagc tttctcctgg ttattttttct | 480 |
| cccaaaaata cattcagaac acgatctcaa atttaaacta atggagtgct actgcatttc | 540 |
| ttaattataa gtcgcagcac cactcattaa tcatttccat cacaggtaaa tcgtggtgag | 600 |
| ctggtggttg ctactgtact actagtacta cctgtcgcag ctttgtagaa gccgttttcg | 660 |
| ctgaagcttc ttcttcttcc ctgggcaaaa taattttaag caggcggaat aatattggga | 720 |
| taaacagggt ggacaaaagc gtgcgatccc tttctttaac caaaccacga cgaaagcagg | 780 |
| ttaggtcgcg gcaggtggtg gtggtaggaa gaagaagaaa gagaggggaa aaaaaacaaa | 840 |
| aatttcacat gcatcatgca tgaagtagta catgtagtac tgagtactgt aataatgttc | 900 |
| agtttactgg accgtctcaa cgggaagacc aaattaacgc ttataaaata cccttttttt | 960 |
| gggcactgat catggccact acgtttggtg gctcaacaac caggtcaccg tgcgatcgat | 1020 |
| cgattgctaa tttatttttt gaaaggaag ggaggaaaaa agaccgggtg tttggtggcg | 1080 |
| ccaccaaccc tgctctcgtg agccgataaa tattgctcgc cggagctctc ggttgacgac | 1140 |
| ccaaccaatc gactcgcacc accaccagca gctcaagcag caacagctca aacggaggaa | 1200 |
| gatctcatcg cc | 1212 |

<210> SEQ ID NO 8
<211> LENGTH: 1052
<212> TYPE: DNA
<213> ORGANISM: Oryza sativa
<220> FEATURE:
<221> NAME/KEY: misc_feature
<223> OTHER INFORMATION: PRO0091 - prolamine RP5

<400> SEQUENCE: 8

| | |
|---|---|
| gtttttctat gaaccggtca ttaaaccgtc cccggttaga ccgaacaagc cacaataatc | 60 |
| ttgaaatggg ccttgatgtg gcccaattgg tctgcctaga gcgttttggt tggcaaaaat | 120 |
| caatctccta ttctcggcac gtgtgatata caatggtaag tgagatatac aattctcggc | 180 |
| acggctacat tacaaggtgt cgcattgtgt caatgtttgg ttaatttgct agattcacat | 240 |

```
aatacatgcc aggaagttca gaacaatgtg ttgcctttca ccggaaaact ttgttggagc    300
aaatgccttc ttctttttg cttctgcttc ttgagtccat gtggaggaag cagtagatag     360
ctgatgatat caggattcct tctgtgtctg tgtaggtgta gcaacaccac tataatttt     420 atttagcaac acaatatcaa tttggtctat aaaagtatga attaaatcaa tccccaacca    480
caattagagt aagttggtga gttattgtaa agctctgcaa agttaattta aaagttattg    540
cattaactta tttcgtatca caaacaagtt ttcacaagag tattaatgga caatgaaaa     600 ccattgaaca tactataatt tttttttctta ctgaaattat ataattcaaa gagcataaac   660
ccacacagtc gtaaagttcc acgtgtagtg cattatcaaa ataatagctt acaaaacata    720
acaaacttag tttcaaaagt tgcaatcctt atcacattga cacataaagt gagcgatgag    780
tcatgtcatt attttttgc tcaccatcat gtatatatga tgggcataaa agttactttg    840
atgatgatat caaagaacat ttttaggtgc acctaacaga atatccaaat aatatgactc    900
acttagatcc taatatagca tcaagcaaaa ctaacactct aaagcaaccg atagggaaac    960
atctataaat agacaagcat aatgaaaacc ctcctcatcc ttcacacaat tcaaacatta   1020
tagttgaagc atagtagtag aatcctacaa aa                                 1052

<210> SEQ ID NO 9
<211> LENGTH: 1216
<212> TYPE: DNA
<213> ORGANISM: Oryza sativa
<220> FEATURE:
<221> NAME/KEY: misc_feature
<223> OTHER INFORMATION: PRO0095 - putative methionine aminopeptidase

<400> SEQUENCE: 9
cctgatggat gatgaatcac tgatcgattt ctagttctta ttctctgaag atgaaccgaa     60
gatccaagat tggtccatga aattatcctt tcttgatttg gccctccgag aatagattcc    120
tgtgcaatct agtcagtagt tgttcaggtc atgtaaacgt acggtaagaa atttatgtgc    180
agagggtttt ccagtttatc ctatgcattt gacctctggt catgtattga ttctgagaca    240
aagtgtagtg atcgcttgat gatactagta cacattgctg ccttcttttt tgtcctgtaa    300
aagatttatt attggcagca atggatggta gagagggcaa tctgcttctt agttttgagt    360
ataaagtttt aagtttgag cagagtttcg aaaatttgca gtagaaagtt tgaaatttca    420
aattggaagt acagttttc aaatttccag tataaatttt taaacccact gagaaaccaa    480
gagcatatgg gcgatcaaaa atttcttttc taaaggaaaa atatttttta aaaaacactt    540
agtagtatat caaaattctg aggtaagctc attaggccca ttcactgtac ggcccatgaa    600
gcccagtctg gtgagatggg cctacccgt caggcagaga tggatgggcc tttaattgta    660
ggcccatgtt ggaaagccca ccaaagccca ataatatatc ctcctcacct tcaaccctaa    720
tcctcctctt cttctagaag actgaaaatt cctctccttt cttctctcgc cctcaccgct    780
cgccgaggtt gccgtctcct tgtctcctcc gctccttgcg ccgccgccgc gacgagtcgc    840
ggggaggggc ggcgatctcc atctccatct gaggcgagga gagcagggga ggtgagggga    900
tcctggtgag gtgagcatcc acgtcctctt tctttttttc tgattcatct ctctctctct    960
cgcacatcgg gactggaatt tgcttgcgtt cgttcgttaa gttaaccctca gcttctcttc   1020 tagatctgga agaaactctt cttcttttaa tttcagagcc ttaaccttaa tagtacaagt   1080 aacagttgt ttgttccccg aaaagttggg atgccttcca aatagagaca catgttattt    1140
attttggaat gtaatttgtc cctggattta ttcattcagg tttgtgatta ctggacaata   1200
```

-continued

| gaaatattta cacaat | 1216 |

<210> SEQ ID NO 10
<211> LENGTH: 1237
<212> TYPE: DNA
<213> ORGANISM: Oryza sativa
<220> FEATURE:
<221> NAME/KEY: misc_feature
<223> OTHER INFORMATION: PRO0111 - uclacyanin 3-like protein

<400> SEQUENCE: 10

| tcgttaagtt tgatgatttc tgatgaccca tggtcaccta gcggctagca gtaccatgca | 60 |
| tgatcaccct ccacaaagaa atggtacagt acatctccgt cccaaaataa gtgcagccat | 120 |
| gtatatccat gcctaacgtt tgaccgtccg tcttatttaa aaaaattatg aaaaatttaa | 180 |
| aaatatttag tcacacataa agtattattc atgttttatc atctaatagc aacaaaaaat | 240 |
| actaatcata aaatttttt taataagata acggttaaa cgttgaacgt gaatagtgca | 300 |
| aaacttattt tagaacggag ggagtacgaa gtaactccgg aactacatat agggcaatta | 360 |
| ttgccctatg tatgcatata gtcaatcaat taactgctga caatggaaaa gctaatcaat | 420 |
| caatcaatgg tttgattaat caaattaagc caggtcagtc cgtcagtgta cattcactaa | 480 |
| ttaaattaac aggtttgttc aacggttcaa ccaacatctg ccatcaacat cttttcgttg | 540 |
| cacctttctt gactctttat gctattttgc taaaaaaaaa cttctcttta catcacttat | 600 |
| aacaatatat atttctgctt taatttgtaa tcttttttt ctgcgttgca acggaaatca | 660 |
| cgagcgatat atggtgaaga ctgatgataa tcgtatttct gatgacccat gattccgcgg | 720 |
| tgtaccatct gttctgtcaa ctaaaaagtg gagtagttcc ttgacggaag aagggagcaa | 780 |
| aatagaagat attctcagtt gatctgcagt tgttgttagg tcactatatt cagaaatcgc | 840 |
| agttgctgtt gtttaaattg tgtgtgacag cagacagcta attatcagta cacgtatatg | 900 |
| agcaatacta gtgaatctgt actaatttaa cgagagtatt ttctatatac aaatacaaca | 960 |
| gcaaaactgt gccactggcg ccgaatacgt acggacagag ctcaggcaat caggggagca | 1020 |
| gcaaaagagg agagagttgg tgccaagcac aactaaaccc aactgcaccc aaaaactaat | 1080 |
| cagcatttca gttcgcttta gttagtacta ccacctgcat ctctttacca acactatata | 1140 |
| acccgcagtg gacctgcagt catctcacta attcagtgaa gccaccagta ctagtacggc | 1200 |
| tctaatcagt tcgcgtttgc taattaactc tgccatc | 1237 |

<210> SEQ ID NO 11
<211> LENGTH: 1100
<212> TYPE: DNA
<213> ORGANISM: Oryza sativa
<220> FEATURE:
<221> NAME/KEY: misc_feature
<223> OTHER INFORMATION: PRO0116 - 26S proteasome regulatory particle
    non-ATPase subunit 1 1

<400> SEQUENCE: 11

| ctaagggcag cagccattgg gctctatagg tgtggttgca agtgcactta caagcgagca | 60 |
| acctggtaga atatccccga gatcagtagt taccgtgatt ggttcagact tgagaggcta | 120 |
| attttttcgt acctgtagct ttattacatc gcatttcctc ttattgaagt ttagccgagg | 180 |
| tggtgcggat ggatattcag tctaacagac tcaatgaacg ctttgttgta tgacttgtac | 240 |
| agtactggct gctcgaacag gatggttcag cttccagaaa tttggcaacg ctccatttca | 300 |
| aagaaaatca ttcagtatt gccttcttgt tgttacattg atctcatata aagtcacttt | 360 |

```
gatcgttgac atcttgtttt ttggttcgtt tgccatggta gtttcccttg ctgctgggag      420
gattgccgcc tgaactttt cttttttgcg aggatgttat ttttgccaga caagaacggg      480
aataagcaaa ttgtttggtg gaactaaagt aaactcgatc tctttccgag aagtgtatta      540
ttttcacgtg taccatcaat ttttttgaaa gtaaatattt ttcccctta actaatgttc      600 actttggacc ggataatctt accttttattt aactttgggc tatctaactc tcttctaaag      660
catataaacg atcttgagta catcgattcc tactatcat ttaactctcg tagcttaatg      720
taagattatt tctttgaaat atgataaatt ggatgcatat gaatgaaaga gtcaaggatt      780
aagtgattcc tcaaaaaaaa aaaagagtga aatttattta tttttcccct ttcgacacga      840
agaagggctt ggttggagga aaatggccca gattcagatg accgaggccg agtaccatgg      900
ggcccacaag aataataagc cccgagccca aacgctaagg cccacgagaa gccgtgcgct      960
ggaagaaaga aagaaaccgc ggccgtcttc acaccgaagc ggcggacgag acgactcgca     1020
gtcgcagcct ctttcctcct ccgtctctct ctcccctctt cctctcctcc gcgcggcgaa     1080
cgaagcgagc gagcggcggc                                                1100

<210> SEQ ID NO 12
<211> LENGTH: 1216
<212> TYPE: DNA
<213> ORGANISM: Oryza sativa
<220> FEATURE:
<221> NAME/KEY: misc_feature
<223> OTHER INFORMATION: PRO0117 - putative 40S ribosomal protein

<400> SEQUENCE: 12
cgtgttcatg ttcgcattta ggattggact ttttaggat ggagaggata tgtcctaacg       60
gaaatgtcat gtctatgctc cgatcttata aatttgttca atagcgttgc aaacgcgatc      120
attaaaaagg cggtaagaga actaccacat tttcgaaagc ccattctctt cgtgagttac      180
tggaattatt tggcatagca catgcataaa gatgctttag taatgagctc aataaaacac      240
gacagctttg catgtagcca caatgctata gtaaatgagt tgtacttctt ttgcattgca      300
aagtggtact gaccttgttt aggcagctag cttcattcat ttttttgaatt ctatagttat      360 agttataaag attatcataa tttagataag aatccggtat gtttgagaag ctggagtttc      420
tagagaagct ataacaactc gaagctccct aaacagagcc attgaacatt gagctgtcca      480
gtatatcatg acaaaatgat acattttgca tgggcatatg tgtctaagaa acaaacatc       540 acaattcaat gagtcactct aaaaaaaaag gcaaaacact caacaaaacc ataccgtgaa      600
agtgaaccta taatgaaatg aaattttgat aagcatgctt acccaggtgg aaatttcaat      660
ctaagaacaa tttccaaaac caccgtccat agaaatatgt ggaattcatt cagaattttc      720
ataccacacg ataaaattta tagggaattt aacttttgcc attttaccg aacaccacct      780 tttcatttgc tcctataatg ttatcgaaaa gagagtgtt gttaattatt tgtcactttt       840
atcacgacat gtagccgtga caacgtggcg ttcctcgtgg agcccacccg tcagccgccg      900
tacgcaccac catcaaagaa ttcaagacgg agagcgtcgt cgccgtcggc aaggcggcgt      960
gttttgttca ctgtacgttg cttcggcgtg ggcccaatct tgttcgggcc taactagttc     1020 ttccagccc aggcccatta agcctaccaa cccggacggc ccgggaggag ctagggtttc     1080
acccttcact atataaacct ctctctcctc ctccggccgc cgcctccgaa gccctagctc     1140
ctcccgccgc cgccgccgcc gccgccgccg cctctccact cgagagaccc agccgccgcc     1200
gccgccgccg ccgcca                                                    1216
```

<210> SEQ ID NO 13
<211> LENGTH: 1210
<212> TYPE: DNA
<213> ORGANISM: Oryza sativa
<220> FEATURE:
<221> NAME/KEY: misc_feature
<223> OTHER INFORMATION: PRO0122 - chlorophyll a/b-binding protein presursor (Cab27)

<400> SEQUENCE: 13

| | | | | | |
|---|---|---|---|---|---|
| cagatgccac | agtatggtgt | accaccagct | gctccacacc | atgctccacc | ggctggccaa | 60 |
| ccaatgtatt | tcccgaaata | atctatcttt | atccgatgta | caagcaatta | gagcaattgc | 120 |
| aaatgttgcc | tgcaatactc | gggtctgggt | atcttctctt | caaattttgg | gttgtaactc | 180 |
| gtctatgcag | ctattcatat | tgtaactcag | tgagctccct | gtcgcaaatg | tgcctctgcg | 240 |
| tcagtcgctg | tctgtaaact | gtccggcaat | tagaaattcc | catccttagc | atgcctggta | 300 |
| ttgttcagct | cgaaactgaa | attttcttc | gtgccctata | ttttttcggt | gtagataagt | 360 |
| gttccgctgg | aattttatgc | aggtgctgta | ccctatgtgc | tgcttttttt | ttgtgtgggg | 420 |
| cgccccccg | gggggggggg | ggggtttcct | ggcatgattg | caaataagaa | cccccggggca | 480 |
| aatctgctgg | ttggttgcaa | ataataaccc | ctccaaatct | gcgcagatga | aaccccattc | 540 |
| aggacatgaa | ttacgattgt | tcatgagcta | tttggatcat | ggaaagattg | gaaacaaaca | 600 |
| cttacgtcaa | ggtttctact | aattacgtga | ttccgatttc | agagtcagcc | atggctatac | 660 |
| tgcctttgct | ccagtaaaca | tcgctgctct | agtaacaaac | attgcagtaa | acatcacaac | 720 |
| tatccaattc | ccttgttgct | gctctagtaa | aaaacattgc | aattatccaa | ttcccagata | 780 |
| ttttctttca | ctactccaaa | acctaaagta | catatacgtg | agttgagtga | tccagcaaca | 840 |
| taaaaatccg | aggctccgag | cgatctgcac | caaccatctc | acccgtccga | cgtggcagca | 900 |
| gcaaccagcc | acagctgaga | cctccatcca | atagaaaccc | tcccttttgat | tccccgtat | 960 |
| cccggcatcc | ggataacgct | ggataagagg | cgacgcctcc | cattggccac | acccacccaa | 1020 |
| caacgcatcc | tggccgtccg | atccacccccc | accgccgatc | tccgccgtcc | gtcgccgccc | 1080 |
| tcgccaccgt | ggccacctgg | cagcgccggc | cactcccgga | cagtttaata | caagccacgc | 1140 |
| ctttgctccg | tgccggccaa | aacgtaccct | tgtgactaca | cccgcttcgc | ttcctcccct | 1200 |
| ctctaagccg | | | | | | 1210 |

<210> SEQ ID NO 14
<211> LENGTH: 1179
<212> TYPE: DNA
<213> ORGANISM: Oryza sativa
<220> FEATURE:
<221> NAME/KEY: misc_feature
<223> OTHER INFORMATION: PRO0123 - putative protochlorophyllide reductase

<400> SEQUENCE: 14

| | | | | | |
|---|---|---|---|---|---|
| ttgcagttgt | gaccaagtaa | gctgagcatg | cccttaactt | cacctagaaa | aaagtatact | 60 |
| tggcttaact | gctagtaaga | catttcagaa | ctgagactgg | tgtacgcatt | tcatgcaagc | 120 |
| cattaccact | ttacctgaca | ttttggacag | agattagaaa | tagtttcgta | ctacctgcaa | 180 |
| gttgcaactt | gaaaagtgaa | atttgttcct | tgctaatata | ttggcgtgta | attcttttat | 240 |
| gcgttagcgt | aaaaagttga | aatttgggtc | aagttactgg | tcagattaac | cagtaactgg | 300 |
| ttaaagttga | aagatggtct | tttagtaatg | gaggagtac | tacactatcc | tcagctgatt | 360 |
| taaatcttat | tccgtcggtg | gtgatttcgt | caatctccca | acttagtttt | tcaatatatt | 420 |

```
cataggatag agtgtgcata tgtgtgttta tagggatgag tctacgcgcc ttatgaacac      480
ctacttttgt actgtatttg tcaatgaaaa gaaaatctta ccaatgctgc gatgctgaca      540
ccaagaagag gcgatgaaaa gtgcaacgga tatcgtgcca cgtcggttgc caagtcagca      600
cagacccaat gggcctttcc tacgtgtctc ggccacagcc agtcgtttac cgcacgttca      660
catgggcacg aactcgcgtc atcttcccac gcaaaacgac agatctgccc tatctggtcc      720
cacccatcag tggcccacac ctcccatgct gcattatttg cgactcccat cccgtcctcc      780
acgcccaaac accgcacacg ggtcgcgata gccacgaccc aatcacacaa cgccacgtca      840
ccatatgtta cgggcagcca tgcgcagaag atcccgcgac gtcgctgtcc cccgtgtcgg      900
ttacgaaaaa atatcccacc acgtgtcgct ttcacaggaa aatatctcga aggaaaaaaa      960
tcgtagcgga aaatccgagg cacgagctgc gattggctgg gaggcgtcca gcgtggtggg     1020
gggcccaccc ccttatcctt agcccgtggc gctcctcgct cctcgggtcc gtgtataaat     1080
accctccgga actcactctt gctggtcacc aacacgaagc aaaaggacac cagaaacata     1140
gtacacttga gctcactcca aactcaaaca ctcacacca                            1179

<210> SEQ ID NO 15
<211> LENGTH: 1808
<212> TYPE: DNA
<213> ORGANISM: Oryza sativa
<220> FEATURE:
<221> NAME/KEY: misc_feature
<223> OTHER INFORMATION: PRO0133 - chitinase Cht-3

<400> SEQUENCE: 15
tttggcgcgg ggcagaagag tggactttaa ctttcttttt aataaaatct ccaattaata       60
tgtaattata atatactttt aatcaaaaca tgcaaagcta gcagtattta catcactaga      120
agtaaatctt tcttgctcat gatgcttcag ccggacggaa ccctaaaata tagatggggc      180
ggatacactc gattaaaaca gctaattgca acacatatca tataaggttt tggaattcat      240
accaaatgct ccgaaattcg tctatttcga tgaggcccaa gacatgacct cctgtttcgc      300
ccatagttta tggtgtttgg taaaatttgg ttaaaatctg tctattttag taggtcccga      360
aattcttatg caattgaatc ctagaaccct atcatattta tattgcaatt gcacaaaaat      420
aatgtgcaat caatatattc caattgcaat acatatcaag catgaggtgt aatacatatc      480
cagccgctag cactgggtct gttgaggtgc ttcttgcagc aacagctgca atctgtttgg      540
ctaggctgtt ggcgccaggc actgctgtcg tgctgcaaca atggcacatt cgtcgagcac      600
acaaccgcgc ctatgcacag cgcaagctcg ctgccttgga ccgtggttcc agtgttgcat      660
caaggcttag tggattgagc gagaagacga actgacaatg ccaaagatgc gatgctgcga      720
gtgtggactg cggaagatga atcgagatca atcaattcgt tatgcttgaa aggctggaat      780
aactgatcag ttggctggat cgatggtatg tactagataa tatgcggtct aggcctagac      840
caagaagcag aagaggagtc gggtcgggag tgtggggcga cgtaggctgt agctgggccg      900
gccgccccag gccgcctaat gagtgtgtcc gcccctggcc tgacacgatg ggtaattaaa      960
tagttatgca tgtccctctt tgtctaaaca atatgtataa aattgacgat atcttgggca     1020
aaatcactgg gcatggcaca caggagagct actttagcga catgaatcta ggcgaaaatc     1080
tattgaacca aaaatcgact gtaatctcat gaaaattttc gtcataatta tagcaaaatc     1140
gttgttggat tgattgcacg agaaaacaga agaagggagc taggtgatat tatattgttt     1200
tgttgcctac ataaatctta aagcaatcga atggtctaaa atttacaaga ttttttaaaga    1260
```

-continued

```
ggttttcgta ccgtatagac cccggccggg tcaaacttat ttggtcgtcg ctggttgttt      1320
gtagcacgcc agctccatat atgtggattg cagctggtct atgataagtt cggtcgatct      1380
gagatcaatc tatcaatcgt caacccttttg cctttgttag cgagctagcg tgtacacatt     1440
tcaattatat atggtgcatg catggcatcc acgcctccac ggtcaacgtg gaaatatctc      1500
tggaaactta cttttttctaa ataactgaac ggattggagg caggagacaa atttgaccaa     1560
cacaatatat ccacgacggc tagacaatac tagtagatgc atgcatggaa ggatatagta     1620
gtacttgtta atcgtggaaa ctttggtaat gcgaatgcat ttcaattcgt tgctgaagat     1680
cgatgcacca tgcatatcca tctctatata aagccatgcg atcccaccga ttcttgcaca     1740
cacactagct acttctactt ctatcatacc aaacaaacta gcttaatttg cattgcatca     1800
cattgccg                                                              1808
```

<210> SEQ ID NO 16
<211> LENGTH: 1828
<212> TYPE: DNA
<213> ORGANISM: Oryza sativa
<220> FEATURE:
<221> NAME/KEY: misc_feature
<223> OTHER INFORMATION: PRO0151 WSI18

<400> SEQUENCE: 16

```
gcttgagtca tagggagaaa acaaatcgat catatttgac tcttttccct ccatctctct       60
taccggcaaa aaaagtagta ctggtttata tgtaaagtaa gattcttttaa ttatgtgaga     120 tccggcttaa tgcttttctt ttgtcacata tactgcattg caacaattgc catatattca     180
cttctgccat cccattatat agcaactcaa gaatggattg atatatcccc tattactaat     240
ctagacatgt taaggctgag ttgggcagtc catcttccca acccaccacc ttcgtttttc     300
gcgcacatac ttttcaaact actaaatggt gtgtttttta aaatatttt caatacaaaa      360 gttgctttaa aaaattatat tgatccattt ttttaaaaaa aatagctaat acttaattaa     420
tcacgtgtta aaagaccgct ccgttttgcg tgcaggaggg ataggttcac atcctgcatt     480
accgaacaca gcctaaatct tgttgtctag attcgtagta ctggatatat taaatcatgt     540
tctaagttac tatatactga gatgaataga ataagtaaaa ttagacccac cttaagtctt     600
gatgaagtta ctactagctg cgtttgggag gacttcccaa aaaaaaaagt attagccatt     660
agcacgtgat taattaagta ctagttttaaa aaacttaaaa aataaattaa tatgattctc     720
ttaagtaact ctcctataga aaacttttac aaaattacac cgtttaatag tttggaaaat     780
atgtcagtaa aaaataagag agtagaagtt atgaaagtta gaaaaagaat tgtttttagta    840 gtatacagtt ataaactatt ccctctgttc taaaacataa gggattatgg atggattcga     900
catgtaccag taccatgaat cgaatccaga caagtttttt atgcatattt attctactat     960
aatatatcac atctgtctcta aatatcttat atttcgaggt ggagactgtc gctatgttttt   1020 tctgcccgtt gctaagcaca cgccaccccc gatgcgggga cgcctctggc cttcttgcca    1080
cgataattga atggaacttc acattcaga ttcgataggt gaccgtcgac tccaagtgct      1140
ttgcacaaaa caactccggc ctcccggcca ccagtcacac gactcacggc actaccaccc   1200 ctgactcccct gaggcggacc tgccactgtt ctgcatgcga agctatctaa aattctgaag    1260
caaagaaagc acagcacatg ctcccgggaca cgcgccaccc ggcggaaaag ggctcggtgt    1320
ggcgatctca cagccgcata tcgcatttca caagccgccc atctccaccg gcttcacgag   1380
gctcatcgcg gcacgaccgc gcacggaacg cacgcggccg acccgcgcgc ctcgatgcgc   1440
```

```
gagcccatcc gccgcgtcct cccttttgcct ttgccgctat cctctcggtc gtatcccgtt    1500
tctctgtctt ttgctccccg gcgcgcgcca gttcggagta ccagcgaaac ccggacacct    1560
ggtacacctc cgccggccac aacgcgtgtc ccccctacgt ggccgcgcag cacatgccca    1620
tgcgcgacac gtgcacctcc tcatccaaac tctcaagtct caacggtcct ataaatgcac    1680
ggatagcctc aagctgctcg tcacaaggca agaggcaaga ggcaagagca tccgtattaa    1740
ccagcctttt gagacttgag agtgtgtgtg actcgatcca gcgtagtttc agttcgtgtg    1800
ttggtgagtg attccagcca agtttgcg                                       1828

<210> SEQ ID NO 17
<211> LENGTH: 1267
<212> TYPE: DNA
<213> ORGANISM: Oryza sativa
<220> FEATURE:
<221> NAME/KEY: misc_feature
<223> OTHER INFORMATION: PRO0169 - aquaporine

<400> SEQUENCE: 17
cgtcctcctt ttgtaacggc tcgcaaatac aatgggttgt ttagattcat gtcattttaa      60
atcatattat tttttataaa gttatcaaaa tgtacatata tttatttatt tttaccaaac     120
tttactaaat gagataatcc aacaaatggc atttaaagcg ttcaaatcca agaaatgcca     180
tcgccgttat gcttccgtcc gtttcacgcc gttaaaatac aatgttcatc ctataacact     240
taatggtgtg gaatggacgg aaccctaacg gcgatggcat ttttgggata aagtcgtttg     300
tacgatggca tttcttagaa ctcatatttg tcgatggcat tttttgaatt tggatgattg     360
tcaatggtat tttttggatt atctcttagt aaatacataa ggaatcatgc caaaacttga     420
caatattgtc aacttatcaa aatttaattg ggattatttt ggcgataata tgaacagccc     480
ttacatttct gaagaattat agctcaaata tggctatggc cctgtttgga ttcggagggc     540
tatttaatag ccctccggaa tcttgctatt taagagtatt aaacgtagat tactgataaa     600
actcattcca taaccctac gctattctac gagacgaatc taacgaggta tattaatcca     660
tgatttgcta cagtaatcag ccgctaatcg tggattaata tacatcatta gattcgtctc     720
gtaaaatagg ctagggatta tggaatcggt tttatcggta atctatgttt aatacttcta     780
aatagcaaga ttccgaaggg ctatttaata gctcggagca tccaaacaag gcctatgttt     840
agatccaaac ttccaacttt ttctatcaca ttaaactgtc atacatacat aacttttcag     900
tcacatcgta ccaatttcaa cccaaacttt caactttgga agaactaaac acagcatatg     960
acagtgcagt tcagctcaat tttgttcgga gcctaaaaaa aagaaaagaa aaaaagctca    1020
atttggataa ggctatgaat aaactcaaaa aagcatccaa cctaaccacc acactggccc    1080
accagggccc acgctccact cccgtgatca tcacctcctt cccttttcag aaccaccttc    1140
tccttccttc ctcctcttct tcttcagtgt actctgcctt tataacaccc tactcctctc    1200
tctcacctcc accatctagc tcactcacac agtctccact cacacgcatt gcagaggaga    1260
ggcgaca                                                              1267

<210> SEQ ID NO 18
<211> LENGTH: 1130
<212> TYPE: DNA
<213> ORGANISM: Oryza sativa
<220> FEATURE:
<221> NAME/KEY: misc_feature
<223> OTHER INFORMATION: PRO0170 - High mobility group protein
```

```
<400> SEQUENCE: 18
catgcggcta atgtagatgc tcactgcgct agtagtaagg tactccagta cattatggaa      60
tatacaaagc tgtaatactc gtatcagcaa gagagaggca cacaagttgt agcagtagca     120
caggattaga aaacgggac  gacaaatagt aatggaaaaa caaaaaaaaa caaggaaaca     180
catggcaata taaatggaga atcacaaga  ggaacagaat ccgggcaata cgctgcgaaa     240
gtactcgtac gtaaaaaaaa gaggcgcatt catgtgtgga cagcgtgcag cagaagcagg     300
gatttgaaac cactcaaatc caccactgca aaccttcaaa cgaggccatg gtttgaagca     360
tagaaagcac aggtaagaag cacaacgccc tcgctctcca ccctcccacc caatcgcgac     420
gcacctcgcg gatcggtgac gtggcctcgc cccccaaaaa tatcccgcgg cgtgaagctg     480
acaccccggg cccacccacc tgtcacgttg gcacatgttg gttatggttc ccggccgcac     540
caaaatatca acgcggcgcg gcccaaaatt tccaaaatcc cgcccaagcc cctggcgcgt     600
gccgctcttc cacccaggtc cctctcgtaa tccataatgg cgtgtgtacc ctcggctggt     660
tgtacgtggg cgggttaccc tgggggtgtg ggtggatgac gggtgggccc ggaggaggtc     720 cggcccccgcg cgtcatcgcg gggcggggtg tagcgggtgc gaaaaggagg cgatcggtac     780
gaaaattcaa attaggaggt gggggggcggg gcccttggag aataagcgga atcgcagata     840
tgcccctgac ttggcttggc tcctcttctt cttatccctt gtcctcgcaa ccccgcttcc     900
ttctctcctc tcctcttctc ttctcttctc tggtggtgtg ggtgtgtccc tgtctcccct     960
ctccttcctc ctctccttc  ccctcctctc ttcccccctc tcacaagaga gagagcgcca    1020
gactctcccc aggtgaggtg agaccagtct ttttgctcga ttcgacgcgc ctttcacgcc    1080
gcctcgcgcg gatctgaccg cttccctcgc ccttctcgca ggattcagcc                1130

<210> SEQ ID NO 19
<211> LENGTH: 1230
<212> TYPE: DNA
<213> ORGANISM: Oryza sativa
<220> FEATURE:
<221> NAME/KEY: misc_feature
<223> OTHER INFORMATION: PRO0171 - reversibly glycosylated protein RGP1

<400> SEQUENCE: 19
tagtaccatt cttccctcgt gagcataaat gtattcatac aaaatagtaa aatgtatcct      60
cacaaagatt gtaagtatat ctcgcaacta aaatatgtt  gtcattttag taacaattgt     120
tcataaaata gtaatcatgt tctccataac agtaaatgac gaggcgttaa tagtggttta     180
ggttctcatg attgtaaatg ttgagtcgct tgtagcggct taagatatag tagagagtat     240
atctagtttt atcaagacaa acattgcgta atgcctcgga cctaatataa aagtaggaat     300
tttaaccttt gagaaactgt aaccaattga aactgcaagc tttaaaaaaa catctattgg     360
aagtgatatt atatagacaa ataagtttc  ttactcttac tctctcagtt tcaagttata     420
aaatgttttg gctttggtca aaatcaaact tcttcaagtt taatcaagtt tatagaaaaa     480
atagtaatat ccaagataaa tttattataa aaatatattt aattattatt ttaataaaac     540
taatttggta atgtaaatat tactatattt gtctataaac ttagtcaaat ttaaaacagt     600
ttaactttga ccaaagtcaa aacatctctat aacctgaaat ggatggagta tttgtttgtt     660 tctatttttag gaaacggccg tttctttcca ttgattttga gataagcaga gctttaaacc     720
actgccacta ttgtgcattt catttgattt aacactttta cccttatct  ccaataaaaa     780 cgatattaag ataccctat cttttatcca ccgcttggaa caaaccaaaa aaaataaaaa       840
```

```
ttcaaacctt ctacactggt acacacgttc tctctttcca tgcaccgaca ggtctctccc      900
agatccaacc caaaataaat ttggacgcat cccaaaattc ggcaaacata tgacgcaaac      960
caaaacaaaa taggcacaaa ataatataat actcctatct aattaattat acacaatttt     1020
ttttaaaaaa aaagcaaggc aagcgaagca aagcaaagaa ggaaacgaat aacaaagtcg     1080
tcgtcctccc ggagctcccg ctctataaat cgctcctcct ccccacccac ccaaacccac     1140
acacacctca cacctcacca ccatcacctc ctcctcctcc tcctcttcct ccgcgcgcgc     1200
gagatccagg gagagggaga gggagagatc                                      1230
```

<210> SEQ ID NO 20
<211> LENGTH: 1234
<212> TYPE: DNA
<213> ORGANISM: Oryza sativa
<220> FEATURE:
<221> NAME/KEY: misc_feature
<223> OTHER INFORMATION: PRO0173 - cytosolic MDH

<400> SEQUENCE: 20

```
gtttggttgg tgaccgcaat ttgctatacc aaaatcttag acacagttga attaagctac       60
actttattag cacattggcc cgtgcgttat attgtcattt tctagccaaa gtttgccata      120
attgtggcta acaaattgtt ggccacattt tggctacgtt cgataggaca tgttcccaac      180
ttctccttct cgttttcgc gcgtacgctt tttcaaactg ttaaacggtg tgttttttgc      240
aaaatatttt tttacgaaag ttgcttaaaa aattatatta atctattttt tttaaaaaaa      300
gtagctaaaa cttaattaat ctcacgctag acgctgcttc gttttacgtg tcgggtaccc      360
aaccctcact cccgaacaca gcctttgtgt ggtttactac agttatagta aagctagtct      420
ccatccaaac aatcctttag tccatataac ttcgtatact ccaaaattcc actcgttcta      480
cggacatcac taatacgaag atcaagtgga agatagatat ttttaatgac atgttatttt      540
cagtgaacac ttgaggtcct cacgatccac aaacacacat tttcgtagat aagttctgaa      600
atactccata cggcggttgt cacgatgtca tgatcgtcgt tacccaagga agaagaaaag      660
agtggcatct tctccacgcc agtgttccca acggagcatc ttttcttccc ccacacggca      720
tcgacgtcac actttctggt gcaaacttta ataattagtc caaaaacaaa aaaagaattt      780
cggccacatc ttctcccgaa acgccaggtg ggccccacct gcatcactga cagcctgtcc      840
ccacaacgcg cagtcgtgtc cccacctgtc aggatgttag cgtctccgtt gcaggtttcc      900
cagatcccat cgccgatctg tgggccagcc cccacggtgt cacgcccgcg cacacctggc      960
tccaacccac ccaccccacg cgctccgtgg ccgacagcgt ggacccacct aggtggggcc     1020
caccgtcagt gggagatggg taggggagcc cccacgtggg agcaacgggg gttctccggg     1080
ctccccgtcg ccgcgaggtt aaataacggc cacccgtttc cccctctctc gcaaaactca     1140
cccaaaagag cagcgtcgcc tctcctcctc cccctaacc cctacgcttc cagaaccttc     1200
tcgaagctcc cgctcccccc ccccttccgc tcca                                 1234
```

<210> SEQ ID NO 21
<211> LENGTH: 1553
<212> TYPE: DNA
<213> ORGANISM: Oryza sativa
<220> FEATURE:
<221> NAME/KEY: misc_feature
<223> OTHER INFORMATION: PRO0175 RAB21

<400> SEQUENCE: 21

```
gtcaccaccg tcatgtacga ggctgcttca ccactgcctc actgccacca gcgtctcccg       60
```

```
ccgcgtgcaa tacaagaaga aacatcgaac ggtcatataa ggtaagaccc actaccgatt    120
taacctatca ttcccacaat ctaatccact tatttctctt cccatgatct tatcctctca    180
tttctcctca ctacttttgc atttgtagga aacacaatga caccgtcgaa gaaagctggt    240
ggagcaccgt agccagcaat caccaaaaca cagaggggag gaggtcggca gcggccatgc    300
ggacggcgat gagacaacgc gacgcaaaga gggaggagga cgttggcgat catgctggtg    360
ttggcggagg aggtcactgg ccatgcgaat gacagcgggg cagcgcaaca caaaaagggg    420
ggaggatgcc ggcgaccacg ctagtaccat gaagcaagat gatgtgaaag ggaggaccgg    480
acgagggttg gacctctgcc gccgacgtga agagcgtgat gtgtagaagg agatgttaga    540
ccagatgccg acgcaactta gccctgcaag tcacccgact gcatatcgct gcttgccctc    600
gtcctcatgt acacaatcag cttgcttatc tctccatact tgtcgtttgt ttcccgtggc    660
cgaaatagaa gaagacagag gtgggttttg ttggagagtt ttagtggtat tgtaggccta    720
tttgtaattt tgttgtactt tattgtatta atcaataaag gtgtttcatt ctattttgac    780
tcaatgttga atccattgat ctcttggtgt tgcactcagt atgttagaat attcattccg    840
ttgaaacaat cttggttaag ggttggaaca tttttatctg ttcggtgaaa catccgtaat    900
attttcgttg aaacaatttt tatccgacag caccgtccaa caatttacac caatttggac    960
gtgtgataca tagcagtccc caagtgaaac tgaccaccag ttgaaaggta tacaaagtga   1020
acttattcat ctaaaagacc gcagagatgg ccgtggccg tggctgcgaa acgacagcgt    1080
tcaggcccat gagccattta ttttttaaaa aatatttca acaaaaaaga gaacggataa   1140
aatccatcga aaaaaaaaaa ctttcctacg catcctctcc tatctccatc cacggcgagc   1200
actcatccaa accgtccatc cacgcgcaca gtacacacac atagttatcg tctctccccc   1260
cgatgagtca ccacccgtgt cttcgagaaa cgcctcgccc gacaccgtac gtgcgccacc   1320
gccgcgcctg ccgcctggac acgtccggct cctctcccgc cgcgctggcc accgtccacc   1380
ggctcccgca cacgtctccc tgtctcccte cacccatgcc gtggcaatcg agctcatctc   1440
ctcgcctcct ccggcttata atggcgcc accaccttca cctgcttgca caccacagca   1500
agagctaagt gagctagcca ctgatcagaa gaacacctcg atctctgaga gtg         1553
```

<210> SEQ ID NO 22
<211> LENGTH: 1087
<212> TYPE: DNA
<213> ORGANISM: Oryza sativa
<220> FEATURE:
<221> NAME/KEY: misc_feature
<223> OTHER INFORMATION: PRO0177 - Cdc2-1

<400> SEQUENCE: 22

```
cagacaccta gaatatagac attcccaaaa aataatcact atgcatcagc atcactatac     60
atgacttggg tctagtgatg gaagtggata gttccactac ctacataaaa acccactact    120
agtttattac ttttcacatg atagcataaa atttaaagaa aaaataaaca gaagtggaat    180
aagcgaaaaa ccccgcttac ccgccccatt tacatcccta cttggatcct gcatgtcagt    240
aagatatcag aattatatgt tttagaatta tatgtttttt tggaaggtgg aaatcggatt    300
attagacgca acataccaag tggcgtatac ttggcttcac tctttccatc agagcaagcg    360
taaaagatca cgtattcacg tcacatggag taactgagcg aattttttc attttaaat    420 ttttgttttt taatatttac ataaatatta taccggcgaa aatatttaca aaagtagacc    480
ctgctgccct tctccttctc gagaagagcg gcagggtgat gtcagggaca gaaataaact    540
```

| ccaaaaatgc attttttggct gggcgaaaat tgcacttacc cccttgctgc cctctacaaa | 600 |
| ggttgcaagg gacctcagtg caaaatacgc acaccttgcc gtcctccact tggacggcat | 660 |
| gggctatttc tgtaaatatt ttggatggta taatatttct gtaaatatta aaaataaaa | 720 |
| atttaaaaat gaaaaaattc tatctgggct cccttctctc atctcacacg cccaccaca | 780 |
| caatcccggc ccacatattt cctgggccca tttccgtgtg aatggagacg cccattggc | 840 |
| gcgcacatgc ggaaaagcgt acacacgatt cgaaatttga atctcaaaa agcgcccgtt | 900 |
| agagcgcgtc ccctccaacg gctatcccca atacaaaaga tcactcgaat ccccccaaa | 960 |
| tcgaccaaac cctaaatcca cgcgcattcc acaccaccca accagcgaga gagagatggc | 1020 |
| ggcgctccac caccaggcgg cggcggcgcc ggtgacgacg acgacggacg ggggcgagct | 1080 |
| gcgggcg | 1087 |

<210> SEQ ID NO 23
<211> LENGTH: 1272
<212> TYPE: DNA
<213> ORGANISM: Oryza sativa
<220> FEATURE:
<221> NAME/KEY: misc_feature
<223> OTHER INFORMATION: TC89946 (PRO0110)
<220> FEATURE:
<221> NAME/KEY: misc_feature
<222> LOCATION: (17)..(17)
<223> OTHER INFORMATION: n = any nucleotide
<220> FEATURE:
<221> NAME/KEY: misc_feature
<222> LOCATION: (50)..(50)
<223> OTHER INFORMATION: n = any nucleotide

<400> SEQUENCE: 23

| tttgacgact gaatcgnggc tcgcctctgc ggcggccgct ctagattagn gtttcccctg | 60 |
| tctgttgtaa ttcggcacga gggctgatca agagctctta attagctagc tagtgattag | 120 |
| ctgcgcttgt gatcgatcga tctcgggtac gtagcaatgg cgtccaaggc gttcgctctg | 180 |
| ttcctggccg tgaacctcgt cgtgctcggg gtggcaagcg cctgcggcgg cagcccgtcg | 240 |
| tgcccgacgc cgacgccgtc gaccccgaca ccgtcaacgc cgacgccgac gccgtcggcg | 300 |
| ttcgggaggt gccccgcga cgcgctgaag ctgggcgtgt gcgccaacgt gctgggcctg | 360 |
| atcaaggcca aggtgggcgt gcctccggcg gagccgtgct gcccgctgct ggaggggctc | 420 |
| gtcgacctcg aggcggcggt gtgcctctgc acggccatca gggcaacat cctcggaatc | 480 |
| aacctcaacc tccccatcga cctcagcctc atcctcaact actgcggcaa gaccgtcccc | 540 |
| accggcttca agtgctaagc agcgtgcata tgcaatgcct gcatggggttg atcctacgta | 600 |
| cggtgattag ttggctttga cgactcttga tttgatttgc ttgctgctct gtttatttgc | 660 |
| tactacgtta cgtacgtact ttgcatgcaa cgcaacgcat gatcgatcgt gcatgctggc | 720 |
| tgtttgtacg tatcacggta ccagtttgga ttctctctgt actctctcct ttgtcttctt | 780 |
| tgtagtactc ttattcccgc tatccgtacg tgcgcatttg ttgtaagggc cggtgctagc | 840 |
| ttgtgtgccg gtaccaactt ctaataaagc tatgggtgga acttcaaaaa aaataaaaaa | 900 |
| aaaactggag ggggggcccg gtccaattt agactataat gagtttaaca ccccgctcat | 960 |
| cggccgaaga taacaacacc gggcttggaa aacctagact gcccaactaa tggacggaag | 1020 |
| acagactctt ggactgaaac tgaacgaaac aagaccaccc accccatcta accacagcca | 1080 |
| cctaccgcca aagattccaa taatgtgaat cagtcggtaa tagaacactc ctcttgtacg | 1140 |

```
attttactgc cgcgccacc cctcggtacg cacttatata tatcgggccg tagtaatttc    1200
ctggttccgt cacttccctc atcgcacctg ctagtcgtgg cttacatacg tgcgtcctct    1260
tattatcgag cg                                                         1272

<210> SEQ ID NO 24
<211> LENGTH: 2425
<212> TYPE: DNA
<213> ORGANISM: Oryza sativa
<220> FEATURE:
<221> NAME/KEY: misc_feature
<223> OTHER INFORMATION: TC90358 (PRO0005)
<220> FEATURE:
<221> NAME/KEY: misc_feature
<222> LOCATION: (1558)..(1558)
<223> OTHER INFORMATION: n = any nucleotide

<400> SEQUENCE: 24
cccacattga ataattattt taaataattt aagttttttt tttttggctt tagatatatt      60
cccaatcccc aacctcccaa taatccgatc tctcccagtt ctgttcggat caaggctgtg     120
tcgatcgcaa aaagaaaaa aaaaacaatt tccttttggg gtggttcatc tgttgatcac     180
ttctttgttt cccgcgtttt gttggggatt cgattttcgg gttaagattt tctacacgat     240
ggccttgaac ttggctcaga gcgccgcggc ggcagcgtgc ttcgcgaccg ccggtgatgc     300
gcggcgagct gcttcggtgg tcgccatgcc gtcgtcgtcg tcgtcggcca cgacgagcct     360
gaggatgaag aggcaggcgg cgtgcgagcc ggtggcgtgc cgggcggtgg ccaggcacgt     420
ggcggcggcg gcggcgagca gcaggaggaa cggcgtgccg gtgttcgtga tgatgccgct     480
ggacacggtg agcaagtgcg ggagcgcgct gaaccggagg aaggcggtgg cggcgagcct     540
ggcggcgctg aagagcgccg gcgtggaggg gatcatggtg gacgtgtggt ggggcatcgt     600
ggagagcgag ggccccggcc ggtacaactt cgacggctac gtggagctca tggagatggc     660
ccgcaagacc ggcctcaagg tccaggccgt catgtcctcc accagtgcg gcggcaacgt      720 cggcgactcc gtcaacatcc gctcccgag gtgggtggtg gaggagatgg agaaggacaa     780
cgacctcgcc tacaccgacc aatggggacg ccgcaacttc gagtacatct ccctcggctg     840
cgacgccatg cccgtcttca agggccgcac gcccgtcgag tgctacaccg acttcatgcg     900
cgccttccgc gaccacttcg cctccttcct cggcgacacc atcgtcgaaa tccaagtcgg     960
catgggcccc gccggcgagc ttcggtaccc gtcctacccg gagagcaacg gcacctggag    1020
gttccccggc atcggcgcct tccaatgcaa cgacaggtac atgcgtagca gcctgaaggc    1080
ggcggcggag gcgaggggca agccggtagt ggggccacgg cgggccgacg gacgccggcg    1140
gctacaacaa ctggccggaa gacacggtgt tcttccgcgg cgactgcggc gggtggagca    1200
ccgagtacgg cgagttcttc ctgtcgtggt attcgcagat gctgctggag cacggcgagc    1260
gcgtgctgtc gggcgcgacg tccgtgttcg gcgacggcgc cggcgccaag atctcggtca    1320
aggtggccgg catccactgg cactacgcca cgcggtcgca cgcgccggag ctcacggcgg    1380
ggtactacaa cacgcggcac cgcgagcggc tacctcccga tcgcgcgcat gctggcgcgc    1440
cacggcgccg tgctcaactt cacctgcgtg gagatgcgcc accacgagca gccgcaggag    1500
gcgcagtgca tgcccgaggc gctcgtcagg caggtggccg ccgcggcgcg cgcggcgnga    1560
cgtcgggctc gccggggaga acgcgctgcc gcggtacgac ggcacggcgc acgaccaggt    1620
ggtcgccgcc gccgccgacc gcgcggcgaa ggaccggatg gtcgccttca cctacctccg    1680
gatgggcccc gacctcttcc acccggacaa ctggcgccgc ttcgtcgcct tcgtccgccg    1740
```

```
catgtccgag tccggctcgc cgcgggaggc cgccgagagc gccgcgcacg gcgtcgcgca    1800
ggccaccggc tcgctcgtgc acgaggccgc ggtcgcgctc cggagctagc accggtcaga    1860
cgctcatata caccgtcgcc tcgaggtcgg attccgatgt gggatcattc gatctccctt    1920 tttttttct tcttttgcc attttgtaca gccttttggg gagctttgga tttgtgcttt     1980
ttgtctcggg aggaaaaccg ctctggaggt cgaagagagc gtcattttcc tcccgttgaa    2040
gatcacgaat catttacgtt agagatgatg taattaagca gggaggggag gggaacacac    2100
acacactggc actcaaaagt tgttgtcacg cttggggaat atatccattt ccagccaaaa    2160
aaaaaacgca gaaatgcgtt gtgttcttgc gctctggttc gttgctgctg tgggtcagat    2220
tcagctggtg aaaaaactac agtactactg aaactgaaac tactagagcc tagagggaga    2280
ttaagctaag ttaattgcac gagtaattac tccacggttg tgtttagggt ctacgtcggc    2340
agattttgct ttctggtaga tccctaacct tatgtttgtt gggaattttta taaggagct    2400 aagtttgcct attgatttgc aatct                                          2425
```

<210> SEQ ID NO 25
<211> LENGTH: 3410
<212> TYPE: DNA
<213> ORGANISM: Oryza sativa
<220> FEATURE:
<221> NAME/KEY: misc_feature
<223> OTHER INFORMATION: TC83635 (PRO0009)

<400> SEQUENCE: 25

```
ccatggacac cgcctccgtc accggtggcg agcacaaggg gaaggagaag acgtgccggg     60
tgtgcggcga ggaggtggcg gcgagggagg acgggaagcc gttcgtggcg tgcgccgagt    120
gcggcttccc ggtgtgcaag ccctgctacg agtacgagcg cagcgagggc acccagtgct    180
gcccccagtg caacacccgc tacaagcgcc acaaggggtg cccacgggtg gaaggcgacg    240
aggacgacgg cggcgacatg gacgacttcg aggaggagtt ccagatcaag agccccacca    300
agcagaaacc cccccacgag cccgtcaact cgacgtctac tcggagaac ggcgagcagc    360 cggcacagaa gtggcgccct ggaggcccgg cgctctcttc cttcaccgga agcgtggctg    420
ggaaggatct ggagcaggag agggagatgg agggtggcat ggagtggaag gacaggatcg    480
acaagtggaa gacgaagcag gagaagcggg gcaagctcaa ccgcgacgac agcgacgacg    540
acgacgacaa gaacgacgac gagtacatgc tgctcgcgga ggcgaggcag ccgctgtgga    600
ggaaggtgcc gatcccgtcg agcaagatca acccgtaccg gatcgtgatc gtgctccggc    660
tggtggtgct ctgcttcttc ctcaagttcc ggatcacgac gccggcgatg gacgcggtgc    720
cgctgtggct ggcctcggtg atctgcgagc tgtggttcgc gctgtcgtgg atcctcgacc    780
agctgcccaa gtggtcgccg gtgacgaggg agacgtacct ggaccggctg gccctccggt    840
acgagcgcga cggcgagccg tgccgcctgg ccccgatcga tttcttcgtc agcacggtgg    900
acccgctcaa ggagccgccc atcatcaccg ccaacaccgt gctgtccatc ctcgccgtcg    960
actaccccgt cgaccgcgtc tcctgctacg tctccgacga cggcgcgtcc atgctgctct   1020
tcgacacgct ctccgagacc gccgagttcg cccgccggtg ggtcccctcc tgcaagaagt   1080
tcaccatcga gccccgcgcc cccgagttct acttctccca gaagatcgac tacctcaagg   1140
acaaggtcca gcccaccttc gtcaaagaac gccgcgccat gaagagagag tatgaggagt   1200
tcaaggtgag gataaacgcg ctggtggcga aggcgcagaa gaagccggag aagggtgggg   1260
tgatgcagga cgggacgcca tggccgggga acaacacgag ggaccacccg gggatgatcc   1320
```

-continued

```
aggtgtacct gggcagccag ggcgcgctcg acgtcgaggg cagcgagctg ccgcggctgg    1380
tgtacgtgtc ccgcgagaag cggcccggct acaaccacca caagaaggcc ggcgccatga    1440
actccctcgt tcgcgtctcc gccgtgctta ccaacgcccc cttcatcctc aacctcgact    1500
gcgaccacta cgtcaacaac agcaaggccg tccgcgaggc catgtgcttc ctcatggaca    1560
agcagctcgg caagaagctg tgctacgtcc agttcccca gcgcttcgac ggcatcgacc    1620
gccacgatcg ctacgccaac cgcaacaccg tcttcttcga catcaacatg aaggggctgg    1680
acgggataca ggggccggtg tacgtgggga cggggacggt gttcaacagg caggcgctgt    1740
acggatacga cccgccgcgg ccggagaaga ggccgaagat gacgtgcgac tgctggccgt    1800
cgtggtgctg ctgctgctgc tgcttcggcg gggggaagcg cggcaagtcg cacaagaaca    1860
agaagggcgg cggcggcggc gagggcggcg gcctcgacga gccgcgccgc gggctgctcg    1920
ggttctacaa gaagaggagc aagaaggaca agctcggcgg cggcgcggcg tcgctcgccg    1980
gagggaagaa agggtaccgg aagcaccagc gcgggttcga gctggaggag atcgaggagg    2040
gcctcgaggg gtacgacgag ctggagcgct cgtcgctcat gtcgcagaag agcttcgaga    2100
agcggttcgg ccagtcgccg gtgttcatcg cctccaccct cgtcgaggac ggcggcctcc    2160
cccagggcgc cgccgccgac cccgccgccc tcatcaagga ggccatccac gtcatcagct    2220
gcggctacga ggagaagacc gagtggggca aggagattgg gtggatctac gggtcggtga    2280
cggaggacat cttaacgggg ttcaagatgc attgccgtgg gtggaagtcg gtgtactgca    2340
cgccggcgag ggcggcattc aagggggtcgg cgcccatcaa cctgtcggat cgtctgcacc    2400
aggtgctccg gtgggcgctc ggctccgtcg agatcttcat gagccgccat tgcccgctct    2460
ggtaccctat ggcggccgcc tcaagtggct cgagcgcttc gcctacacca acaccatcgt    2520
ctaccccttc acctccattc ccctcctcgc ctactgcacc atccccgccg tctgcctcct    2580
caccggcaag ttcatcatcc ccacgcttaa caatttggcg agcatatggt tcatagcgct    2640
tttcctgtcg atcatcgcga cggggggtgct ggagctgcgg tggagcgggg tgagcatcga    2700
ggactggtgg aggaacgagc agttctgggt gatcggcggc gtgtcggcgc acctgttcgc    2760
cgtgttccaa ggcctcctca aggtgctcgg cggcgtggac accaacttca cggtgacgtc    2820
caaagccgcc gccgacgaag accgacgcgt tcggcgagct ctaactgttc aagtggacga    2880
cgctgctggt gccgccgacg acgctgatca tcatcaacat ggtggggatc gtcgccggcg    2940
tgtcggacgc cgtgaacaac gggtacgggt cgtggggccc gctgttcggg aagctcttct    3000
tctccttctg ggtcatcctc cacctctacc ccttcctcaa ggggctcatg gggaggcaga    3060
accggacgcc cacaattgtc gtgctctggt ccaacctcct cgcctccatc ttctccctcg    3120
tctgggtcag gatcgacccc ttcatcccca gcccaaggg ccccgtcctc aagccatgcg    3180
gggtctcgtg ctgagctgct gctgctactt ctctgtgtct ctgcattttg caagagggat    3240
gaccggatgg atgattcttg ttgtatggag tattttgact tgttcatgta caagttttg    3300 tgagtgggat aaaagtgttt tggggggtaaa atttgtaaga actgaggtgg agattatact    3360
cgaatttaag aacaattgtt tttgaatttt cttttaagat ttttgggagt              3410
```

<210> SEQ ID NO 26
<211> LENGTH: 602
<212> TYPE: DNA
<213> ORGANISM: Oryza sativa
<220> FEATURE:
<221> NAME/KEY: misc_feature
<223> OTHER INFORMATION: TC83117 (PRO0058)

<400> SEQUENCE: 26

```
cccccccctc gaggttcgac ccactcgtcc gctgacggtt agttccaagg gaaagaagaa      60
atggaggctt cacgcaaggt gttctcggcc atgcttctca tggtgctgct gcttgcagcc     120
actggtgaga tgggcgggcc ggtgatggtg cggaggctc ggacgtgcga gtcgcagagc      180
caccggttca agggcccgtg cgcccgcaag gcgaactgcg ccagcgtatg caacacggag     240
ggcttccccg acggctactg ccacggcgtc cgccgccgct gcatgtgcac caagccctgc     300
ccctgatcga tgaaccagca gctagcgcag cagcttgtgc cgccacctcg cgcatgtgtc     360
atcgtgtcga tcgatcggat cctagctgcc ctatgaatga ataaaagtgt gtggcttatg     420
cgtggttttc tcttggagaa ctttggcttt tgtggtgtta agttcgatcg ttttgtgcat     480
ccaccatcca tccatcctcc cattctgctt gttctaaggt tatactacta cttgagaagg     540
tgatgcaatt gtgctcaaca gtttattaat acttcatccg ttttaaaatg tttgaccccg     600
tt                                                                    602
```

<210> SEQ ID NO 27
<211> LENGTH: 1170
<212> TYPE: DNA
<213> ORGANISM: Oryza sativa
<220> FEATURE:
<221> NAME/KEY: misc_feature
<223> OTHER INFORMATION: TC89913 (PRO0061)
<220> FEATURE:
<221> NAME/KEY: misc_feature
<222> LOCATION: (15)..(16)
<223> OTHER INFORMATION: n = any nucleotide
<220> FEATURE:
<221> NAME/KEY: misc_feature
<222> LOCATION: (1162)..(1162)
<223> OTHER INFORMATION: n = any nucleotide

<400> SEQUENCE: 27

```
aattcggcac gagannaaaa ggaaaaaaaa acaaaacaca ccaagccaaa taaaagcgac      60
aatgggatcg ctcaccacca acatcgtcct cgccgtcgcc gtggtggcag cgctggtcgg     120
cggcgggtcg tgcggcccgc ccaaggtgcc accggcccg aacatcacga ccaactacaa      180
cgccccgtgg ctccccgcca gggccacctg gtacggccag ccctacggct ccggctccac     240
cgacaatggt ggcgcgtgcg ggatcaagaa cgtcaacctg cctccctaca cggcatgat      300
ctcctgcggc aacgtcccaa tcttcaagga cggcagggga tgcggctcat gctacgaggt     360
gaagtgtgag cagccggcgg cgtgctcgaa gcagccggtg acggtgttca tcacggacat     420
gaactacgag cccatctcgg cgtaccactt cgacttctcc ggcaaggcgt tcggcgccat     480
ggcttgcccg gggaaggaga ccgagctccg caaggccggc atcatcgaca tgcagttcag     540
gagggtgcgc tgcaagtacc ccggcggcca gaaggtcacc ttccacgtcg agaagggctc     600
caacccaac tacctcgccg tgctcgtcaa gttcgtcgcc gacgacgtg acgtcatcca       660
gatggacctc caggaggccg gattgccagc gtggaggccc atgaagctgt cgtggggcgc     720
catctggagg atggacaccg ccacgccact caaggcaccc ttctccattc gcgtcaccac     780
cgagtccggc aagagcctca tcgccaaaga cgtcatcccg gtcaactgga tgccagacgc     840
catctacgta tcaaacgtcc agttctattg agatcggacg gaaacgatcc tcctaattta     900
tttccctatt aatttgttca aatggtttcc ttctataacc tatatttttc ccgttgttag     960
aaatggttcc atttcctcct acagcttact ttaagatagt tgcgcttgta tatctgcgcc    1020
atcttgtaag ttgtaagatg ctgaagaaca ctatgaattc tgagcatctg attctccggg    1080
```

```
aagatttact atgataaaca acagtttgat ttactatgtg tgtcccttg tttattgtat    1140 gctatcctaa tacttatgaa angttttgat                                    1170

<210> SEQ ID NO 28
<211> LENGTH: 861
<212> TYPE: DNA
<213> ORGANISM: Oryza sativa
<220> FEATURE:
<221> NAME/KEY: misc_feature
<223> OTHER INFORMATION: TC89985

<400> SEQUENCE: 28
ccacgcgtcc gcccacgcgt ccgcgatcag cagcagcagc agcttgcaca ctcgagctta     60
gcttagcttt tgcaagagag atcgagctag agatggagaa gtcgagcaag atgatggcgg    120
tggcggcggt gctggtgctc gcggtggtcg gcgcggcgga ggcgaggaac atcaaggcgg    180
cggcggcggc ggcggcggag agcaaggaca cggtggtgca gccgacgacg ttcccgccgt    240
tcgaccgctt cgggagcgcg gtgccggcgt tcggcggcat gcccggcagc agcatcccgg    300
ggttcagcct ccccggcagc agcggctcca ccccggcgg cctcggcggc ttcggcagca    360
tgcccatgtt cggcggcctc ggcggcggct cacctggcct cggcggcggc atgcccggct    420
cccccgccgc cgccgacaag caggccaaga agccatgaga gacctcgccg tcgcggcgg    480 cgtcgccgct gctgcgcggg taatgtgctc tatgtagcgc acggcgttgc atgcaatatg    540
gatggctata tgacgcgcgc gcgttatatc ttcatatgtg cagttagctt gcactgtgtc    600
tagctagcgt tctattatga gtagtgtctc ttctatctct tttctttaca tgcatttgga    660
ggaggattat tctatctgtt tgttggttgg ttgtgtttgt ttgtttttaat taggtcccctt    720 cttatatttt gtgttttaat taagttcgtg atcatgtagt agtactacca ctgtttcgag    780
ctcgaggcat gaataatgct aaatgtgatc attattgtgt tattgtatgg tgatggctat    840
atatattact atctctgctt c                                              861

<210> SEQ ID NO 29
<211> LENGTH: 1252
<212> TYPE: DNA
<213> ORGANISM: Oryza sativa
<220> FEATURE:
<221> NAME/KEY: misc_feature
<223> OTHER INFORMATION: TC89891 (PRO0081)
<220> FEATURE:
<221> NAME/KEY: misc_feature
<222> LOCATION: (5)..(5)
<223> OTHER INFORMATION: n = any nucleotide

<400> SEQUENCE: 29
cccangcgtc cgaaccaatc gactcgcacc accaccagca gctcaagcag caacagctca     60
aacggaggaa gatctcatcg ccatgacgac cggcaatggc gacgcaccgg tgatcaagaa    120
cgcccacagc gacatcgaca gcaccaacaa gacgctgctc aagagcgacg ccctgtacaa    180
gtatgtcctg gacacgacgg tgctgccacg ggagccggag tgcatgcgcg atctgcgcct    240
catcacggac aagcaccagt gggggttcat gcagtcgtcg gcggatgagg cgcagtgctg    300
gggatgctgc tgaagatggc cggagcgaag aggacaatcg aggtgggtgt cttcaccggc    360
tactcgctgc tggcgacggc gctggcgctg ccggaggacg ggaaggtggt ggcgatcgac    420
ccggacaggg agagctacga gatcgggcgg ccgttcttgg agaaggccgg ggtggcgcac    480
aaggtggact ccgcgagggg aaggggctg gagaagctgg acgagctgct cgccgaggag    540
gcggcggcgg ggcgcgaggc ggcgttcgac ttcgcgttcg tggacgcgga caagcccaac    600
```

```
tacgtcaagt accacgagca gctgctgcag ctggtgcgcg tcggcgggca catcgtgtac      660
gacaacacgc tgtgggccgg cacggtggcg ctgccgccgg acacgccgct gtcggacctg      720
gaccggaggt tctccgtcgc catcagggac ctcaactcca ggctcgccgc cgacccgcgc      780
atcgacgtct gccagctcgc catcgccgac ggcatcacca tctgccgccg cctcgtgtga      840
ggtcgagacc gagaccttac cggccgatcc atccatcgct ctcgcgtgat taattaacgt      900
gtgttgctgt actcttctac tgctacaact atactattac ttccttaatt gccgcttaaa      960
ttttcctata cgtgtttcaa tcaatgagat tattatattc ttcgagcatg agagagacgg     1020
agttgtaggg acatttgatg atggttgtta ctgtactaca tgttgataag tgcaacatct     1080 cttccatgg ttgctactct actcaccgtg tcatgttggt tgcggatttt gatctcatct     1140
gcaagatgga ctactggggc ccaaaatgga acagactggt ccctcgatcc tgcaggagct     1200
tgcacctgtt gcaagggcct ttttaactgg ctaactaggt gggtaagtag gg             1252
```

<210> SEQ ID NO 30
<211> LENGTH: 671
<212> TYPE: DNA
<213> ORGANISM: Oryza sativa
<220> FEATURE:
<221> NAME/KEY: misc_feature
<223> OTHER INFORMATION: TC89670 (PRO0091)
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (14)..(14)
<223> OTHER INFORMATION: n = any nucleotide

<400> SEQUENCE: 30

```
gcnggcttcg gcangagttc aaacattata gttgaagcat agtagtagaa tcctacaaaa       60
atgaagatca ttttcgtatt tgctctcctt gctattgttg catgcaacgc ttctgcacgg      120
tttgatgctc ttagtcaaag ttatagacaa tatcaactac aatcgcatct cctgctacag      180
caacaagtgc tcagcccatg cagtgagttc gtaaggcaac agcatagcat agtggcaacc      240
cccttctggc aaccagctac gtttcaattg ataaacaacc aagtcatgca gcaacagtgt      300
tgccaacagc tcaggctggt agcgcaacaa tctcactacc aggccattag tagcgttcag      360
gcgattgtgc agcaactaca gctgcagcag gtcggtgttg tctactttga tcagactcaa      420
gctcaagctc aagctttgct ggccttaaac ttgccatcca tatgtggtat ctatcctaac      480
tactacattg ctccgaggag cattcccacc gttggtggtg tctggtactg aattgtaata      540
gtataatggt tcaaatgtta aaataaagt catgcatcat catgcgtgac agttgaaact      600
tgatgtcata taaatctaaa taaaatcacc tatttaaata gcattcatgt atgagttcca      660
ttatcatagc t                                                          671
```

<210> SEQ ID NO 31
<211> LENGTH: 436
<212> TYPE: DNA
<213> ORGANISM: Oryza sativa
<220> FEATURE:
<221> NAME/KEY: misc_feature
<223> OTHER INFORMATION: TC89883 (PRO0095)

<400> SEQUENCE: 31

```
cctcgagggt cgacccacgc gtccgctctc ctctcttctc tcgccctcac cgctcgccga       60
```

| | | | |
|---|---|---|---|
| ggttgccgtc | tccttgtctc | ctccgctcct tgcgccgccg ccgcgacgag tcgcggggag | 120 |
| gggcggcgat | ctccatctcc | atctgaggcg aggagagcag gggaggtgag gggatcctgg | 180 |
| tgaggtttgt | gattactgga | caatagaaat atttacacaa tatggctggc ggctctgctg | 240 |
| atgcagtgac | caaggagatg | gaggcgctac tcgttggaca aaatccaaat gcggttagtg | 300 |
| gagaaacatg | cgagacctca | tcaaagaag gcaaagttgc agatagcaat ggatctcatt | 360 |
| cttcaccacc | agaagatgat | gatgatgaag cgcaagggga tggtccatct caagattgga | 420 |
| ggatccagaa | gctttc | | 436 |

<210> SEQ ID NO 32
<211> LENGTH: 860
<212> TYPE: DNA
<213> ORGANISM: Oryza sativa
<220> FEATURE:
<221> NAME/KEY: misc_feature
<223> OTHER INFORMATION: TC90434 (PRO0111)
<220> FEATURE:
<221> NAME/KEY: misc_feature
<222> LOCATION: (1)..(1)
<223> OTHER INFORMATION: n = any nulceotide
<220> FEATURE:
<221> NAME/KEY: misc_feature
<222> LOCATION: (10)..(10)
<223> OTHER INFORMATION: n = any nulceotide

<400> SEQUENCE: 32

| | | | |
|---|---|---|---|
| nagggctaan | attaccggag | tatttttgca aagggagtaa tcaaagttcc aatacgaaat | 60 |
| cgcggtcgta | gtagtacaat | acaaagacga gttcacggag cgcgtaaact aataaggaaa | 120 |
| aattaaacgt | cgcggagaaa | taatagccga actggatgaa gatgagcagc actgcctctt | 180 |
| gcctagccta | gccatcatg | gcgaggccga cggccccgac cagcaggccc atcaccgaac | 240 |
| gggcctcgct | gccgctggcc | cgccggtgc tgcccgtcga cttcgtcgtc gtcgtcgtcg | 300 |
| gcgtcgtggt | cgcgtccggc | gtcgacgagg gcgtgtccat gccggggtcc gatgacggcg | 360 |
| tggcgggcgt | cgcggtggac | ggcggggacg acgacgccgt cggggtgggg gtggtgccgg | 420 |
| ccgccgcgga | gaccgtgacg | gcgagcttca tgccgccgga gcagtggccg ctggtgccgc | 480 |
| agatgaagta | gcgggtgccg | ggcttggtga gcgcgatctt ggtgttctgg tcgctgtagg | 540 |
| actggatcga | gttgctggcg | gacacgcgct gtagtcagcc gagctcacct ccgccaccgt | 600 |
| gtgcatcatg | ctgtactgga | acacgagcga gtcaccaacg ctgaaggttt tgctcttcgc | 660 |
| ccaggtatcg | tagtccacgc | cactgctcca gccggatgtg tcgccgacgg tgtagtccac | 720 |
| ggcgaaagcc | ggcgcaacgg | cggcgaggag tagcaccacc agacctgcag ctgcaagtcc | 780 |
| atgtactcca | gccatgatgg | cagagttaat tagcaaacgc gaactgatta gagccgtact | 840 |
| agtactggtg | gccctcgtgc | | 860 |

<210> SEQ ID NO 33
<211> LENGTH: 1167
<212> TYPE: DNA
<213> ORGANISM: Oryza sativa
<220> FEATURE:
<221> NAME/KEY: misc_feature
<223> OTHER INFORMATION: TC83072 (PRO0116)

<400> SEQUENCE: 33

| | | | |
|---|---|---|---|
| aggaaaagaa | gaaaaaagat | cctgtgaacc ctacgaaact accgaagcga acggaaggca | 60 |
| ggaatcggcg | gcggcggcgg | cggcggcggt ggggagaagc catggagcgg ctgcagcgga | 120 |
| tcttcggcgc | ctccggcatg | gggcagccgc cgtcggactc gccgctgctc gactcctccg | 180 |

-continued

```
agcaggtcta catctcctcc ctcgccctcc tcaagatgct caagcacggg agggccggcg      240
tgccgatgga ggtgatgggg ctgatgctgg gggagttcgt cgacgactac acggtcaggg      300
tggtcgacgt cttcgccatg ccgcagagcg ggaccgggt cagcgtcgag gccgtcgacc       360
atgtcttcca gaccaacatg ctcgacatgc tcaagcagac cgggaggcca gaaatggtgg      420
taggttggta ccattcccat cctggatttg gttgctggct tcaggagtt gacatcaata       480 ctcaacagag ttttgaagct ttaaacccca gggcagttgc cgtcgtgata gatcccatcc      540
aaagtgtcaa ggggaaagtt gtcattgatg catttcgcct tattaaccct cagaccatga      600
tgcttggtca ggagccacga cagacaacat caaatgttgg gcacctaaat aagccatcta     660
ttcaggctct tattcatggg ctgaacaggc actactattc aattgcaatc aattaccgga     720
aaaatgagct tgaggaaaag atgttactga acttgcacaa aaagaaatgg accgatggat     780
tgattctgaa gaggtttgac actcattcaa agaccaatga gcagactgtt caggaaatgc    840
tgaaccttgc tatcaagtac aacaaggcgg tgcaagagga ggatgagctg ccgcctgaga    900
aattagcgat agcaaatgtg ggacggcaag atgctaagaa gcacttggaa gagcatgtct    960
ccaatttgat gtcatcaaac atagttcaga cgctaggaac catgctcgat acagttgtat   1020
tttagatcac tactgctgtt atcccaacac tgtacccaga gctcgtttat tttttatttt   1080
tttatgttta tcgaagccta ccataattca gtgaacttaa cgccagttac atttgggtta   1140
tgaaagctta ccacttgaca acttcat                                        1167
```

<210> SEQ ID NO 34
<211> LENGTH: 871
<212> TYPE: DNA
<213> ORGANISM: Oryza sativa
<220> FEATURE:
<221> NAME/KEY: misc_feature
<223> OTHER INFORMATION: TC90038 (PRO0117)

<400> SEQUENCE: 34

```
cctagctcct cccgccgccg ccgccgccgc cgccgccgcc tctccactcg agagacccag      60
ccgccgccgc cgccgccgcc gccatgtcgc tgatcgccgg ggaggacttc cagcacatcc     120
tgcgtctgct gaacaccaac gtcgatggga agcagaagat catgttcgcg ctcacctcca     180
tcaagggtgt cggccgcagg ttctccaaca tcgcctgcaa gaaggccgac atcgacatga    240
acaagagggc cggtgagctt acgcggagg agctggagcg gctgatgacc gtggtggcga    300
acccgcggca gttcaaggtg cccgactggt tcctcaacag gaagaaggac tacaaggacg    360
ggaggttctc ccaggttgtc tccaacgcgc tcgacatgaa gctcagggat gatcttgaga    420
ggctcaagaa gatcaggaac caccgtggtc tgaggcacta ctggggcctc cgtgtgcgtg    480
ggcagcacac caagacaacc ggaaggaggg gtaagactgt cggtgtgtcc aagaagcgat    540
aagcctaaga accacccgag acttgatgaa gcgtttcgtt gggtgatgtt ttgccctagg    600
ataatatttt gcagctatgg aaccttgtcg taatgtatct tgaagagtgt ctttgggaac    660
taagagtaat ttacttttct tgaaactatt gcagtattga ctccttgttt attgcttttc   720
tccactttct tctacccact taaaactatt gcagtatcga ctccttgttt attgctattc   780
tccactggct tctgccttaa ttttggatgt tgcatgcgct gtgtatctgg ttcatgtgat   840
gtacccatgg cagctttgat gcattgggat t                                   871
```

<210> SEQ ID NO 35
<211> LENGTH: 1245

<212> TYPE: DNA
<213> ORGANISM: Oryza sativa
<220> FEATURE:
<221> NAME/KEY: misc_feature
<223> OTHER INFORMATION: TC82936 (PRO0122)

<400> SEQUENCE: 35

```
acgcggccaa aacgtaccct tgtgactaca cccgcttcgc ttcctcccct ctctaagccg      60
gggaagctaa gccatggcgt ccgtcaccgc ccgcaccccg gtcgcagccc tccgctcgtc     120
ggcgtcgctc aagtctacct tcctagggca atcctccacc cgcctcgccc gcgcaccgac     180
tacgaggcgt aatgttcggg cggaggccaa gggagagtgg ctccccggcc tcccttctcc     240
cacctacctc aacggcagct tgccaggcga taacgggttc gacccgttgg gtctggcgga     300
ggacccggag aacctgcggt ggttcgtgca ggcgagtgg tgaacgggcg gtgggcgatg      360
ctggggggtgg ccgggatgct gctgcctgag gtgctgacga agatcgggtt gatcgacgcg    420
ccgcagtggt acgacgccgg caaggccacc tacttcgcgt cgtcgtcgac gctgttcgtc     480
atcgagttca tcctgttcca ctacgtggag atccggcggt ggcaggacat caagaaccct    540
ggctgcgtca accaggaccc catcttcaag agctacagcc tcccgccgca cgagtgcggc    600
taccccggca gcgtcttcaa cccctcaac ttcgagccca ccctcgaggc caaggagaag      660
gagctcgcca acgggaggct ggcgatgctg gcgttcttgg ggttcctggt gcagcacaac    720
gtgacgcaga aggggccctt cgacaacctg ctgcagcacc tgtctgaccc gtggcacaac    780
accatcatcc agacgctgtc aggctgagcg tgtgatcgat ttcatcaggg ccagggcatc    840
tcaaggagct tgatgagttc aggctggtga aaccgatgat tgggcgatgg aagatgttct     900
cttcttgttt cttcttttt tttttgtgga gtatgcatgt ataagatgtt aatgaattgg      960
ggggaggaga gagagagaga tggatgtgat gagattcaga cttactgtgt gtgttgtggt    1020
aattgtttcc tgcatgcatg gatctggatg catgggtgag ggggtgagtt gagtggtgaa    1080
tttctgatgt acagtactac aggggggataa actatctcat ggtagcagca gtgttctagc    1140
tatctcatgg tctcgatctt aattatggtg gataaactac gcttaattgc ttgtcaagtg    1200
cttcatttgc gcattgattc agtattgcgt atcgattcaa agacc                    1245
```

<210> SEQ ID NO 36
<211> LENGTH: 1416
<212> TYPE: DNA
<213> ORGANISM: Oryza sativa
<220> FEATURE:
<221> NAME/KEY: misc_feature
<223> OTHER INFORMATION: TC89839 (PRO0123)

<400> SEQUENCE: 36

```
cccacgcgtc cgcccacgcg tccgggacac cagaaacata gtacacttga gctcactcca      60
aactcaaaca ctcacaccaa tggctctcca agttcaggcc gcactcctgc cctctgctct     120
ctctgtcccc aagaagggta acttgagcgc ggtggtgaag gagccggggt tccttagcgt     180
gagcagaagg ccaagaagcc gtcgctggtg gtgagggcgg tggcgacgcg gcgggccggt     240
ggcgagcccc ggcgcgggca cgtcgaaggc ggacgggaag aagacgctgc ggcagggggt    300
ggtggtgatc accggcgcgt cgtcgggggct cgggctcgcg gcggcgaagg cgcttggcgg    360
agacggggaa gtggcacgtg gtgatggcgt tccgcgactt cctgaaggc ggcgacggcg      420
gcgaaggcgg cggggatggc ggcgggagc tacaccgtca tgcacctgga cctcgcctcc    480
ctcgacagcg tccgccagtt cgtggacaac ttccggcgct ccggcatgcc gctcgacgcg    540
```

```
ctggtgtgca acgccgcaca tctaccggcc gacggcgcgg caaccgacgt tcaacgccga      600
cgggtacgag atgagcgtcg gggtgaacca cctgggccac ttcctcctcg cccgcctcat      660
gctcgacgac ctcaagaaat ccgactaccc gtcgcggcgg ctcatcatcc tcggctccat      720
caccggcaac accaacacct tcgccggcaa cgtccctccc aaggccgggc taggcgacct      780 ccggggctc gccggcgggc tccgcggca gaacgggtcg gcgatgatcg acggcgcgga       840
gagcttcgac ggcgccaagg cgtacaagga cagcaagatc tgtaacatgc tgacgatgca      900
ggagttccac cggagattcc acgaggagac cgggatcacg ttcgcgtcgc tgtacccggg      960
gtgcatcgcg acgacgggct tgttccgcga gcacatcccg ctgttccggc tgctgttccc     1020
gccgttccag cggttcgtga cgaaggggtt cgtgtcggag gcggagtccg ggaagcggct     1080
ggcgcaggtg gtgggcgacc cgagcctgac caagtccggc gtgtactgga gctgaacaa     1140 ggactcggcg tcgttcgaga accagctctc gcaggaggcc agcgacccgg agaaggccag     1200
gaagctctgg gacctcagcg agaagctcgt cggcctcgtc tgagtttatt atttacccat     1260
tcgtttcaac tgttaatttc ttcggggttt aggggggttt agcttcagt gagagaggcc      1320 tgtcaagtga tgtacaatta gtaattttt tttacccgac aaatcatgca ataaaaccac     1380
aggcttacat tatcgatttg tccacctaaa ttaagt                                1416

<210> SEQ ID NO 37
<211> LENGTH: 1149
<212> TYPE: DNA
<213> ORGANISM: Oryza sativa
<220> FEATURE:
<221> NAME/KEY: misc_feature
<223> OTHER INFORMATION: TC85888 (PRO0133)

<400> SEQUENCE: 37
cttctacttc tatcatacca aacaaactag cttaatttgc attgcatcac attgccggcc       60
gccatgagag ctctcgctct cgcggtggtg gccatggcgg tggtggccgt gcgcggcgag      120
cagtgcggca gccaggccgg cggcgcgctc tgccccaact gcctctgctg cagccagtac      180
ggctggtgcg gctccacctc cgattactgc ggcgccggct gccagagcca gtgctccggc      240
ggctgcggcg gcggcccgac cccgccctcc agcggtggcg gcagcggcgt cgcctccatc      300
atatcgccct cgctcttcga ccagatgctg ctccaccgca acgaccaggc gtgcgccgct      360
aagggcttct acacctacga cgccttcgtc gccgccgcca acgcctaccc ggacttcgcc      420
accacccgcg acgccgacac ctgcaagcgc gaggtcgccg ccttcctggc gcagacgtcc      480
cacgagacca ccggcggctg gcccacggcg cccgacggcc cctactcctg gggctactgc      540
ttcaaggagg agaacaacgg caacgccccc acatactgcg agcccaagcc ggagtggccg      600
tgcgccgccg cgaagaagta ctacggccgg ggacccatcc agatcaccta caactacaac      660 tacgccgcg gggcaggcat cggctccgac ctgctcaaca cccgacct ggtgcgtcg       720 gacgccagtc tccttcaaga cggcgttctg gttctggatg acgccgcagt cgcccaagcc      780
gtcgtgccac gcggtgatca ccggccagtg gacgccgtcc gccgacgacc aggcggcggg      840
gcgcgttccg ggctacggcg agatcaccaa catcatcaac ggcggtgtgg agtgcgggca      900
cggcgcggac gacaaggtgg ccgaccggat cgggttctac aagcgctact gcgacatgct      960
gggcgtcagc tatggcgata acctggattg ctacaaccag aggccctacc cgccttccta     1020
gttgatattt gatccgagca gacgaataaa atacaatgca cacgagattg tgagactcga     1080
gaaaacatat actacctctg aattttaata catatctcta aacaaaaaaa aaaaaaaaaa     1140
```

```
aaaatatac                                                            1149

<210> SEQ ID NO 38
<211> LENGTH: 981
<212> TYPE: DNA
<213> ORGANISM: Oryza sativa
<220> FEATURE:
<221> NAME/KEY: misc_feature
<223> OTHER INFORMATION: TC84300 (PRO0151)

<400> SEQUENCE: 38
aagaggcaag agcatccgta ttaaccagcc ttttgagact tgagagtgtg tgtgactcga    60
tccagcgtag tttcagttcg tgtgttggtg agtgattcca gccaagtttg cgatggcttc   120
tcagcaggaa cgggctagct accacgccgg cgagaccaag gcccgcgccg aggagaagac   180
ggggcgcatg atgggcacgg cgcaggagaa ggcgcgggag gccaaggaca cggcgtccga   240
cgccgcgggg cgcgcgatgg gcaggggaca cggcgccaag gaggcgacca aggagaaggc   300
gtacgagacc aaggacgcga ccaaggagaa ggcgtacgag gcaaaggacg cggcctccga   360
cgccaccggc cgcgccatgg acaagggccg cggcgccgcg ggcgccacga gggacaaggc   420
gtacgatgcc aaggacaggg cggctgacac ggcgcagtcc gccgccgacc gcgcccgcga   480
cggcgccggg cagaccggga gctacattgg acagaccgcc gaggccgcca agcagaaagc   540
ggccggcgcc gcgcagtacg ccaaggagac cgcgatcgcc ggcaaggaca agaccggcgc   600
cgtgctccag caggcagggg agcaggtgaa gagcgtggcg gtgggggcga aggacgcggt   660
gatgtacacg ctcgggatgt caggcgataa caagaacaac gccgctgccg gcaaggacac   720
cagcacctac aagcctggaa ctgggagtga ctaccagtaa tacggtagaa gaagcatgtg   780
tcgtctttgg cactgatgcc aaagtgtacg tgttgtatcc tcttttttaa gtttcagctc   840
gacttcgacg tgttcggtgt cacactttgg tttttcagtt gtgctcaact gttcatgttt   900
ctggttccat ggagggccag tgtggaggtc aatgtttaag ctttcgtttt aaaatctgat   960
aataaagttg gttaagacct g                                             981

<210> SEQ ID NO 39
<211> LENGTH: 1203
<212> TYPE: DNA
<213> ORGANISM: Oryza sativa
<220> FEATURE:
<221> NAME/KEY: misc_feature
<223> OTHER INFORMATION: TC89687 (PRO0169)

<400> SEQUENCE: 39
tactcctctc tctcacctcc accatctagc tcactcacac agtctccact cacacgcatt    60
gcagaggaga ggcgacaatg gaggggaagg aggaggacgt gcggctgggg gcgaacaggt   120
actcggagag gcagccgata gggacggcgg cgcagggcgc gggggacgac aaggactaca   180
aggagccgcc gccgggccgc tgttcgagcc aggggagctc aagtcgtggt ctttctaccg   240
ggccgggatc gccgagttcg tcgccaccct cctcttcctc tacatcacca tcctcaccgt   300
catgggggtc tccaagtcct cctccaagtg cgccaccgtc ggcatccagg gcatcgcctg   360
gtccttcgga ggcatgatct tcgcgctcgt ctactgcacc gccggcatct ccggaggaca   420
catcaacccca gcagttactt ttgggctgtt cttggccagg aagctgtccc tgacccgggc   480
catcttctac atagtgatgc aatgcctagg ggccatctgc ggagctggag ttgtgaaggg   540
cttccagcag ggtctgtaca tgggcaatgg cggtggtgcc aatgtagttg ccagtggcta   600
caccaagggt gacggtcttg gtgctgagat tgttggcacc ttcatcctgg tctacaccgt   660
```

```
cttctcagcc actgatgcca agaggaatgc cagggactca catgttccta tccttgcccc     720
actgccaatt ggttttgcgg tgttcctggt ccacctggcc accatcccca tcaccggtac     780
tggcatcaac ccagccagga gccttggcgc tgccatcatc tacaacaagg accatgcctg     840
gaatgaccat tggatcttct gggttggtcc cttcgttggc gctgccctgg ctgccatcta     900
ccaccaggtg atcatcaggg cgatcccatt caagagcagg tcttaagccc cgcgccgccg     960
ctgcgcagcc gacgacatgc aacgcaatcg tgatgtcctg tttcccgcgc gctactgctg    1020
cgcatctgtc gattccctct atctctagtc cccaagatgt ttttcctatc tgaaccctga    1080
acaactcaat cgtgtaatcc agtactcagt cactgtatgt ttttatgtga tggagatctt    1140
aattcttaag ttatcatctc tgttgctgga aatccggttt cctcttcgtg catgaaccgc    1200
gcc                                                                  1203

<210> SEQ ID NO 40
<211> LENGTH: 964
<212> TYPE: DNA
<213> ORGANISM: Oryza sativa
<220> FEATURE:
<221> NAME/KEY: misc_feature
<223> OTHER INFORMATION: TC89846 (PRO0170)

<400> SEQUENCE: 40
cccacggttc cgcccacggt ccgcccacgg tccgcttctc ttctctggtg gtgtgggtgt      60
gtccctgtct cccctctcct tcctcctctc ctttccctc ctctcttccc ccctctcaca     120
agagagagag cgccagactc tccccaggtg aggattcagc catgaagggg gccaaatcca     180
agggcgccgc caagcccgac gccaagttgg ctgtgaagag taaggcgcg gagaagcccg     240 ccgccaaggg caggaagggg aaggccggca aggaccccaa caagcccaag agggctccct     300
ccgctttctt cgttttatg gaggagttcc gtaaggagtt caaggagaag accccaaga     360 ataaatctgt cgctgctgta ggaaaagcag ccggtgatag gtggaaatcc ctgaccgaag     420
cggacaaggt ccctatgta gccaaggcca acaagctcaa ggccgagtac aacaaggcca     480
ttgctgccta caacaagggc gagagcactg ccaagaaggc cccgccaag gaggaagagg     540 aggacgacga ggaggaatct gacaagtcca agtccgaggt caatgatgag gatgacgacg     600
agggcagcga agaggatgaa gacgatgacg agtgagcctt ccagtggaca agatgggagc     660
agcaagacgc taagggcggc gggcgtccta aggagcctat ccatcatcat catcgtctac     720
tagaattatt cagtttcact tcacatcgtg atgtttact ttttctctcg tcctataacg     780
gatagcgctc cttgttggcg ccactggtgg gtgttgtggt gcagccaatg tcttgtctcc     840
accgtcaatg atccgcttgt acctagatta ctctttccat tgtcatcggc taacattgtg     900
ataatatcag tttgcgtatg ttagattaaa ttgtttctaa ttccgtcgtt ttcttcttcc     960
ttgc                                                                 964

<210> SEQ ID NO 41
<211> LENGTH: 1542
<212> TYPE: DNA
<213> ORGANISM: Oryza sativa
<220> FEATURE:
<221> NAME/KEY: misc_feature
<223> OTHER INFORMATION: TC82935 (PRO0171)

<400> SEQUENCE: 41
cacacctcac acctcaccac catcacctcc tcctcctcct cctcttcctc cgcgcgcgcg      60
```

```
agatccaggg agagggagag ggagagatca tggcggggac ggtgacggtg ccgtcggcgt      120
cggtgccgtc gacgccgctg ctcaaggacg agctggacat cgtgatcccg acgatccgca      180
acctggactt cctggagatg tggcggccct tcttccagcc ctaccacctc atcatcgtgc      240
aggacggcga cccgaccaag accatccgcg tccccgaggg cttcgactac gagctctaca      300
accgcaacga catcaaccgg atcctcggcc caaggcctc ctgcatctcc ttcaaggact       360
ccgcatgccg ctgcttcggc tacatggtct ccaagaagaa gtacgtcttc accatcgacg      420
acgactgctt cgttgccaag gacccatctg gcaaggacat caatgctctt gagcagcaca      480
tcaagaacct cctcagcccg tccaccccgt tcttcttcaa caccttgtat gatccctacc      540
gcgaaggcgc tgactttgtc cgtggttacc ccttcagcct cagggaggga gccaagactg      600
ctgtctctca cggcctgtgg cttaacatcc ctgactatga tgctcctact cagatggtca      660
agcctcgtga gaggaactcc aggtatgttg atgctgtcat gactgtgccc aagggaacct      720
tgttccccat gtgtggcatg aaccttgctt ttgaccgtga tctcatcggt cctgcaatgt      780
actttggtct catgggtgat ggccagccta ttggtcgcta cgacgacatg tgggctggat      840
ggtgcatgaa ggtcatctgt gaccacctga gcctgggagt gaagactgga ctgccgtaca      900
tctggcacag caaggctagc aaccccttcg tgaacttgaa gaaggaatac aagggcatct      960
tctggcagga ggacatcatc cccttcttcc agaacgccac catccccaag gagtgcgaca     1020
ccgtccagaa gtgctacctc tccctcgccg agcaggtcag ggagaagctc ggcaagatcg     1080 accccctactt cgtcaagctt gccgatgcca tggtcacctg gatcgaggcc tgggatgagc    1140
tgaacccctc gactgctgct gtcgagaacg gcaaggccaa gtagattgat cctgggagct     1200
tgtgtgtcgc aggatggaaa gtacccttta agtgaaagtg ttgctgtggc ctaggccccc     1260
tagatatagc tcttttgag atgaagggag agattactta agcaacttta taattctttg     1320
ttgttatgct ggttctttg tagctggaaa aggatttgtt atcatcgttt acataattca     1380
agacaataat aattttatca tgtaattttg atagtcgtgc tttggttgct aaatggtgtt     1440
attgtattta ataaccttttg caaatcacta tacctgttgg ttgttctgag aattgtatgc     1500
actaccatat tatatttcta aatcatttcg taggcattat gg                        1542
```

<210> SEQ ID NO 42
<211> LENGTH: 1432
<212> TYPE: DNA
<213> ORGANISM: Oryza sativa
<220> FEATURE:
<221> NAME/KEY: misc_feature
<223> OTHER INFORMATION: TC82977 (PRO0173)
<220> FEATURE:
<221> NAME/KEY: misc_feature
<222> LOCATION: (1429)..(1429)
<223> OTHER INFORMATION: n = any nucleotide

<400> SEQUENCE: 42

```
aaaagagcag cgtcgcctct cctcctccct aacccctacg cttccagaac cttctcgaag       60
ctcccgctcc cccccccctt ccgctccaat ggcgaaggaa ccgatgcgcg tgctcgtcac      120
cggcgccgca ggacaaattg gatatgctct tgtccccatg attgctaggg gtgtgatgtt      180
gggtgctgac cagcctgtta ttctacacat gcttgacatt ccaccagcta ctgaatctct      240
taatggcctt aagatggagc tggttgatgc tgcatttcct cttttgaagg gaattgtcgc      300
aacaactgat gttgtggagg cctgcactgg tgtgaatgtt gcggttatgg ttggtgggtt      360
ccccaggaag gagggaatgg aaaggaagga tgttatgtca aaaaatgtct ccatctacaa      420
```

| | |
|---|---|
| atcccaagct tctgctcttg aggctcatgc agccoctaac tgcaaggttc tggtagttgc | 480 |
| caatccagca aacaccaacg ctctcatctt aaaagaattc gctccatcca tccctgagaa | 540 |
| gaacattact tgcctcaccc gtcttgacca acagggca cttggccaga tctctgaaaa | 600 |
| acttaatgtc caagttactg atgtgaagaa tgcgatcatc tggggcaacc actcatccac | 660 |
| ccagtaccct gatgttaacc acgccactgt gaagactccc agtggagaga agcctgtcag | 720 |
| ggaactcgtt gctgatgatg agtggttaaa tacggaattc atctctaccg tccagcagcg | 780 |
| tggtgccgcc atcatcaagg cgaggaagca atccagtgcc ctatctgctg ccagctctgc | 840 |
| atgcgatcac attcgtgact gggttcttgg cactcctgag gaacatttg tctccatggg | 900 |
| tgtgtactct gatggttcgt atggtgtgcc tgctggtctg atctactcgt tcccagtaac | 960 |
| atgcagtggt ggcgaatgga cgattgttca gggtctcccg atcgacgagt tctcaaggaa | 1020 |
| gaagatggac gcgactgccc aggagctgtc ggaggagaag acgctcgctt actcatgcct | 1080 |
| caactaaaac taagcaatac ccagagggac agatagtgag cgattgcccg ctcccgtgtt | 1140 |
| tttgaataaa agagactttt aagttccatc acatagaaac tgtttatctc agaccgctgc | 1200 |
| acatcgcgag atgtggagcg cagatgccgt tgctggtttt actccagtgt gtattgaggc | 1260 |
| tttgtactag ctcccttttt tttgcctggt gattcgcagg acatttgctg aaaacattga | 1320 |
| acccatttga catctgatgg aatcatggac cagtagcaag tacattttg cgaaagcata | 1380 |
| atctgcatcg ggcttgggct ggtggttgaa ctttctgcca catggcccnt gg | 1432 |

<210> SEQ ID NO 43
<211> LENGTH: 659
<212> TYPE: DNA
<213> ORGANISM: Oryza sativa
<220> FEATURE:
<221> NAME/KEY: misc_feature
<223> OTHER INFORMATION: TC83646 (PRO0175)

<400> SEQUENCE: 43

| | |
|---|---|
| gctaagtgag ctagccactg atcagaagaa cacctcgatc tctgagagtg ttttttcagc | 60 |
| tttagcttaa gcaggatgga gcaccagggg cagcacggcc acgtgaccag ccgcgtcgac | 120 |
| gagtacggca acccggtcgg caccggcgcc ggacacggcc agatgggcac cgccggcatg | 180 |
| gggacgcacg gcaccgccgg caccggcggc ggccagttcc agccgatgag ggaggagcac | 240 |
| aagaccggcg gcgtcctgca acgctccggc agctccagct caagctcgtc tgaggatgat | 300 |
| ggaatgggag ggaggaggaa gaaggggatc aaggagaaga tcaaggagaa gctccccggc | 360 |
| ggcaacaagg gcgagcagca gcatgccatg gcggcaccg gcaccggcac cggcaccggc | 420 |
| accggaaccg gcggcgccta cgggcagcag ggccacggca ccgggatgac caccggcacc | 480 |
| accggcgcac acggcaccac caccaccgac accggcgaga agaagggcat catggacaag | 540 |
| atcaaggaga agctgcccgg ccagcactga gctcgacaca ccaccacacc atgtgtctgc | 600 |
| gccccccggcg accgccgcca cgtcaccttc ctgaataata agatgagcta accgagcgc | 659 |

<210> SEQ ID NO 44
<211> LENGTH: 1310
<212> TYPE: DNA
<213> ORGANISM: Oryza sativa
<220> FEATURE:
<221> NAME/KEY: misc_feature
<223> OTHER INFORMATION: TC90619 (PRO0177)

<400> SEQUENCE: 44

| | |
|---|---|
| ggaccagcga gcaaccagcc ccccgccccc aatggcggca gagcagcttt gcccaccgct | 60 |

```
gccgcttttg cccacctctc ctccgattaa tccccctcccc tcctcttcct cccacttctc    120
cgcctcctct tcctcccctc gccgaccccta cctactcgcg ccgccgccgt cgcattgggc    180
ggcaaacgga gggggggtta accctgatgg agcagtacga gaaggaggag aagattgggg    240
agggcacgta cggggtggtg tacagggcgc gggacaaggt caccaacgag acgatcgcgc    300
tcaagaagat ccggcttgag caggaggatg agggcgtccc ctccaccgca atccgcgaga    360
tctcgctcct caaggagatg catcacggca acatcgtcag gttacacgat gttatccaca    420
gtgagaagcg catatatctt gtctttgagt atctggatct ggacctaaag aagttcatgg    480
actcttgtcc agagtttgcg aaaaacccca ctttaattaa gtcatatctc tatcagatac    540
tccgcggcgt tgcttactgt cattctcata gagttcttca tcgagatttg aaacctcaga    600
atttattgat agatcggcgt actaatgcac tgaagcttgc agactttggt ttagccaggg    660
catttggaat tcctgtccgc acgtttactc acgaggttgt aaccttgtgg tatagagctc    720
cagagatcct tcttggatca aggcagtatt ctacaccagt tgatatgtgg tcagttggtt    780
gtatctttgc agaaatggtg aaccagaaac cactgttccc tggtgattct gagattgatg    840
aattatttaa gatattcagg gtactaggaa ctccaaatga acaaagttgg ccaggagtta    900
gctcattacc tgactacaag tctgctttcc ccaagtggca agcacaggat cttgcaacta    960
ttgtccctac tcttgaccct gctggtttgg accttctctc taaaatgctt cggtacgagc    1020
caaacaaaag gatcacagct agacaggctc ttgagcatga atacttcaag gaccttgaga    1080
tggtacaatg accctgctat ggctttacat tggattggca tatgtatggg ctgggctcct    1140
catttcattc cttctgtgaa cgctgtgccc ttcgtttggg cattttttgtc attcagctgg    1200 atatttcaaa tcttgtgtgt tgatatgta ttcaggaacg ctaaatagat caccgtcttg    1260
gtctctattt gttcagagta aatatcttcc aatgctgcct ttcagtttcc                1310
```

<210> SEQ ID NO 45
<211> LENGTH: 55
<212> TYPE: DNA
<213> ORGANISM: Artificial sequence
<220> FEATURE:
<223> OTHER INFORMATION: prm3780

<400> SEQUENCE: 45

```
ggggacaagt ttgtacaaaa aagcaggctt cgacgctact caagtggtgg gaggc          55
```

<210> SEQ ID NO 46
<211> LENGTH: 55
<212> TYPE: DNA
<213> ORGANISM: Artificial sequence
<220> FEATURE:
<223> OTHER INFORMATION: prm2768

<400> SEQUENCE: 46

```
ggggacaagt ttgtacaaaa aagcaggctc ccgatttagt agaccacatt ttggc          55
```

<210> SEQ ID NO 47
<211> LENGTH: 54
<212> TYPE: DNA
<213> ORGANISM: Artificial sequence
<220> FEATURE:
<223> OTHER INFORMATION: prm2420

<400> SEQUENCE: 47

```
ggggacaagt ttgtacaaaa aagcaggcta tgccatcgag tggtgtgccg atac           54
```

<210> SEQ ID NO 48
<211> LENGTH: 54
<212> TYPE: DNA
<213> ORGANISM: Artificial sequence
<220> FEATURE:
<223> OTHER INFORMATION: prm2853

<400> SEQUENCE: 48
ggggacaagt tgtacaaaa aagcaggctt ctcttctgaa gctgaagccc tgcg         54

<210> SEQ ID NO 49
<211> LENGTH: 53
<212> TYPE: DNA
<213> ORGANISM: Artificial sequence
<220> FEATURE:
<223> OTHER INFORMATION: prm2426

<400> SEQUENCE: 49
ggggacaagt tgtacaaaa aagcaggcta aaaccaccga gggacctgat ctg          53

<210> SEQ ID NO 50
<211> LENGTH: 55
<212> TYPE: DNA
<213> ORGANISM: Artificial sequence
<220> FEATURE:
<223> OTHER INFORMATION: prm2855

<400> SEQUENCE: 50
ggggacaagt tgtacaaaa aagcaggctc ctagctatat gcagaggttg acagg        55

<210> SEQ ID NO 51
<211> LENGTH: 53
<212> TYPE: DNA
<213> ORGANISM: Artificial sequence
<220> FEATURE:
<223> OTHER INFORMATION: prm3025

<400> SEQUENCE: 51
ggggacaagt tgtacaaaa aagcaggcta tggtgccatg tcaataagac atc          53

<210> SEQ ID NO 52
<211> LENGTH: 56
<212> TYPE: DNA
<213> ORGANISM: Artificial sequence
<220> FEATURE:
<223> OTHER INFORMATION: prm3029

<400> SEQUENCE: 52
ggggacaagt tgtacaaaa aagcaggctg tttttctatg aaccggtcat taaacc       56

<210> SEQ ID NO 53
<211> LENGTH: 55
<212> TYPE: DNA
<213> ORGANISM: Artificial sequence
<220> FEATURE:
<223> OTHER INFORMATION: prm3061

<400> SEQUENCE: 53
ggggacaagt tgtacaaaa aagcaggctc ctgatggatg atgaatcact gatcg        55

<210> SEQ ID NO 54
<211> LENGTH: 57
<212> TYPE: DNA
<213> ORGANISM: Artificial sequence
<220> FEATURE:
<223> OTHER INFORMATION: prm3031

<400> SEQUENCE: 54
ggggacaagt tgtacaaaa aagcaggctt cgttaagttt gatgatttct gatgacc        57

<210> SEQ ID NO 55
<211> LENGTH: 53
<212> TYPE: DNA
<213> ORGANISM: Artificial sequence
<220> FEATURE:
<223> OTHER INFORMATION: prm3051

<400> SEQUENCE: 55
ggggaccact tgtacaaga aagctgggtg ccgccgctcg ctcgcttcgt tcg            53

<210> SEQ ID NO 56
<211> LENGTH: 58
<212> TYPE: DNA
<213> ORGANISM: Artificial sequence
<220> FEATURE:
<223> OTHER INFORMATION: prm3592

<400> SEQUENCE: 56
ggggacaagt tgtacaaaa aagcaggctc gtgttcatgt tcgcatttag gattggac       58

<210> SEQ ID NO 57
<211> LENGTH: 55
<212> TYPE: DNA
<213> ORGANISM: Artificial sequence
<220> FEATURE:
<223> OTHER INFORMATION: prm5131

<400> SEQUENCE: 57
ggggacaagt tgtacaaaa aagcaggctc agatgccaca gtatggtgta ccacc          55

<210> SEQ ID NO 58
<211> LENGTH: 56
<212> TYPE: DNA
<213> ORGANISM: Artificial sequence
<220> FEATURE:
<223> OTHER INFORMATION: prm3782

<400> SEQUENCE: 58
ggggacaagt tgtacaaaa aagcaggctt tgcagttgtg accaagtaag ctgagc         56

<210> SEQ ID NO 59
<211> LENGTH: 54
<212> TYPE: DNA
<213> ORGANISM: Artificial sequence
<220> FEATURE:
<223> OTHER INFORMATION: prm2844

<400> SEQUENCE: 59
ggggacaagt tgtacaaaa aagcaggctt ttggcgcggg gcagaagagt ggac           54

<210> SEQ ID NO 60
<211> LENGTH: 57
<212> TYPE: DNA
<213> ORGANISM: Artificial sequence
<220> FEATURE:
<223> OTHER INFORMATION: prm2973

<400> SEQUENCE: 60
ggggacaagt tgtacaaaa aagcaggctg cttgagtcat agggagaaaa caaatcg        57

<210> SEQ ID NO 61

```
<211> LENGTH: 53
<212> TYPE: DNA
<213> ORGANISM: Artificial sequence
<220> FEATURE:
<223> OTHER INFORMATION: prm3770

<400> SEQUENCE: 61
ggggacaagt tgtacaaaa aagcaggctc gtcctccttt tgtaacggct cgc          53

<210> SEQ ID NO 62
<211> LENGTH: 56
<212> TYPE: DNA
<213> ORGANISM: Artificial sequence
<220> FEATURE:
<223> OTHER INFORMATION: prm3772

<400> SEQUENCE: 62
ggggacaagt tgtacaaaa aagcaggctc atgcggctaa tgtagatgct cactgc       56

<210> SEQ ID NO 63
<211> LENGTH: 53
<212> TYPE: DNA
<213> ORGANISM: Artificial sequence
<220> FEATURE:
<223> OTHER INFORMATION: prm3774

<400> SEQUENCE: 63
ggggacaagt tgtacaaaa aagcaggctt agtaccattc ttccctcgtg agc          53

<210> SEQ ID NO 64
<211> LENGTH: 53
<212> TYPE: DNA
<213> ORGANISM: Artificial sequence
<220> FEATURE:
<223> OTHER INFORMATION: pm3776

<400> SEQUENCE: 64
ggggacaagt tgtacaaaa aagcaggctg tttggttggt gaccgcaatt tgc          53

<210> SEQ ID NO 65
<211> LENGTH: 55
<212> TYPE: DNA
<213> ORGANISM: Artificial sequence
<220> FEATURE:
<223> OTHER INFORMATION: prm3800

<400> SEQUENCE: 65
ggggacaagt tgtacaaaa aagcaggctg tcaccaccgt catgtacgag gctgc        55

<210> SEQ ID NO 66
<211> LENGTH: 55
<212> TYPE: DNA
<213> ORGANISM: Artificial sequence
<220> FEATURE:
<223> OTHER INFORMATION: prm5135

<400> SEQUENCE: 66
ggggacaagt tgtacaaaa aagcaggctc agacacctag aatatagaca ttccc        55

<210> SEQ ID NO 67
<211> LENGTH: 55
<212> TYPE: DNA
<213> ORGANISM: Artificial sequence
<220> FEATURE:
<223> OTHER INFORMATION: prm3781

<400> SEQUENCE: 67
```

```
ggggaccact ttgtacaaga aagctgggtg atcacaagcg cagctaatca ctagc         55
```

<210> SEQ ID NO 68
<211> LENGTH: 57
<212> TYPE: DNA
<213> ORGANISM: Artificial sequence
<220> FEATURE:
<223> OTHER INFORMATION: prm2769

<400> SEQUENCE: 68

```
ggggaccact ttgtacaaga aagctgggtc gtgtagaaaa tcttacccg aaaatcg        57
```

<210> SEQ ID NO 69
<211> LENGTH: 55
<212> TYPE: DNA
<213> ORGANISM: Artificial sequence
<220> FEATURE:
<223> OTHER INFORMATION: prm2421

<400> SEQUENCE: 69

```
ggggaccact ttgtacaaga aagctgggtg gtgaggtgcc ggggaagcga cgttg         55
```

<210> SEQ ID NO 70
<211> LENGTH: 54
<212> TYPE: DNA
<213> ORGANISM: Artificial sequence
<220> FEATURE:
<223> OTHER INFORMATION: prm2854

<400> SEQUENCE: 70

```
ggggaccact ttgtacaaga aagctgggtt tcttctttcc cttggaacta accg          54
```

<210> SEQ ID NO 71
<211> LENGTH: 54
<212> TYPE: DNA
<213> ORGANISM: Artificial sequence
<220> FEATURE:
<223> OTHER INFORMATION: prm2427

<400> SEQUENCE: 71

```
ggggaccact ttgtacaaga aagctgggtt gtcgctttta tttggcttgg tgtg          54
```

<210> SEQ ID NO 72
<211> LENGTH: 56
<212> TYPE: DNA
<213> ORGANISM: Artificial sequence
<220> FEATURE:
<223> OTHER INFORMATION: prm2856

<400> SEQUENCE: 72

```
ggggaccact ttgtacaaga aagctgggtc tctagctcga tctctcttgc aaaagc        56
```

<210> SEQ ID NO 73
<211> LENGTH: 49
<212> TYPE: DNA
<213> ORGANISM: Artificial sequence
<220> FEATURE:
<223> OTHER INFORMATION: prm3026

<400> SEQUENCE: 73

```
ggggaccact ttgtacaaga aagctgggtg gcgatgagat cttcctccg               49
```

<210> SEQ ID NO 74
<211> LENGTH: 59
<212> TYPE: DNA

<213> ORGANISM: Artificial sequence
<220> FEATURE:
<223> OTHER INFORMATION: prm3030

<400> SEQUENCE: 74
ggggaccact ttgtacaaga aagctgggtt tttgtaggat tctactacta tgcttcaac            59

<210> SEQ ID NO 75
<211> LENGTH: 62
<212> TYPE: DNA
<213> ORGANISM: Artificial sequence
<220> FEATURE:
<223> OTHER INFORMATION: prm3062

<400> SEQUENCE: 75
ggggaccact ttgtacaaga aagctgggta ttgtgtaaat atttctattg tccagtaatc            60
ac                                                                          62

<210> SEQ ID NO 76
<211> LENGTH: 54
<212> TYPE: DNA
<213> ORGANISM: Artificial sequence
<220> FEATURE:
<223> OTHER INFORMATION: prm3032

<400> SEQUENCE: 76
ggggaccact ttgtacaaga aagctgggtg atggcagagt taattagcaa acgc                 54

<210> SEQ ID NO 77
<211> LENGTH: 50
<212> TYPE: DNA
<213> ORGANISM: Artificial sequence
<220> FEATURE:
<223> OTHER INFORMATION: prm3052

<400> SEQUENCE: 77
ggggacaagt ttgtacaaaa aagcaggctc taagggcagc agccattggg                      50

<210> SEQ ID NO 78
<211> LENGTH: 60
<212> TYPE: DNA
<213> ORGANISM: Artificial sequence
<220> FEATURE:
<223> OTHER INFORMATION: prm3049

<400> SEQUENCE: 78
ggggaccact ttgtacaaga aagctgggtg gcggcggcgg cggcggcggc ggctgggtct           60

<210> SEQ ID NO 79
<211> LENGTH: 54
<212> TYPE: DNA
<213> ORGANISM: Artificial sequence
<220> FEATURE:
<223> OTHER INFORMATION: prm2195

<400> SEQUENCE: 79
ggggaccact ttgtacaaga aagctgggtc ggcttagaga ggggaggaag cgaa                 54

<210> SEQ ID NO 80
<211> LENGTH: 58
<212> TYPE: DNA
<213> ORGANISM: Artificial sequence
<220> FEATURE:
<223> OTHER INFORMATION: prm2197

<400> SEQUENCE: 80
ggggaccact tgtacaaga aagctgggtt ggtgtgagtg tttgagtttg gagtgagc          58

<210> SEQ ID NO 81
<211> LENGTH: 57
<212> TYPE: DNA
<213> ORGANISM: Artificial sequence
<220> FEATURE:
<223> OTHER INFORMATION: prm2845

<400> SEQUENCE: 81
ggggaccact tgtacaaga aagctgggtc ggcaatgtga tgcaatgcaa attaagc          57

<210> SEQ ID NO 82
<211> LENGTH: 55
<212> TYPE: DNA
<213> ORGANISM: Artificial sequence
<220> FEATURE:
<223> OTHER INFORMATION: prm2974

<400> SEQUENCE: 82
ggggaccact tgtacaaga aagctgggtc gcaaacttgg ctggaatcac tcacc             55

<210> SEQ ID NO 83
<211> LENGTH: 54
<212> TYPE: DNA
<213> ORGANISM: Artificial sequence
<220> FEATURE:
<223> OTHER INFORMATION: prm3771

<400> SEQUENCE: 83
ggggaccact tgtacaaga aagctgggtt gtcgcctctc ctctgcaatg cgtg              54

<210> SEQ ID NO 84
<211> LENGTH: 52
<212> TYPE: DNA
<213> ORGANISM: Artificial sequence
<220> FEATURE:
<223> OTHER INFORMATION: prm3773

<400> SEQUENCE: 84
ggggaccact tgtacaaga aagctgggtg gctgaatcct gcgagaaggg cg                52

<210> SEQ ID NO 85
<211> LENGTH: 54
<212> TYPE: DNA
<213> ORGANISM: Artificial sequence
<220> FEATURE:
<223> OTHER INFORMATION: prm3775

<400> SEQUENCE: 85
ggggaccact tgtacaaga aagctgggtg atctctccct ctccctctcc ctgg              54

<210> SEQ ID NO 86
<211> LENGTH: 52
<212> TYPE: DNA
<213> ORGANISM: Artificial sequence
<220> FEATURE:
<223> OTHER INFORMATION: prm3777

<400> SEQUENCE: 86
ggggaccact tgtacaaga aagctgggtt ggagcggaag ggggggggga gc                52

```
<210> SEQ ID NO 87
<211> LENGTH: 57
<212> TYPE: DNA
<213> ORGANISM: Artificial sequence
<220> FEATURE:
<223> OTHER INFORMATION: prm3801

<400> SEQUENCE: 87
ggggaccact ttgtacaaga aagctgggtc actctcagag atcgaggtgt tcttctg      57

<210> SEQ ID NO 88
<211> LENGTH: 52
<212> TYPE: DNA
<213> ORGANISM: Artificial sequence
<220> FEATURE:
<223> OTHER INFORMATION: prm5136

<400> SEQUENCE: 88
ggggaccact ttgtacaaga aagctgggtc gcccgcagct cgcccccgtc cg           52
```

RICE PROMOTERS

The present invention relates to the field of plant molecular biology, more particularly to nucleic acid sequences useful for driving and/or regulating expression of an operably linked nucleic acid in plants. The isolation of these nucleic acid sequences from rice, as well as their use in driving and/or regulating expression of an operably linked nucleic acid is disclosed. The present invention therefore concerns promoters, hybrid promoters, genetic constructs, expression cassettes, transformation vectors, expression vectors, host cells and transgenic plants comprising the isolated nucleic acids according to the present invention. The present invention also concerns methods for driving and/or regulating expression of a nucleic acid and methods for the production of transgenic plants.

Gene expression is dependent on initiation of transcription, which is mediated via the transcription initiation complex. Gene expression is also dependent on regulation of transcription, which regulation determines how strong, when or where a gene is expressed. Said regulation of gene expression may be mediated via transcriptional control elements, which are generally embedded in the nucleic acid sequence 5'-flanking or upstream of the expressed gene. This upstream nucleic acid region is often referred to as a "promoter" since it promotes the binding, formation and/or activation of the transcription initiation complex and therefore is capable of driving and/or regulating expression of the 3' downstream nucleic acid sequence.

Genetic engineering of plants with the aim of obtaining a useful plant phenotype, often involves heterologous gene expression, which is generally mediated by a promoter capable of driving and/or regulating expression of an operably linked heterologous nucleic add. The phenotype of the host plant only depends on the contribution of the heterologous nucleic acid, but also on the contribution of the specific expression pattern of the chosen promoter determining how, where and when that heterologous nucleic add is expressed. Accordingly, the choice of promoter with a suitable expression pattern is of crucial importance for obtaining the suitable phenotype. A person skilled in the art will need to have available different promoters, to determine the optimal promoter for a particular nucleic acid. For many different host plants, this availability is rather limited and there is therefore a continuing need to provide new promoters with various expression profiles.

The nucleic adds as presented in SEQ ID NO 1 to 22 were isolated from *Oryza saliva* and have been found to be capable of driving and regulating expression of an operably linked nucleic acid; their expression patterns have also been characterized. Therefore the present invention offers a collection of hitherto unknown isolated nucleic acids, which isolated nucleic acids are useful as promoters.

Accordingly, the present invention provides an isolated promoter capable of driving and/or regulating expression, comprising:
  (a) an isolated nucleic acid as given in any one of SEQ ID NO 1 to 22 or the complement of any one of SEQ ID NO 1 to 22; or
  (b) an isolated nucleic acid having at least 90% sequence identity with any of the DNA sequences as given in any one of SEQ ID NO 1 to 22; or
  (c) an isolated nucleic acid specifically hybridizing under stringent conditions with any of the DNA sequences as given in any one of SEQ ID NO 1 to 22; or
  (d) an isolated nucleic acid as defined in any one of (a) to (c), which is interrupted by an intervening sequence; or
  (e) a fragment of any of the nucleic acids as defined in (a) to (d), which fragment is capable of driving and/or regulating expression.

The term "isolated" as used herein means being removed from its original source. Preferably, the "isolated" promoter is free of sequences (such as protein encoding sequences or other sequences at the 3' end) that naturally flank the promoter in the genomic DNA of the organism from which the promoter is derived. Further preferably, the "isolated" promoter is also free of sequences that naturally flank it at the 5' end. Further preferably, the "isolated" promoter may comprise less than about 5 kb, 4 kb, 3 kb, 2 kb, 1.6 kb, 1.2 kb, 1 kb, 0.8 kb, 0.5 kb or 0.1 kb of nucleotide sequences that naturally occur with the promoter in genomic DNA from the organism of which the promoter is derived.

The present invention is not limited to the nucleic acids as presented by SEQ ID NO 1 to 22. A person skilled in the art will recognize that variants or fragments of a nucleic add may occur, whilst maintaining the same functionality. These variants or fragments may be man made (e.g. by genetic engineering) or may even occur in nature. Therefore the present invention extends to variant nucleic acids and fragments of any of SEQ ID NO 1 to 22, which variants or fragments are useful in the methods of the present invention. Such variants and fragments include:
  (a) an isolated nucleic acid as given in any one of SEQ ID NO 1 to 22 or the complement of any one of SEQ ID NO 1 to 22; or
  (b) an isolated nucleic acid having at least 90% sequence identity with any of the DNA sequences as given in any one of SEQ ID NO 1 to 22; or
  (c) an isolated nucleic acid specifically hybridizing under stringent conditions with any of the DNA sequences as given in any one of SEQ ID NO 1 to 22; or
  (d) an isolated nucleic acid as defined in any one of (a) to (c), which is interrupted by an intervening sequence; or
  (e) a fragment of any of the nucleic adds as defined in (a) to (d), which fragment is capable of driving and/or regulating expression.

Suitable variants of any one of SEQ ID NO 1 to 22 encompass homologues which have in increasing order of preference at least 90%, 91%, 92%, 93%, 94%, 95%, 96%, 97%, 98% or 99% sequence identity with any one of the nucleic acids as represented in SEQ ID NO 1 to 22.

The percentage of identity may be calculated using an alignment program. Preferably a pair wise global alignment program may be used, which implements the algorithm of Needleman-Wunsch (J. Mol. Biol. 48: 443-453, 1970). This algorithm maximizes the number of matches and minimizes the number of gaps. Such programs are for example GAP, Needle (EMBOSS package), stretcher (EMBOSS package) or Align X (Vector NTI suite 5.5) and may use the standard parameters (for example gap opening penalty 15 and gap extension penalty 6.66). Alternatively, a local alignment program implementing the algorithm of Smith-Waterman (Advances in Applied Mathematics 2, 482-489 (1981)) may be used. Such programs are for example Water (EMBOSS package) or matcher (EMBOSS package). "Sequence identity" as used herein is preferably calculated over the entire length of the promoters as represented by any one of SEQ ID NO 1 to 22. The length of these promoters is presented in Table 2

Search and identification of homologous nucleic acids, would be well within the realm of a person skilled in the art. Such methods involve screening sequence databases with the sequence provided by the present invention, for example any one of SEQ ID NO 1 to 22, preferably in a computer readable form. Useful sequence databases include but are not limited to Genbank the European Molecular Biology Laboratory Nucleic acid Database (EMBL) or versions thereof, or the MIPS database. Different search algorithms and software for the alignment and comparison of sequences are well known in the art. Such software includes, for example GAP, BSETFIT, BLAST, FASTA and TFASTA. Preferably BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX and TBLASTX) and two designed for protein sequence queries (BLASTP and TBLASTN) (Coulson, Trends in Biotechnology: 76-80, 1994; Birren et al., GenomeAnalysis, 1:543, 1997). The software for performing BLAST analysis is publicly available through the National Centre for Biotechnology information.

The sequences of the genome of *Arabidopsis thaliana* and the genome of *Oryza sativa* are now available in public databases such as Genbank. Other genomes are currently being sequenced. Therefore, it is expected that as more sequences of the genomes of other plants become available, homologous promoters may be identifiable by sequence alignment with any one of SEQ ID NO 1 to SEQ ID NO 22. The skilled person will readily be able to find homologous promoters from other plant species, for example from other crop plants, such as maize. Homologous promoters from other crop plants are especially useful for practising the methods of the present invention in crop plants.

One example of homologues having at least 90% sequence identity with any one of SEQ ID NO to 22 are allelic variants of any one of SEQ ID NO 1 to 22. Allelic variants are variants of the same gene occurring in two different individuals of the same species and usually allelic variants differ by slight sequence changes. Allelic variants may encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms.

Homologues suitable for use in the methods according to the invention may readily be isolated from their source organism via the technique of PCR or hybridization. Their capability of driving and/or regulating expression may readily be determined, for example, by following the methods described in the Examples section by simply substituting the sequence used in the actual Example with the homologue.

Other suitable variants of any one of SEQ ID NO 1 to 22 encompassed by the present invention are nucleic acids specifically hybridising under stringent conditions to any one of the nucleic adds of SEQ ID NO 1 to 22. The term "hybridising" means annealing to substantially homologous complementary nucleotide sequences in a hybridization process. Tools in molecular biology relying on such a hybridization process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination, Northern blotting (RNA blotting), Southern blotting (DNA blotting). The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic add chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. Conventional hybridization conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions can be designed in function of the known or the expected homology and/or length of the nucleic acid sequence. High stringency conditions for hybridisation include high temperature and/or low sodium/salt concentration (salts include sodium as for example in NaCl and Na$_3$-citrate) and/or the inclusion of formamide in the hybridisation buffer and/or lowering the concentration of compounds such as SDS (sodium dodecyl sulphate detergent) in the hybridisation buffer and/or exclusion of compounds such as dextran sulphate or polyethylene glycol (promoting molecular crowding) from the hybridisation buffer. Specifically hybridising under stringent conditions means that the sequences have to be very similar. Specific hybridization under stringent conditions is preferably carried out at a temperature of 60° C. followed by washes in 0.1 to 1×SSC, 0.1×SDS, and 1×SSC, 0.1×SDS.

The invention also relates to a nucleic add molecule of at least 15 nucleotides in length hybridizing specifically with any of the nucleic adds of the invent on. The invention also relates to a nucleic add molecule of at least 15 nucleotides in length specifically amplifying a nucleic add of the invention by polymerase chain reaction.

Another variant of any of SEQ ID NO 1 to 22 encompassed by the present invention are nucleic acids corresponding to any one of SEQ ID NO 1 to 22 or variants thereof as described hereinabove, which are interrupted by an intervening sequence. For example, any of the nucleic adds as presented in SEQ ID NO 1 to 22 may be interrupted by an intervening sequence. With "intervening sequences" is meant any nucleic acid or nucleotide, which disrupts another sequence. Examples of intervening sequences comprise introns, nucleic add tags, T-DNA and mobilizable nucleic acids sequences such as transposons or nucleic acids that can be mobilized via recombination. Examples of particular transposons comprise Ac (activator), Ds (Dissociation), Spm (suppressor-Mutator) or En. The introduction of introns into promoters is now widely applied. The methods according to the present invention may also be practised using a nucleic acid sequence according to any one of SEQ ID NO 1 to 22 provided with an intron. In case the intervening sequence is an intron, alternative splice variants of the nucleic adds according to the invention may arise. The term "alternative splice variant" as used herein encompasses variants of a nucleic acid sequence in which intervening introns have been excised, replaced or added. Such splice variants may be found in nature or may be manmade. Methods for making such promoters with an intron or for making the corresponding splice variants are well known in the art.

Variants interrupted by an intervening sequence, suitable for use in the methods according to the invention may readily be determined for example by following the methods described in the Examples section by simply substituting the sequence used in the actual Example with the variant.

The variant nucleic acids as described hereinabove may be found in nature (for example allelic variants or splice variants). Additionally and/or alternatively, variants of any one of SEQ ID NO 1 to 22 as described hereinabove may be man-made via techniques well known in the art involving for example mutation, substitution, insertion, deletions or derivation. The present invention also encompasses such variants, as well as their use in the methods of the present invention.

A "mutation varant" of a nucleic acid may readily be made using recombinant DNA manipulation techniques or nucleotide synthesis. Examples of such techniques include site directed mutagenesis via M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols. Alternatively, the nucleic acid of the present invention may be randomly mutated.

A "substitutional variant" refers to those variants in which at least one residue in the nucleic add sequence has been removed and a different residue inserted in its place. Nucleic acid substitutions are typically of single residues, but may be clustered depending upon functional constraints placed upon the nucleic add sequence; insertions usually are of the order of about 1 to about 10 nucleic add residues, and deletions can range from about 1 to about 20 residues.

An "insertional variant" of a nucleic add is a variant in which one or more nucleic add residues are introduced into a predetermined site in that nucleic acid. Insertions may comprise 5'-terminal and/or 3'-terminal fusions as well as intra-sequence insertions of single or multiple nucleotides. Generally, insertions within the nucleic add sequence will be smaller than 5'- or 3'-terminal fusions, of the order of about 1 to 10 residues. Examples of 5'- or 3'-terminal fusions include the coding sequences of binding domain a or activation domains of a transcriptional activator as used in the yeast two-hybrid system or yeast one-hybrid system, or of phage coat proteins, (histidine) $_s$-tag, glutathione S-transferase-tag, protein A, maltose-binding protein, dihydrofolate reductase, Tag®100 epitope, c-myc epitope, FLAG®-epitope, lacZ, CMP (calmodulin-binding peptide), HA epitope, protein C epitope and VSV epitope.

The term "derivative" of a nucleic acid may comprise substitutions, and/or deletions and/or additions of naturally and non-naturally occurring nucleic add residues compared to the natural nucleic acid. Derivatives may, for example, comprise methylated nucleotides, or artificial nucleotides.

Also encompassed with in the present invention are promoters, comprising a fragment of any of the nucleic adds as presented by any one of SEQ ID NO 1 to 22 or variants thereof as described hereinabove. A "fragment" as used herein means a portion of a nucleic add sequence. Suitable fragments useful in the methods of the present invention are functional fragments, which retain at least one of the functional parts of the promoter and hence are still capable of driving and/or regulating expression. Examples of functional fragments of a promoter include the minimal promoter, the upstream regulatory elements, or any combination thereof.

Suitable fragments may range from at least about 20 base pairs or about 50, 100, 150, 200, 250, 300, 350, 400, 450, 500, 550, 600, 650, 700, 750, 800, 850, 900, 950 or 100 0 base pairs, up to about the full length sequence of the invention. These base pairs are typically immediately upstream of the transcription initiation start, but alternatively may be from anywhere in the promoter sequence.

Suitable fragments useful in the methods of the present invention may be tested for their capability of driving and/or regulating expression by standard techniques well known to the skilled person, or by the following method described in the Example section.

The promoters as disclosed in any one of SEQ ID NO 1 to 22 are isolated as nucleic acids of approximately 1.2 kb from the upstream region of particular rice coding sequences (CDS). These nucleic adds may include typical elements of a promoter, which are presented in FIG. 1. Generally, a promoter may comprises from coding sequence to the upstream direction: (i) an 5'UTR of pre-messenger RNA, (ii) a minimal promoter comprising the transcription initiation element (INR) and more upstream a TATA box, and (iii) may contain regulatory elements that determine the specific expression pattern of the promoter.

The term "promoter" as used herein is taken in a broad context and refers to regulatory nucleic acid sequences capable of effecting (driving and/or regulating) expression of the sequences to which they are operably linked. A "promoter" encompasses transcriptional regulatory sequences derived from a classical genomic gene. Usually a promoter comprises a TATA box, which is capable of directing the transcription initiation complex to the appropriate transcription initiation start site. However, some promoters do not have a TATA box TATA-less promoters), but are still fully functional for driving and/or regulating expression. A promoter may additionally comprise a CCAAT box sequence and additional regulatory elements (i.e. upstream activating sequences or cis-elements such as enhancers and silencers). A "promoter" may also include the transcriptional regulatory sequences of a classical prokaryotic gene, in which case it may include a −35 box sequence and/or a −10 box transcriptional regulatory sequences.

"Driving expression" as used herein means promoting the transcription of a nucleic acid.

"Regulating expression" as used herein means influencing the level, time or place of transcription of a nucleic acid. The promoters of the present invention may thus be used to increase, decrease or change in time and/or place transcription of a nucleic acid. For example, they may be used to limit the transcription to certain cell types, tissues or organs, or during a certain period of time, or in response to certain environmental conditions.

The promoter is preferably a plant-expressible promoter. The term "plant expressible" means being capable of regulating expression in a plant, plant cell, plant tissue and/or plant organ. Accordingly, the invention encompasses an isolated nucleic add as mentioned above, capable of regulating transcription of an operably linked nucleic acid in a plant or in one or more particular cells, tissues or organs of a plant.

The expression pattern of the promoters according to the present invention were studied in detail and it was found that many of them were tissue-specific. Accordingly, the present invention provides "tissue-specific" promoters. The term "tissue-specific" shall be taken to indicate that expression is predominantly in a particular tissue, tissue-type, organ or any other part of the organism, albeit not necessarily exclusively in said tissue, tissue-type, organ or other part. Accordingly, the invention encompasses an isolated nucleic acid as mentioned above, capable of driving and/or regulating expression (of an operably linked nucleic acid) in a tissue-specific manner. Expression may be driven and/or regulated in the seed, embryo, scutellum, aleurone, endosperm, leaves, flower, calli, meristem, shoot meristem, discriminating centre, shoot, shoot meristem and root. In grasses the shoot meristem is located in the so-called discrimination zone from where the shoot and the leaves originate.

A tissue-specific promoter is one example of a so-called "regulated promoter". These promoters are regulated by endogenous signals such as the presence of certain transcription factors, metabolites, plant hormones, or exogenous signals, such as ageing, stresses or nutritional status. These regulations may have an effect on one or more different levels such spatial specificity or temporal specificity. Encompassed within the present invention is a nucleic acid as described hereinabove, which is a "regulated promoter". Examples of regulated promoters are cell specific promoters, tissue-specific promoters, organ-specific promoters, cell cycle-specific promoters, inducible promoters or young tissue-specific promoters.

Alternatively and/or additionally, some promoters of the present invention display a constitutive expression pattern. Accordingly, the present invention provides a promoter as described hereinabove, which is a constitutive promoter. The term "constitutive" means having no or very few spatial or temporal regulations. The term "constitutive expression" as used herein refers to a substantially continuously expression in substantially all tissues of the organism. The skilled craftsman will understand that a "constitutive promoter" is a promoter that is active during most, but not necessarily all, phases of growth and development of the organism and throughout most, but not necessarily all, parts of an organism.

The "expression pattern" of a promoter is not only influenced by the spatial and temporal aspects, but also by the level of expression. The level of expression is determined by the so-called "strength" of a promoter. Depending on the resulting expression level, a distinction is made herein between "weak" or "strong" promoters. Generally by "weak promoter" is meant a promoter that drives expression of an operably finked nucleic add at levels of about $1/10000$ transcripts to about $1/100000$ transcripts to about $1/500000$ transcripts. Generally, by "strong promoter" is meant a promoter that drives expression at levels of about $1/10$ transcripts, to about $1/100$ or to about $1/1000$ transcripts.

According to a particular embodiment, the invention provides an isolated promoter as mentioned hereinabove, which is a hybrid promoter. The term "hybrid promoter" as used herein refers to a chimeric promoter made, for example, synthetically, for example by genetic engineering. Preferred hybrid promoters according to the present invention comprise a part, preferably a functional part, of one of the promoters according to the present invention and at least another part, preferably a functional part of a promoter. The latter part, may be a part of any promoter, including any one of the promoters according to the present invention and other promoters. One example of a hybrid promoter comprises regulatory element(s) of a promoter according to the present invention combined with the minimal promoter of another promoter. Another example of a hybrid promoter is a promoter comprising additional regulatory elements to further enhance its activity and/or to alter its spatial and/or temporal expression pattern.

The present invention also provides use of a functional fragment of any one of SEQ ID NO 1 to 22 or variant thereof for changing the expression pattern of a promoter. In such methods, at least part of any of the nucleic adds according to the present invention are combined with at least one fragment of another promoter.

Further, the invention provides a genetic construct comprising:
  (a) An isolated promoter as defined hereinabove
  (b) A heterologous nucleic add sequence operably linked to isolated promoter of (a), and optionally
  (c) A 3' transcription terminator The term "genetic construct" as used herein means a nucleic add made by genetic engineering.

The term "operably linked" to a promoter as used herein means that the transcription is driven and/or regulated by that promoter. A person skilled in the art will understand that being operably linked to a promoter preferably means that the promoter is postponed upstream (i.e. at the 5'-end) of the operably linked nucleic add. The distance to the operably linked nucleic acid may be variable, as long as the promoter of the present invention is capable of driving and/or regulating the transcription of the operably linked nucleic add. For example, between the promoter and the operably linked nucleic acid, there might be a cloning site, an adaptor, a transcription or translation enhancer.

The operably linked nucleic add may be any coding or non-coding nucleic acid. The operably linked nucleic acid may be in the sense or in the anti-sense direction. Typically in the case of genetic engineering of host cells, the operably linked nucleic add is to be introduced into the host cell and is intended to change the phenotype of the host cell. Alternatively, the operably linked nucleic add is an endogenous nucleic add from the host cell.

The term "heterologous" as used herein is intended to be "heterologous to the promoter of the present invention". A nucleic add that is heterologous to the promoter of the present invention is not naturally occurring in the nucleic add sequences flanking the promoter of the present invention when it is in its biological genomic environment. While the nucleic add may be heterologous to the promoter of the present invention, it may be homologous or native or heterologous or foreign to the plant host cell. The heterologous operably linked nucleic acid may be any nucleic add (for example encoding any protein), provided that it comprises or it is flanked by at least one nucleotide which is normally not flanking the promoter of the present invention.

The term "transcription terminator" as used in (c) refers to a DNA sequence at the end of a transcriptional unit which signals termination of transcription. Terminators are 3'-nontranslated DNA sequences usually containing a polyadenylation signal, which facilitates the addition of polyadenylate sequences to the 3'-end of a primary transcript. Terminators active in and/or isolated from viruses, yeasts, moulds, bacteria, insects, birds, mammals and plants are known and have been described in literature. Examples of terminators suitable for use in the gene tic constructs of the present invention include the *Agrobacterium tumefaciens* nopaline synthase (NOS) gene terminator, the *Agrobacterium tumefaciens* octopine synthase (OCS) gene terminator sequence, the Cauliflower mosa ic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

The present invention also provides an expression cassette, a transformation vector or a plant expression vector comprising a genetic construct as described above.

An "expression cassette" as meant herein refers to a minimal genetic construct necessary for expression of a nucleic add. A typical expression cassette comprises a promoter-gene-terminator combination. An expression cassette may additionally comprise cloning sites, for example Gateway™ recombination sites or restriction enzyme recognition sites, to allow easy cloning of the operably linked nucleic acid or to allow the easy transfer of the expression cassette into a vector. An expression cassette may further comprise 5' untranslated regions, 3' untranslated regions, a selectable marker, transcription enhancers or translation enhancers.

With "transformation vector" is meant a genetic construct, which may be introduced in an organism by transformation and may be stably maintained in said organism. Some vectors may be maintened in for example *Escherichia coli, A. tumefaciens, Saccharomyces cerevisiae* or *Schizosaccharomyces pombe*, while others such as phagemids and cosmid vectors, may be maintained in bacteria and/or viruses. Transformation vectors may be multiplied in their host cell and may be isolated again therefrom to be transformed into another host cell. Vector sequences generally comprise a set of unique sites recognized by restriction enzymes, the multiple cloning site (MCS), wherein one or more non-vector sequence(s) can be inserted. Vector sequences may further comprise an origin of replication which is required for maintenance and/or replication in a specific host cell. Examples of origins of replication include, but are not limited to, the f1-ori and colE1.

"Expression vector" form a subset of transformation vectors, which, by virtue of comprising the appropriate regulatory sequences, enable expression of the inserted non-vector sequence(s). Expression vectors have been described which are suitable for expression in bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells. One suitable expression vector according to the present invention is a plant expression vector, useful for the transformation of plant cells, the stable integration in the plant genome, the maintenance in the plant cell and the expression of the non-vector sequences in the plant cell.

Typically, a plant expression vector according to the present invention comprises a nucleic acid of any one of SEQ ID NO 1 to 22 or a variant thereof as described hereinabove, optionally operably linked to a second nucleic acid. Typically, a plant expressible vector according to the present invention, further comprises T-DNA regions for stable integration into the plant genome (for example the left border and the right border regions of the Ti plasmid).

The genetic constructs of the invention may further comprise a "selectable marker". As used herein, the term "selectable marker" includes any gene, which confers a phenotype to a cell in which it is expressed, to facilitate the identification and/or selection of cells that are transfected or transformed. Suitable markers may be selected from markers that confer antibiotic or herbicide resistance. Cells containing the genetic construct will thus survive antibiotics or herbicide concentrations that kill untransformed cells. Examples of selectable marker genes include genes conferring resistance to antibiotics (such as nptll encoding neomycin phosphotransferase capable of phosphorylating neomycin and kanamycin, or h pt encoding hygromycin phosphotransferase capable of phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example beta-glucuronidase, GUS), luminescence (such as luciferase) or fluorescence (Green Fluorescent Protein, GFP, and derivatives there of). Further examples of suitable selectable marker genes include the ampicillin resistance (Ampr), tetracycline resistance gene (Tcr), bacterial kanamycin resistance gene (Kanr), phosphinothricin resistance gene, and the chloramphenicol acetyltransferase (CAT) gene, amongst others.

Furthermore, the present invention encompasses a host cell comprising an isolated promoter, or a genetic construct, or an expression cassette, or a transformation vector or an expression vector according to the invention as described hereinabove. In particular embodiments of the invention, the host cell is selected from bacteria, algae, fungi, yeast, plants, insect or animal host cells.

In one particular embodiment, the invention provides a transgenic plant cell comprising an isolated promoter according to the invention, or an isolated nucleic acid, or a genetic construct, or an expression cassette, or a transformation vector or an expression vector according to the invention as described hereinabove. Preferably said plant cell is a dicot plant cell or a monocot plant cell, more preferably a cell of any of the plants as mentioned herein. Preferably, in the transgenic plant cell according to the invention, the promoter or the genetic construct of the invention is stably integrated into the genome of the plant cell.

The invention also provides a method for the production of a transgenic plant, comprising:

(a) introducing into a plant cell an isolated promoter, for example any one of SEQ ID NO 1 to SEQ ID NO 22, or a variant or fragment thereof, or a genetic construct, or an expression cassette, or a transformation vector or an expression vector according to the present invention and as described hereinabove, and (b) Cultivating said plant cell under conditions promoting plant growth.

"Introdudng" the above mentioned isolated promoter, or genetic construct or expression cassette, or transformation vector or expression vector, into a host cell (e.g. plant cell) is preferably achieved by transformation. The term "transformation" as used herein encompasses the transfer of an exogenous polynucleotide into a host cell, irrespective of the method used for transfer. In particular for plants, tissues capable of clonal propagation, whether by organogenesis or embryogenesis, are suitable to be transformed with a genetic construct of the present invention and a whole plant may be regenerated therefrom. The particular tissue chosen will vary depending on the clonal propagation systems available for, and best suited to, the particular plant species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a plant cell and may be maintained non-integrated, for example, as a plasmid. Alternatively, it may be integrated into the plant genome.

Transformation of a plant species is now a fairly routine technique. Advantageously, any of several transformation methods may be used to introduce the nucleic add a of the invention into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A et al., 1986, Mol. Gen Genet 202, 179-185); DNA or RNA-coated particle bombardment (Klein T. M. et al., 1987, Nature 327, 70) infection with (non-integrative) viruses and the like. A preferred transformation method for the production of transgenic plant cells according to the present invention, is an *Agrobacterium* mediated transformation method.

Transgenic rice plants comprising any one of the promoters of the present invention are preferably produced via *Agrobacterium*-mediated transformation using any of the well-known methods for rice transformation, such as the ones described in any of the following: published European patent application EP 1198985 A1, Aldemita and Hodges (Planta, 199, 612-417, 1996); Chan et al. (Plant Mol. Biol. 22 (3) 491-506, 1993); Hiel et al. (Plant J. 6 (2) 271-282, 1994); which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest (which could be under the control of any of the promoters of the present invention), following which the transformed material may be cultivated under conditions promoting plant growth.

The resulting transformed plant cell may then be used to regenerate a transformed plant in a manner known to persons skilled in the art. Accordingly, the method for the production of a transgenic plant as described hereinabove, may further comprise regenerating a plant from said plant cell of (a).

The present invention further provides a plant comprising a plant cell as described hereinabove. The plants may also be able to grow, or even reach maturity including for example fruit production, seed formation, seed ripening and seed setting.

Furthermore, progeny may be produced from these seeds, which progeny may be fertile. Alternatively or additionally, the transformed and regenerated plants may also produce progeny by non-sexual propagation such as cloning, grafting. The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Following DNA transfer and growth of the transformed cells, putatively transformed plant cells or plants may be evaluated, for instance using Southern analysis, for the presence of the gene of interest, copy number and/or genomic organization. Alternatively or additionally, expression levels or expression patterns of the newly introduced DNA may be undertaken using northern and/or Western analysis, both techniques being well known to persons having ordinary skill in the art.

The present invention clearly extends to plants obtainable by any of the methods according to the present invention, which plants comprise any of the isolated promoters or the constructs of the present invention. The present invention clearly extends to any plant parts and propagules of such plant. The present invention extends further to encompass the progeny of a primary transformed cell, tissue, organ or whole plant that has been produced by any of the aforementioned methods, the only requirement being that progeny exhibit the same genotypic and/or phenotypic characteristic(s) as those produced in the parent by the methods according to the invention. The invention also extends to harvestable parts of a plant, such as but not limited to seeds, leaves, fruits, flowers, stem cultures, stem, rhizomes, roots, tubers, bulbs and cotton fibers.

The term "plant" or "plants" as used herein encompasses whole plants, ancestors and progeny of plants and plant parts, including seeds, shoots, stems, roots (including tubers), and plant cells, tissues and organs. The term "plant" therefore also encompasses suspension cultures, embryos, meristematic regions, callus tissue, gametophytes, sporophytes, pollen, and microspores. Plants that are particularly useful in the methods of the invention include all plants which belong to the superfamily *Viridiplantae*, in particular monocotyledonous and dicotyledonous plants including a fodder or forage legume, ornamental plant, food crop, tree, or shrub selected from the list comprising *Acacia* spp., *Acer* spp., *Actfnidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baildaea plurijuga*, *Betula* spp., *Brassica* spp., *Bruguie ra gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyp arrhenia rufa*, *Hypericum erectum*, *Hyperthelia dissoluta*, *Indigo Incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot es culenta*, *Medicago sativa*, *Metasequoia glyptostroboides*, *Musa sapientum*, *Nicotianum* spp., *Onobrychis* spp., *Omithopus* spp., *Oryza* spp., *Peltophorum africanum*, *Pennisetum* spp., *Persea gratissima*, *Petunia* spp., *Phaseolus* spp., *Phoenix canariensis*, *Phormium co okianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis um bellata*, *Rhopalostylis sapida*, *Rhus natalensis*, *Ribes grossularia*, *Ribes*spp., *Robinia pseudoacacia*, *Rosa* spp., *Rubus*spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylia*, *Vaccinium* spp., *Vicia* spp. *Vitis vinifera*, *Watsonia pyramidata*, *Zantedesc hia aethiopica*, *Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, trees and algae amongst others. According to a preferred feature of the present invention, the plant is a crop plant such as soybean, sunflower, canola, alfalfa, rapeseed, cotton, tomato, potato, tobacco, squash, papaya, poplar, leguminosa, flax, lupinus or sorghum. According to another preferred embodiment of the present invention the plant is a monocotyledonous plant, such as sugarcane, further preferable a cereal such as rice, maize, wheat, barley, millet, rye or oats.

The Invention further provides a method for driving and/or regulating expression of a nucleic acid in a plant or plant cell, comprising:
a) Operably linking a nucleic acid to an isolated nucleic acid according to the invention as described hereinabove, such as to any one of SEQ ID NO 1 to 22 or a variant or fragment thereof, and
b) Introducing the resultant genetic construct into a plant or plant cell.

Preferably the operably linked nucleic add of (a) is heterologous to the nucleic acids according to the present invention.

This method may further comprise cultivating the transformed plant or plant cell under conditions promoting growth, promoting regeneration and/or promoting maturation.

Furthermore, the expression of the operably linked nucleic acid may be driven and/or regulated in particular cells, tissues or organs of a plant. Accordingly, the invention provides a method as described above, wherein the expression is constitutive expression or tissue-specific expression. For these embodiments, reference is made to the example section where the specific expression patterns of the promoters according to the invention are described and where different types of tissue-specific expression are detailed.

The present invention further encompasses the use of an isolated nucleic acid as defined hereinabove to drive and/or regulate expression of an operably linked nucleic acid.

The person skilled in the art will recognize that provision of sequences SEQ ID NO 1 to 22, readily makes available the tools to isolate related promoters, which may have substantial sequence identity to any of SEQ ID ID NO 1 to 22. Additionally, provision of sequences SEQ ID NO 23 to 44 (CDS corresponding to the promoters of the present invention, see Table 1), readily makes available the tools to iso late related promoters, of which the related CDSs may have substantial sequence identity to any of SEQ ID NO 23 to 44. Therefore the present invention also encompasses a method for isolating nucleic adds, capable of driving and/or regulating expression of an operably linked nucleic add, comprising screening a nucleic acid sequence database to find homologues of any of the sequences represented by SEQ ID NO 1 to 22 or SEQ ID NO 23 to 44. Subsequently these homologues are used to screen a library with genomic DNA, which library is for example prepared from the organism of origin of the above mentioned homologue. The screening procedure may for example involve hybridization. Subsequently, the genomic DNA that matches the homologue, is analysed to identify the transcription initiation site and the translation initiation site of the gene corresponding to the homologue. Finally, specific primers are designed for amplification of a nucleic add located in the region upstream (at the 5' end) of said translation initiation site.

The present invention extends to the identification of regulatory proteins that are involved in the regulation of the activity of the promoters according to the present invention. Such identification may be achieved using a yeast one-hybrid system. In such a yeast one-hybrid system the sequences according to any one of SEQ ID NO 1 to 22 are operably linked to the GAL transcription activator and transformed to a yeast cell culture. That yeast cell culture is again transformed with a library of constructs encoding candidate regulatory factors.

The present invention will now be described with reference to the following figures in which:

FIG. 1 shows a general schematic representation of a promoter. Regulatory elements are sequences that may for example be responsible for special and/or temporal regulation of the promoter activity. The minimal promoter is the minimal sequence necessary and sufficient to drive expression. It includes a TATA box, which is necessary to correctly direct the RNA polymerase 11 to the transcription initiation site. The transcription initiation element (INR) in dudes the transcription initiation start site. The 5' untranslated region (5'UTR) is the region that is transcribed into pre-messenger RNA and eventually into mRNA, but is not translated into protein. The translation initiation codon is represented by the startcodon ATG.

FIG. 2 is a map of the vector p4581 useful for expression in plants of a β-glucuronidase (GUS) gene under control of any one of the promoters according to the invention. This binary vector comprises a Gateway recombination cassette, suitable for the recombination cloning of any of the promoters of the present invention in front of the *Escherichia coli* β-glucuronidase (GUS) gene. This cassette contains a chloramphenicol resistance gene (CamR) and the ccdB suicide gene for counter selection of non-recombined plasmids, This GUS expression cassette further comprises the double terminator sequence T-zein and T-rbcS-deltaGA. This expression cassette is located within the left border (LB repeat, LB Ti C58) and the right border (RB repeat, RB Ti C58) of the nopailne Ti plasmid. Cloned within these borders are also selectable marker and a screenable marker genes each under control of a constitutive promoter and a terminator sequence. This vector also contains an origin of replication (pBR322) for bacterial replication and a bacterial selectable marker (Spe/SmeR) for bacterial selection.

The following figures show the results of the GUS staining of plants or plant parts transformed with the reporter vector p4581 carrying a promoter according to the present invention operably linked to the reporter gene GUS. Plants denoted "C plants" are transgenic plants grown to about 5 cm; Plants denoted "B plants" are grown to about 10 cm; and plants denoted "A plants" are grown to maturity. These A plants were used to collect different tissue samples from old leaves, young leaves and seeds.

EXAMPLES

Figure 1:
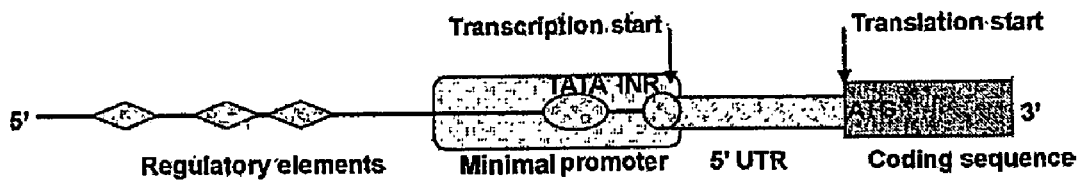

The promoters according to the present invention were isolated as DNA regions spanning about 1.2 kb of the sequence upstream of the translation initiation codon (i.e. first ATG, which codon was excluded) from various rice genes. For determination of their nucleic add sequence and their expression pattern, the following procedure was followed: First in silico studies on genomic rice sequences were performed. However, procedures based on automated prediction programs to locate promoter-like nucleic acid sequence are highly error prone, even for the localization the best-characterized promoter control elements such as the TATA box and the transcription initiation element (INR). Also, in silico determination of expression pattern is extremely speculative. Therefore, to obtain unambiguous data about the nucleic acid sequence and the expression pattern of the promoters, in vivo studies were performed encompassing (i) isolation of the promoter nucleic add sequence; (ii) operably linking a reporter gene to the promoter and introducing the resulting genetic construct into a host organisms; (iii) growing the transformed host cell under conditions allowing expression of the reporter gene, and (iv) determination of the reporter gene activity in the different tissues of the host organism. These methods are now described in more detail.

Example 1

Identification of Rice ESTs, the Corresponding Genes and their Location in the Rice Genome Sequence databases, comprising rice sequences, were searched for rice expressed sequence tags (ESTs). Subsequently an in silico Northern-blot was performed to allow identification of EST families that are strongly expressed or that are specific for a particular organ. This analysis included normalization of the numbers of ESTs isolated from different plant organs. The ESTs families with an interesting distribution among source cDNA libraries were selected for further analysis and sequence homology searches. After sequence homology searches in combination with scanning scientific data, the genes that correspond to those families of EST s were identified from sequence databases and a (putative) function and corresponding gene name was given (see Table 1). Subsequently, the corresponding promoter region was isolated by the following procedure. In a first step the TIGR database was searched to find a tentative contig corresponding to an EST family. Sequence homology was found using standard computer programs, such as Blast N using standard parameters (typically G Cost to open a gap=5, E Cost to extend a gap=2, q Penalty for a mismatch in the blast portion of run =−3, r Reward for a match in the blast portion of run=1, e Expectation value=10.0, W Word size=11, v Number of one-line descriptions=100, b Number of alignments to show=100, Matrix=BLOSUM62). The TIGR database (The Institute for Genomic Research), provides Tentative Contigs (TC) which are sequence predictions based on contig building from all known EST, from all known cDNA and from reconstructed mRNA. The TCs used for identification of the promoters of the present invention are represented in Table 1. In a second step these TCs were used to locate the corresponding gene on a genomic sequence, which gene comprises the coding region as well as the promoter region. Generally, these genomic sequences were BAC clones, which are represented herein by their Genbank accession number (see Table 1). From these BAC clones the sequence identity of the promoter region could be determined.

TABLE 1 list of rice promoters of the present invention. The promoter sequences are represented herein by their SEQ ID NO and promoter number (PRO). The coding sequences (CDS) naturally driven by a promoter of the present invention are represented by their name, by SEQ ID NO and by Tentative contig (TC) accession number of the TIGR database. The Genomic sequences (BAC clones or genes) comprising a promoter region of the present invention are represented by their Genbank accession number.

| Prom SEQ ID NO | Prom number | CDS name | CDS SEQ ID NO | CDS TC | BAC clone (*or gene) |
|---|---|---|---|---|---|
| 1 | PRO0110 | RCc3 | 23 | TC89946 | AC037426 |
| 2 | PRO0005 | putative beta-amylase | 24 | TC90358 | AC022457 |
| 3 | PRO0009 | putative cellulose synthase | 25 | TC83635 | AC022457 |

TABLE 1-continued list of rice promoters of the present invention. The promoter sequences are represented herein by their SEQ ID NO and promoter number (PRO). The coding sequences (CDS) naturally driven by a promoter of the present invention are represented by their name, by SEQ ID NO and by Tentative contig (TC) accession number of the TIGR database. The Genomic sequences (BAC clones or genes) comprising a promoter region of the present invention are represented by their Genbank accession number.

| Prom SEQ ID NO | Prom number | CDS name | CDS SEQ ID NO | CDS TC | BAC clone (*or gene) |
|---|---|---|---|---|---|
| 4 | PRO0058 | proteinase inhibitor Rgpi9 | 26 | TC83117 | AF044059 |
| 5 | PRO0061 | beta expansine EXPB9 | 27 | TC89913 | AC020666 |
| 6 | PRO0063 | structural protein | 28 | TC89985 | AP001278 |
| 7 | PRO0081 | putative caffeoyl-CoA 3-O-methyltransferase | 29 | TC89891 | AP000364 |
| 8 | PRO0091 | prolamine RP5 | 30 | TC89670 | AF156714* |
| 9 | PRO0095 | putative methionine aminopeptidase | 31 | TC89883 | AC027133 |
| 10 | PRO0111 | uclacyanin 3-like protein | 32 | TC90434 | AJ307662 |
| 11 | PRO0116 | 26S proteasome regulatory particle non -ATPase subunit 11 | 33 | TC83072 | AP000969 |
| 12 | PRO0117 | putative 40S ribosomal protein | 34 | TC90038 | AC090871 |
| 13 | PRO0122 | chlorophyll a/b-binding protein presursor (Cab27) | 35 | TC82936 | AP004700 |
| 14 | PRO0123 | putative protochlorophyllide reductase | 36 | TC89839 | AL606456 |
| 15 | PRO0133 | chitinase Cht-3 | 37 | TC85888 | D16223* |
| 16 | PRO0151 | WSI18 | 38 | TC84300 | AP003023 |
| 17 | PRO0169 | aquaporine | 39 | TC89687 | AP005108 |
| 18 | PRO0170 | High mobility group protein | 40 | TC89846 | AP004004 |
| 19 | PRO0171 | reversibly glycosylated protein RGP1 | 41 | TC82935 | AC090874 |
| 20 | PRO0173 | cytosolic MDH | 42 | TC82977 | AC037425 |
| 21 | PRO0175 | RAB21 | 43 | TC83646 | Y00842* |
| 22 | PRO0177 | Cdc2-1 | 44 | TC90619 | AP004765 |

Identification and Isolation of the Promoter Regions of Rice Genes

Sterling from the sequence information of the gene a and their location in the rice genome, the promoter regions of these genes were Isolated as the DNA region spanning about 1.2 kb upstream of the translation initiation codon (i.e. first ATG), which codon was excluded. When an intervening sequence such as an intron, was present in the 5' untranslated region of the gene, the isolated DNA region was taken as the region spanning about 1.2 kb, plus the length of that intervening sequence. The promoter regions were isolated from genomic DNA of *Oryza sativa Japonica* or exceptionally from *Oryza sativa Indica* via PCR using specific primers. These specific primers comprise AttB recombination sites, suitable for recombination cloning of the isolated promoter region These specific primers are herein represented as SEQ ID NO 45 to 88 and are listed in Table 2. Conditions for PCR were as follows: 1 cycle of 2 min at 94° C., 35 cycles of 1 min at 94° C., 1 min at 58° C. and 2 min at 68° C., and 1 cycle of 5 min at 68° C. The length of the expected PCR fragment is also indicated in Table 2. The corresponding PCR fragment was purified from the PCR reaction mix via gele electrophoresis and subsequent purification using Zymoclean Gel DNA Recovery Kit (Zymo Research, Orange, Calif.).

TABLE 2

Overview of the primers used to isolate the rice promoters of the present invention and the length of the rice promoter regions.

| Promoter SEQ ID NO | Promoter number | Prom length | Primer forward SEQ ID NO | Primer forward | Primer reverse SEQ ID NO | Primer reverse |
|---|---|---|---|---|---|---|
| 1 | PRO0110 | 1264 | 45 | prm3780 | 67 | prm3781 |
| 2 | PRO0005 | 1215 | 46 | prm2768 | 68 | prm2769 |
| 3 | PRO0009 | 1038 | 47 | prm2420 | 69 | prm2421 |
| 4 | PRO0058 | 1301 | 48 | prm2853 | 70 | prm2854 |
| 5 | PRO0061 | 1243 | 49 | prm2426 | 71 | prm2427 |
| 6 | PRO0063 | 1019 | 50 | prm2855 | 72 | prm2856 |
| 7 | PRO0081 | 1212 | 51 | prm3025 | 73 | prm3026 |
| 8 | PRO0091 | 1052 | 52 | prm3029 | 74 | prm3030 |
| 9 | PRO0095 | 1216 | 53 | prm3061 | 75 | prm3062 |
| 10 | PRO0111 | 1237 | 54 | prm3031 | 76 | prm3032 |
| 11 | PRO0116 | 1100 | 55 | prm3051 | 77 | prm3052 |
| 12 | PRO0117 | 1216 | 56 | prm3592 | 78 | prm3049 |
| 13 | PRO0122 | 1210 | 57 | prm5131 | 79 | prm2195 |
| 14 | PRO0123 | 123 | 58 | prm3782 | 80 | prm2197 |
| 15 | PRO0133 | 1808 | 59 | prm2844 | 81 | prm2845 |
| 16 | PRO0151 | 1828 | 60 | prm2973 | 82 | prm2974 |
| 17 | PRO0169 | 1267 | 61 | prm3770 | 83 | prm3771 |
| 18 | PRO0170 | 1130 | 62 | prm3772 | 84 | prm3773 |
| 19 | PRO0171 | 1230 | 63 | prm3774 | 85 | prm3775 |

TABLE 2-continued

Overview of the primers used to isolate the rice promoters of the present invention and the length of the rice promoter regions.

| Promoter SEQ ID NO | Promoter number | Prom length | Primer forward SEQ ID NO | Primer forward | Primer reverse SEQ ID NO | Primer reverse |
|---|---|---|---|---|---|---|
| 20 | PRO0173 | 1234 | 64 | prm3776 | 86 | prm3777 |
| 21 | PRO0175 | 1553 | 65 | prm3800 | 87 | prm3801 |
| 22 | PRO0177 | 1087 | 66 | prm5135 | 88 | prm5136 |

Example 2

Cloning of Promoter-Gus Reporter Vectors For Plant Transformation

The purified PCR fragments of Example 1. Corresponding to the promoter regions of the present invention, were cloned into the pDONR201 entry plasmid of the Gateway™ system (Life Technologies) using the "BP recombination reaction". The identity and base pair composition of the cloned insert was confirmed by sequencing and additionally, the resulting plasmid was tested via restriction digests.

Figure 2:
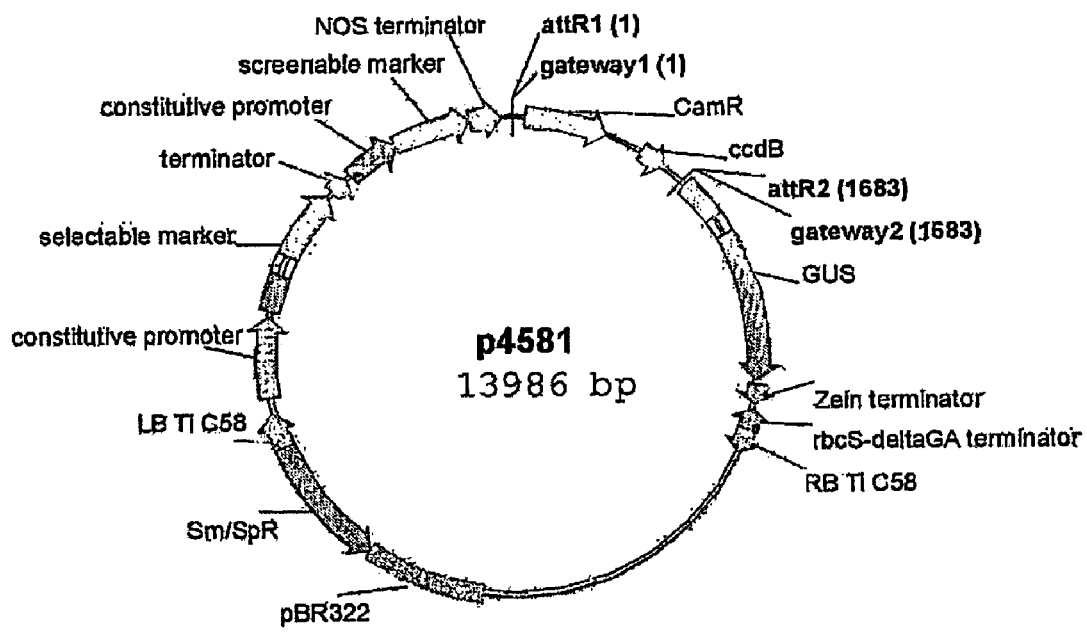
Figure 3:
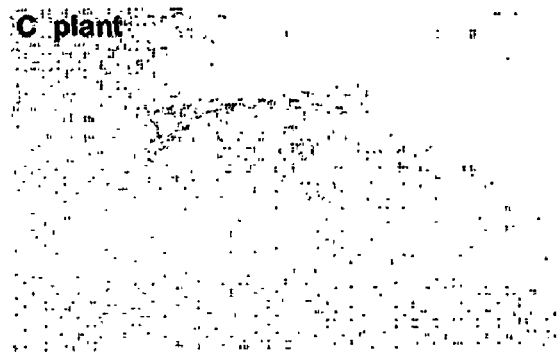
FIG. 3 shows the expression pattern of PRO0110 (RCc3, SEQ ID NO 1). GUS staining is visible in roots.
Figure 4:
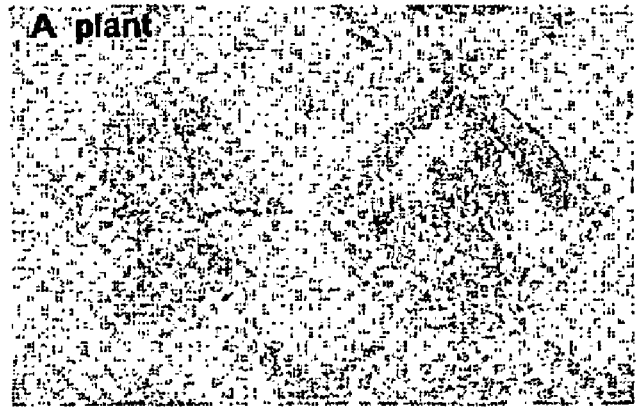
FIG. 4 shows the expression pattern of PRO0005 (putative beta-amylase, SEQ ID NO 2). GUS staining is visible in seeds, more specifically in the embryo or in the scutellum of the embryo.
Figure 5:
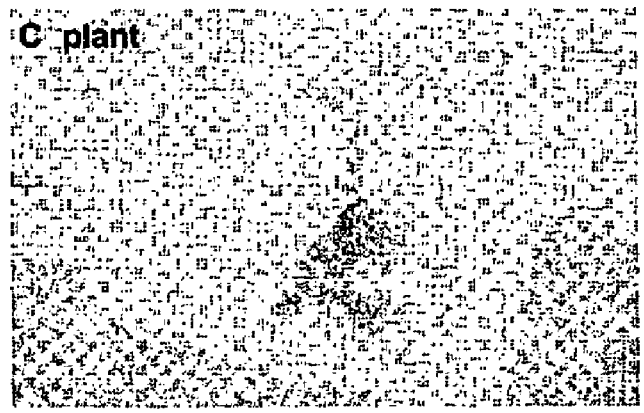
FIG. 5 shows the expression pattern of PRO0009 (putative cellulose synthetase, SEQ ID NO 3). GUS staining is visible in roots.
Figure 6:
FIG. 6 shows the expression pattern of PRO0058 (proteinase inhibitor Rgpi9, SEQ ID NO 4). GUS staining is visible in the seeds.
Figure 7:
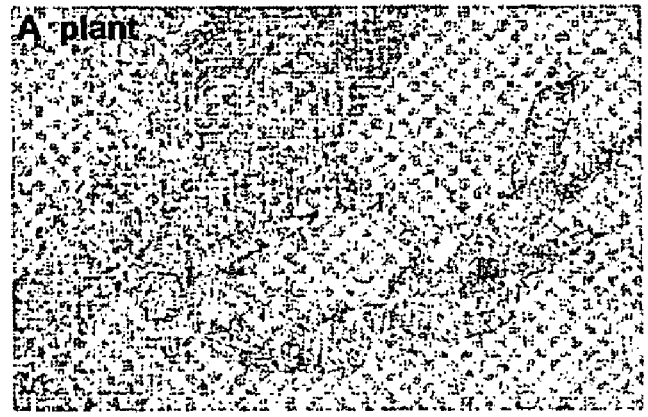
FIG. 7 shows the expression pattern of PRO0061 (beta expansine EXPB9, SEQ ID NO 5). GUS staining is visible in young flowers of A plants (A) and in other young expanding tissues of B plants (B) and C plants (C).
Figure 7:
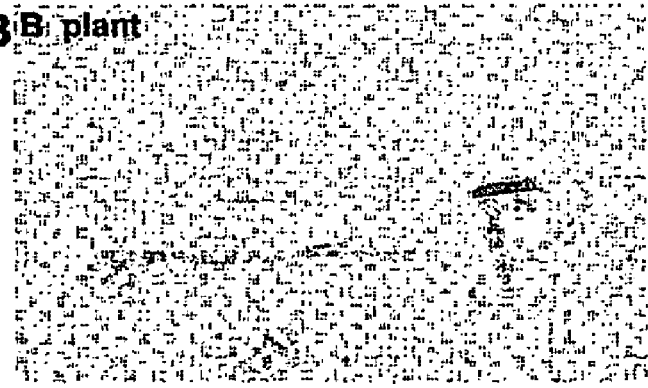
Figure 7:
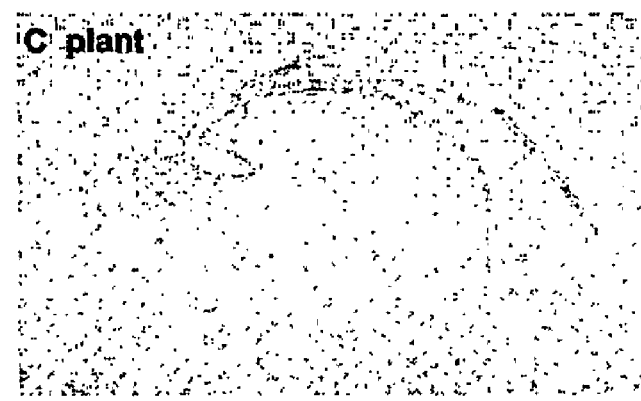
Figure 8:
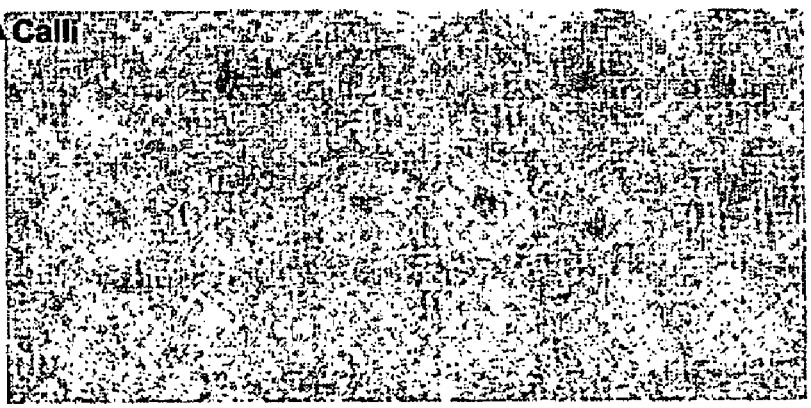
FIG. 8 shows the expression pattern of PRO0063 (putative structural protein, SEQ ID NO 6). GUS staining is visible in young tissues, for example in the calli (A) or old leaves, young leaves and seeds of "A plants" (B).
Figure 9:
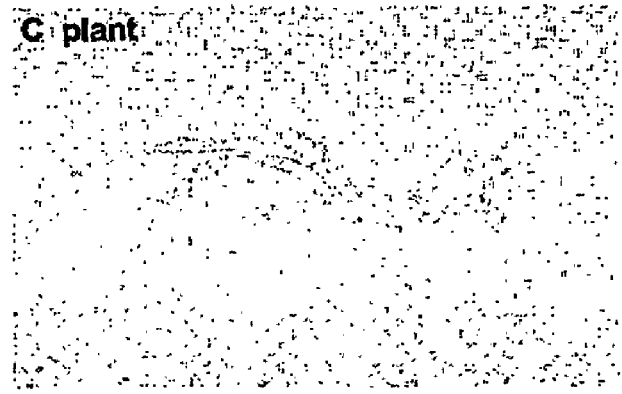
FIG. 9 shows the expression pattern of PRO0081 (putative caffeoyl-CoA 3-O-methyltransferase, SEQ ID NO 7). GUS staining is visible in young tissues, particularly of the shoot.
Figure 10:
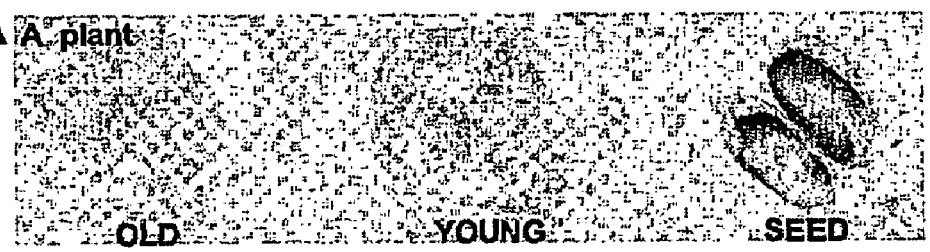
FIG. 10 shows the expression pattern of PRO0091 (prolamine RP5, SEQ ID NO 8). GUS staining is visible in seeds (A), particularly in the endosperm, and in meristem (B).
Figure 10:
Figure 11:
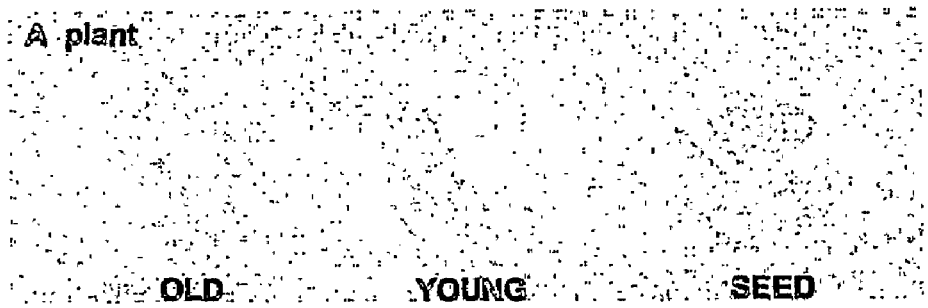
FIG. 11 shows the expression pattern of PRO0095 (putative amino peptidase, SEQ ID NO 9). GUS staining is visible in seeds, more particularly in the embryo.
Figure 12:
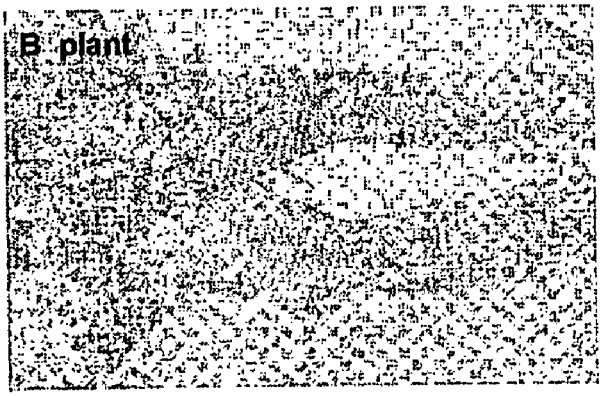
FIG. 12 shows the expression pattern of PRO0111 (uclacyanin 3-like protein, SEQ ID NO 10). GUS staining is visible in roots and in meristem.
Figure 13:
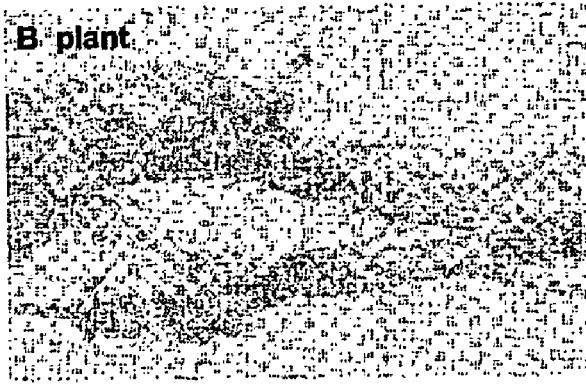
FIG. 13 shows the expression pattern of PRO0116 (26S proteasome regulatory particle non-ATPase subunit 11, SEQ ID NO 11). GUS staining is weakly visible in the whole plant (weak constitutive) and is particularly visible in meristem.
Figure 14:
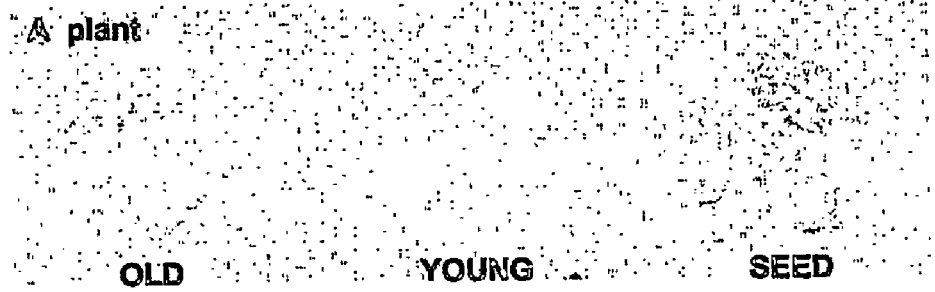
FIG. 14 shows the expression pattern of PRO 0117 (putative 40S ribosomal protein, SEQ ID NO 12). GUS staining is visible in the seeds, more particularly in the endosperm.
Figure 15:
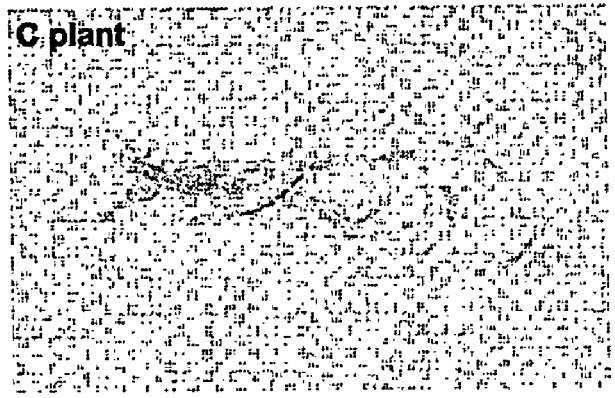
FIG. 15 shows the expression pattern of PRO0122 (chlorophyll a/b-binding protein presursor (Cab27), SEQ ID NO 13). GUS staining is visible in the shoot.
Figure 16:
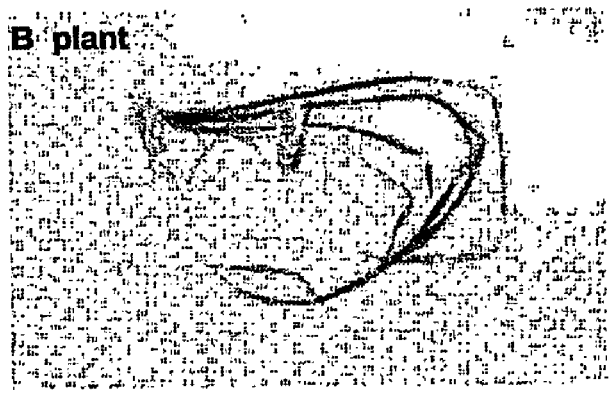
FIG. 16 shows the expression pattern of PRO0123 (putative protochlorophylide reductase, SEQ ID NO 14). GUS staining is visible in the shoot (above-ground tissues).
Figure 17:
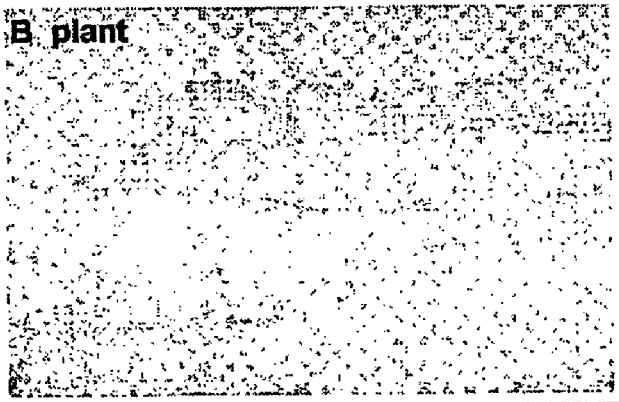
FIG. 17 shows the expression pattern of PRO0133 (chitinase Cht-3, SEQ ID NO 15). GUS staining is visible in the roots and meristem.
Figure 18:
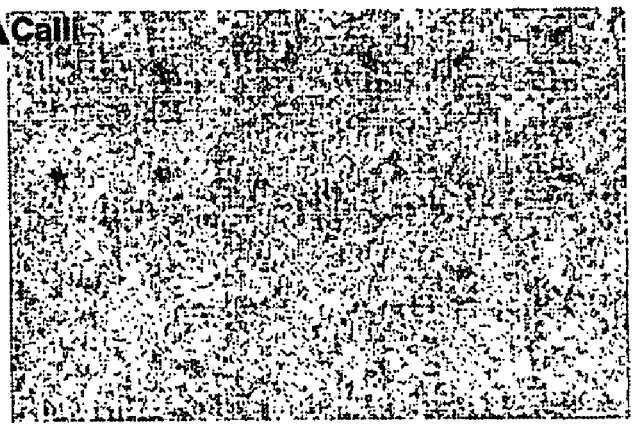
FIG. 18 shows the expression pattern of PRO 01 51 (WSI18, SEQ ID NO 16). GUS staining is visible in the calli and upper plant parts (A) as well as in the aleurone layer and embryo (B).
Figure 18:
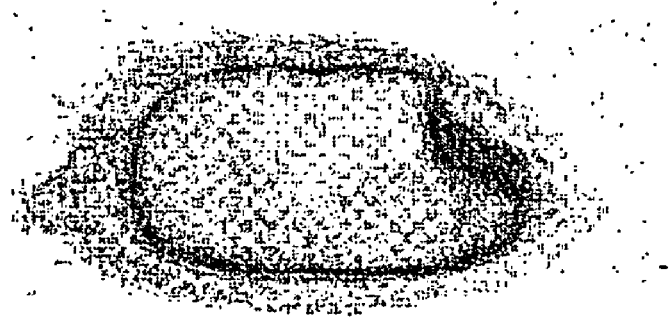
Figure 19:
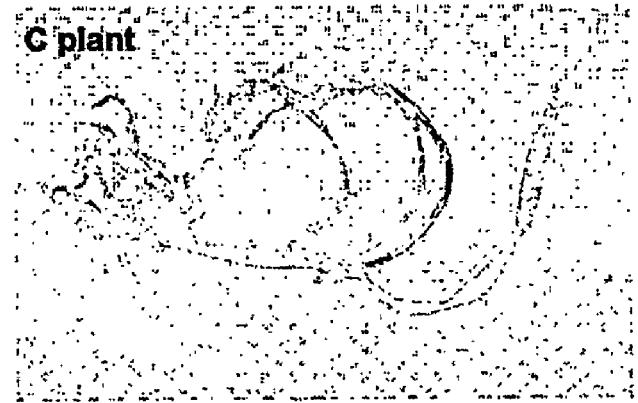
FIG. 19 shows the expression pattern of PRO0169 (aquaporine, SEQ ID NO 17). GUS staining is visible in the whole plant (constitutive expression).
Figure 20:
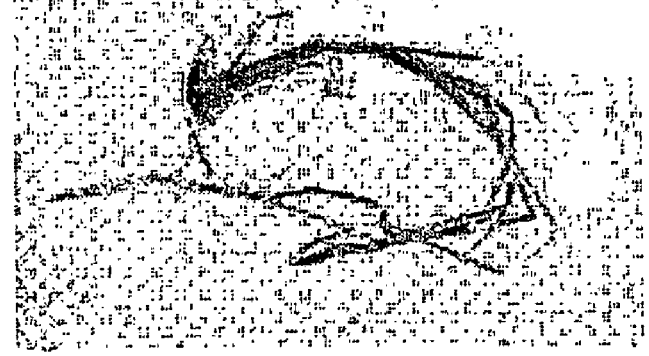
FIG. 20 shows the expression pattern of PRO0170 (High mobility group protein, SEQ ID NO 18). GUS staining is strongly visible in the whole plant as is illustrated by the "B plants" (A), and various tissues such as old leaves, young leaves and seeds (B) and calli (C) (constitutive expression).
Figure 20:
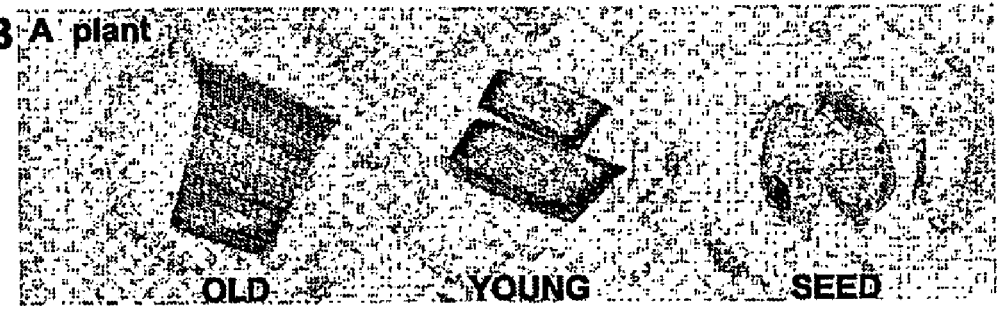
Figure 20:
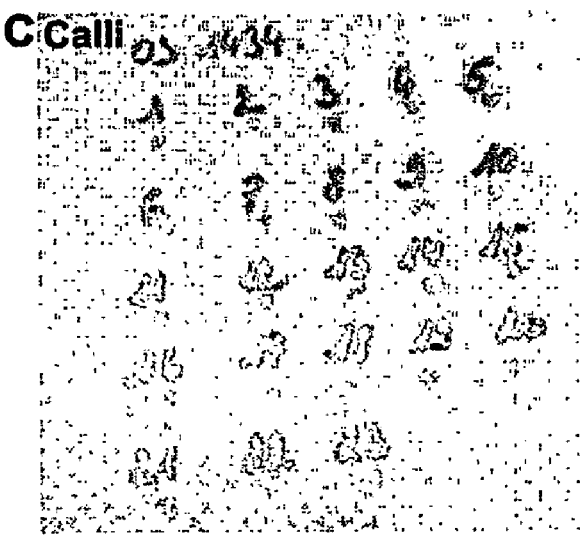
Figure 21:
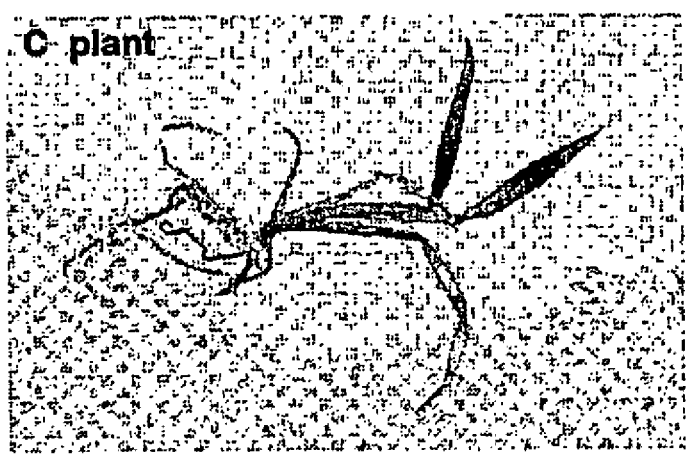
FIG. 21 shows the expression pattern of PRO0171 (reversibly glycosylated protein RGP1, SEQ ID NO 19). GUS staining is visible in all plant parts (constitutive expression).
Figure 22:
FIG. 22 shows the expression pattern of PRO0173 (cytosolic MDH, SEQ ID NO 20). GUS staining is visible in all plant parts and particularly in the shoot (above-ground tissues) and seeds.
Figure 23:
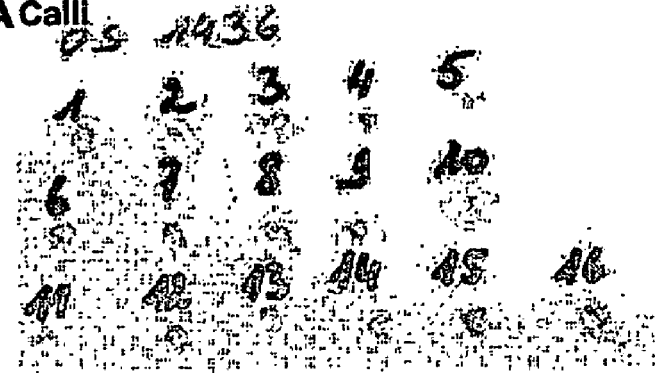
FIG. 23 shows the expression pattern of PRO0175 (RAB21, SEQ ID NO 21). GUS staining is weakly visible in calli (A), meristems and young leaves, and is strongly visible in developing and maturing seeds (B) more particularly in the embryo.
Figure 23:
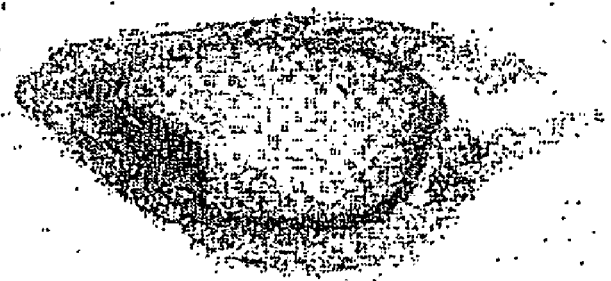
Figure 24:
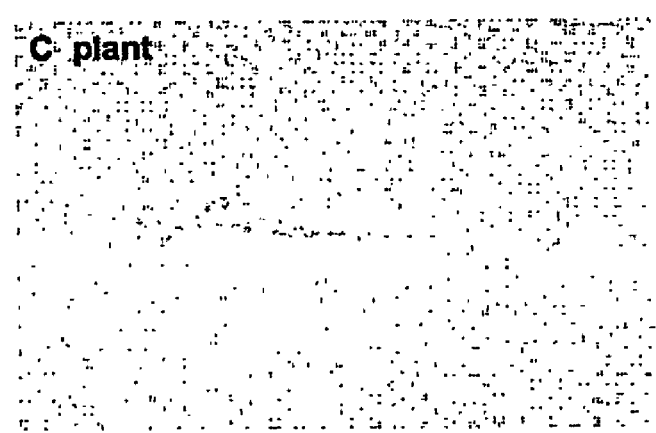
FIG. 24 shows the expression pattern of PRO0177 (Cdc2-1, SEQ ID NO 22). GUS staining is weakly visible in meristem and in leaf sheets.

In order to done each of the promoters of the present invention in front of a reporter gene, each entry done of Example 1 was subsequently used in an "LR recombination reaction" (Gateway™) with the destination vector p4581. This destination vector was designed to operably link each promoter of the present invention to the *Escherichia coli* beta-glucuronidase (GUS) gene via the substitution of the Gateway recombination cassette in front of the GUS gene. Furthermore this destination vector is suitable for transformation of plants and comprises within the T-DNA left and right borders the resulting promoter-GUS cassette and selectable marker and screenable marker cassettes (see FIG. 2). The resulting reporter vectors, comprising a promoter of the present invention operably linked to GUS, are subsequently transformed into *Agrobacterium* strain LBA4044 and subsequently into rice plants using standard transformation techniques.

Example 3

Expression Patterns of the Promoter-Gus Reporter Cassette in Plants Growth and Harvest of Transgenic Plants or Plant Parts at Various Stages (C Plants, B Plants and A Plants)

For each promoter-GUS reporter construct 3 T0 transgenic rice plants were generated from transformed cells. Plant growth was performed under normal conditions. The first transgenic plant was sacrificed for GUS staining when it had reached a size of about 5 cm, which plant is named herein "C plant". The second transgenic plant was sacrificed for GUS staining when it had reached a size of about 10 cm, which plant is named herein "B plant". The third transgenic plant was kept for seed production and is named herein "A plant". GUS staining was performed on complete C and B plants. On A plants, GUS staining was performed on leaf pieces, flowers and section of seeds at various developmental stages. A plants were allowed to set seed, which seeds were used after harvest for confirmation of the expression pattern in T1 plants.

GUS Staining

The sacrificed plants or plant parts were covered with 90% ice-cold acetone and incubated for 30 min at 4° C. After 3 washes of 5 min with Tris buffer [15.76 g Trizma HCl (Sigma T3253)+2,922 g NaCl in 1 Ibidi, adjusted to pH 7.0 with NaOH], the material was covered by a Tris/ferricyanate/X-Gluc solution [9,8 ml Tris buffer+0,2 ml ferricyanate stock (0.33 g Potassium ferricyanate (Sigma P3667) in 10 ml Tris buffer)+0,2 ml X-Gluc stock (26,1 mg X-Gluc (Europa bioproducts ML 113A) in 500 μl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

Expression Patterns of the Promoters of the Present Invention

The expression patterns of the rice promoters of the present invention are summarized in table 3.

TABLE 3 expression patterns of the rice promoters of the present invention

| PRO SEQ ID NO | Promoter number | Promoter name | Expression pattern |
|---|---|---|---|
| 1 | PRO0110 | RCc3 | strong root |
| 2 | PRO0005 | putative beta-amylase | Embryo (scutellum) |
| 3 | PRO0009 | putative cellulose synthase | weak in roots |
| 4 | PRO0058 | proteinase inhibitor Rgpi9 | seed |
| 5 | PRO0061 | beta expansine EXPB9 | weak in young tissues |
| 6 | PRO0063 | structural protein | young tissues + calli + embryo |
| 7 | PRO0081 | putative caffeoyl-CoA 3-O-methyltransferase | shoot |
| 8 | PRO0091 | prolamine RP5 | meristem + strong in endosperm |
| 9 | PRO0095 | putative methionine aminopeptidase | embryo |
| 10 | PRO0111 | uclacyanin 3-like protein | weak meristem |
| 11 | PRO0116 | 26S proteasome reg. particle non-ATPase s.u. 11 | weak meristem |
| 12 | PRO0117 | putative 40S ribosomal protein | weak in endosperm |
| 13 | PRO0122 | chlorophyll a/b-binding protein presursor (Cab27) | weak in shoot |
| 14 | PRO0123 | putative protochlorophyllide reductase | strong shoot specific |
| 15 | PRO0133 | chitinase Cht-3 | weak meristem specific |
| 16 | PRO0151 | WSI18 | Calli + shoot + strong embryo |
| 17 | PRO0169 | aquaporine | medium constitutive |
| 18 | PRO0170 | High mobility group protein | strong constitutive |
| 19 | PRO0171 | reversibly glycosylated protein RGP1 | weak constitutive |
| 20 | PRO0173 | cytosolic MDH | Shoot and seed |
| 21 | PRO0175 | RAB21 | embryo |
| 22 | PRO0177 | Cdc2-1 | weak in meristem + strong seed |

The following paragraphs describe the observed expression patterns of the promoters of the present invention in more detail. The observations are based on the visual inspection of the GUS stained tissues as described above. It is to be understood that for some promoters expression may be weak and that expression in certain tissues may only be visible with very sensitive detection methods.

PRO0110—SEQ ID NO 1—RCc3

1 construct (OS1432), which is a reporter vector as described in Example 2 comprising PRO0110 was investigated. 25 calli, 14 C, 21 B plants and 21 A plants were analysed. There was no expression visible in calli, but strong expression in roots of C plants (93%) and of B plants (81%) was observed. No expression in the shoots of A plants was observed. Therefore the RCc3 promoter PRO0110 is suitable for strong expression in root s.

PRO0005—SEQ ID NO 2—Putative Beta-Amylase 1 construct (OS1365) was investigated. 28 calli, 24 B plants and 22 A plants were analysed. Occasional expression in calli (7%) was observed as well as occasional weak expression in roots (4%) and shoots (12%) of B plants, expression in the scutellum of embryos of A plants (43%) and occasional expression in leaves (5%) of A plants. This promoter is therefore suitable for expression in embryo, more preferably in the scutellum of the embryo. This region of the embryo is also referred to as the transfer layer of the embryo. This promoter may have some leakiness in other tissues.

PRO0009—SEQ ID NO 3—Putative Cellulose Synthase 1 construct (OS1461) was investigated. 20 calli, 20 C, 20 B plants and 20 A plants were analysed. Occasional expression in calli (20%) was observed as well as weak expression in roots (55%) of C plants, occasional expression in young leaves (10%) of C plants and weak expression in the roots (25%) of B plants. No expression in leaves of A or B plants was observed. Therefore this promoter is suitable for expression in roots. This promoter may show some leakiness in the leaves.

PRO0058—SEQ ID NO 4—Proteinase Inhibitor Rgpi9

1 construct (OS1370) was investigated. 13 B plants and 12 A plants were analysed. No expression was observed in B plants. In A plants, no expression was observed in the leaves, but there was strong expression in endosperm and embryo (58-42%). Therefore, this promoter PRO0058 is suitable for expression in seeds.

PRO0061—-SEQ ID NO 5—Beta Expansine EXPB9

2 constructs (OS1441 and OS1460) were investigated. 20 calli, 32 C, 32 B plants and 32 A plants were analysed. Weak expression was observed in the leaves of C and B plants. In A plants expression in the flowers was observed (44%), more particularly in lemma of young spikelets. It was concluded that the promoter PRO0061 is suitable for expression in young tissue, more preferably in young, developing or expanding tissue, more preferably in green tissue.

PRO0063—SEQ ID NO 6—Putative Structural Protein 1 construct (OS1446) was investigated. 13 calli, 13 C, 13 B plants and 12 A plants were analysed. In calli, weak expression was detected (92%). In C plants, there was no expression in roots and there was weak expression in some leaves (46%). In B plants, there was no expression in roots and weak expression in young tillers (78%) or young leaves (54%), but no expression in old leaves. In A plants, there was occasional expression in young leaves (17%) and expression in embryo and scutellum (42%). Therefore it was concluded that this promoter is active in the above-ground tissues, such as leaf, stem and seed. These data demonstrate that the promoter is suitable for expression in calli and in the shoot, and for expression in young tissues and seeds.

PRO0081—SEQ ID NO 7—Putative Caffeoyl-CoA 3-Methyltransferase 1 construct (OS1419) was investigated. 20 calli, 20 C, 20 B plants and 20 A plants were analysed. No expression was observed in Calli. Expression was observed in C plants, more particularly weak expression in root cylinder (40%) and weak expression in young leaves (80%) and in old leaves. Expression was also observed in B plants, more particularly weak expression in roots (25%) and weak expression in young leaves (80%). Expression was also observed in young leaves (50%) of A plants. It was concluded that promoter PRO0081 is suitable for expression in above-ground tissues, preferably in the shoot. This promoter may have some leakage of expression in roots.

PRO0091—SEQ ID NO 8—Prolamine RP5

1 construct (OS1558) was investigated. 12 C, 12 B plants and 12 A plants were analysed. Weak expression was observed in the discrimination centre (50%) of C plants and in the discrimination centre (58%) of B plants. Strong expression was observed in endosperm (55%) of A plants. This promoter was found to be useful for strong expression in the endosperm, with leakiness in meristem, preferably the shoot meristem or discrimination centre.

PRO0095—SEQ ID NO 9—Putative Methionine Aminopeptidase 1 construct (OS1423) was investigated. 16 calli, 14 C, 14 B plants and 16 A plants were analysed. Some expression was observed in root-ips (36%) of C plants and in the embryo (38%) of A plants, but not in endosperm of A plants. It was concluded that PRO0095 is suitable for expression in embryo.

PRO0111—SEQ ID NO 10—Uclacyanin 3-Like Protein 1 construct (OS1421) was investigated. 22 calli, 21 C, 22 B plants and 21 A plants were analysed. Weak expression was observed in the discrimination centre and meristems (77%) of B plants. It was concluded that promoter PRO0111 is suitable for weak expression in the meristem, preferably in shoot meristem or discrimination centre.

PRO0116—SEQ ID NO 11-26S Proteasome Regulatory Particle Non-ATPase Subunit 11

1 construct (OS1679) was investigated. 13 C, 14 B plants and A plants were analysed. Weak expression was observed in meristem/discrimination centre of C plants (38%) and of B plants (71%) and in young leaf sheaths of C plants (77%) and of B plants (21%). It was concluded that promoter PRO0116 is suitable for expression in meristem, preferably in shoot meristem or discrimination centre.

PRO0117—SEQ ID NO 12—Putative 40S Ribosomal Protein 1 construct (OS1425) was investigated. 9 calli, 9 C, 9 B plants and 9 A plants were analysed. Occasional weak expression was observed in roots (22%) and in young leaf blades (44%) of C plants. Expression was mainly observed in endosperm (37%) of A plants. Therefore, promoter PRO117 was found to be suitable for expression in endosperm and may have some leakiness in young leaves.

PRO0122—SEQ ID NO 13—Chlorophyll a/b-Binding Protein Presursor (Cab27)

1 construct (OS1675) was investigated. 38 calli, 38 C, 38 B plants and 15 A plants were analysed. Very weak expression was observed in the discrimination centre and young leaf sheaths of C plants. It was concluded that this promoter PRO0122 is suitable for weak expression in shoots.

PRO0123—SEQ ID NO 14—Putative Protachlorophyllide Reductase 1 construct (OS1433) was investigated. 21 calli, 18 C, 19 B plants and 18 A plants were analysed. Strong expression was observed in shoots (33-68%) of C plants and B plants (63-79%). In B plants there was also occasional expression in roots. In A plants, again strong expression in young leaves (73%) was observed, as well as occasional expression in old leaves (39%). It was concluded that this promoter is suitable for strong expression in shoots, preferably in leaves.

PRO0133—SEQ ID NO 15—Chitinase Cht-3

1 construct (OS1687) was investigated. 15 call, 12 C, 16 B plants and 12A plants were analysed. Weak expression was observed in calli (66%) and in the discrimination centre/meristem (50%) of B plants. It was concluded that promoter PRO0133 is suitable for weak expression in meristem, preferably in shoot meristem or discrimination centre.

PRO0151—SEQ ID NO 16—WSI18

1 construct (OS1458) was investigated. 22 calli, 16 C, 16 B plants and 13 A plants were analysed. Strong expression was observed in calli (91%) and weak expression in shoot a of C plants (62%). In A plants there was very strong expression in the aleurone layer and in the embryo (46%). It was concluded that promoter PRO0151 is suitable for strong expression in calli and in seeds, more particularly in the aleurone layer and in the embryo of the seeds.

PRO0169—SEQ ID NO 17—Aquaporine 1 construct (OS1911) was investigated 11 calli, 100 C plants, B plants and A plants were analysed. Some expression (55%) was observed in calli and in roots (30%) of C plants. Furthermore, good expression was observed in shoot tissues (80%) of C plants and in young leaves of B plants. It was concluded that this promoter is suitable for constitutive expression, preferably constitutive in young plants.

PR0170—SEQ ID NO 18—High Mobility Group Protein 1 construct (OS1434) was investigated. 23 calli, 21 C, 21 B plants and 14 A plants were analysed. Expression was observed in calli (52%) and in roots (51%) of C plants. Moreover, strong expression was observed in young leaves (81%) of C plants. In roots (86%) of B plants and in young leaves (86%) of B plants. In A plants there was strong expression in young leaves (75%), old leaves (43%), embryo and aleurone but a weaker expression in endosperm (82%). It was concluded that promoter PRO170 is suitable for strong constitutive expression.

PRO0171—SEQ ID NO 19—Reversibly Glycosylated Protein RGP1

1 construct (OS1762) was investigated. 18 calli, 11 C and 13 B plants were analysed. Strong expression was observed in calli (44%) and in all issues (27%) of C plants. In all tissues of B plants (16%), expression was somewhat weaker but most pronounced the in discrimination centres (46%). It was concluded that promoter PRO0171 is suitable for constitutive expression.

PRO0173—SEQ ID NO 20—Cytosolic MDH 1 construct (OS1435) was investigated. 17 calli, 17 C, 17 B plants and 15 A plants were analysed. Occasional expression (12%) was observed in calli and weak expression was observed in upper parts (24-69%) of C plants as well as in young leaves (41%) of B plants. In A plants, expression in leaves (33%) was observed and strong expression in seeds (38%), but not in the root. It was concluded that the promoter PRO0173 is suitable for expression in above-ground tissues especially for constitutive expression in the shoot and especially in the seeds.

PRO0175—SEQ ID NO 21—RAB21

1 construct (OS1436) was investigated. 16 calli, 12 C 15 B plants and 15A plants were analysed. Expression was observed in some calli (31%), in the discrimination centres (42%) of C plants and in young leaves (25-58%) of C plants and A plants (15%). Furthermore, very strong expression was observed in aleurone and embryo (60%) of a plant. It was concluded that promoter PRO0175 is suitable for strong expression in calli and in seeds, more particularly in developing/maturing seeds, more particularly in the aleurone layer and in the embryo of the seeds.

PRO0177—SEQ ID NO 22—Cdc241

1 construct (OS1436) was investigated. 16 calli, 12 C, 15 B plants and 1 A plants were analysed. Expression was observed in some of the calli (31%). In the discrimination centre (42%) of C plants, in young leaves (25-68%) of C plants and occasionally in young leaves (15%) of A plants. Moreover, very strong expression was observed in aleurone and embryo (60%) of seeds from A plants. It was concluded that this promoter is suitable for specific expression in seeds, more particularly in developing/maturing seeds.

Example 4

Stability of the Expression Patterns of the Promoters of the Present Invention in Further Generations The above-mentioned analyses were performed on T0 plants originating from the transformed tissues. The stability of promoter activity in the next generations or progeny plants of the original T0 plant the so-called T1 and T2 plants, was evaluated as follows. The T0 plant transformed with the reporter constructs as mentioned in the above paragraphs of Example 2, were grown until maturity (A plants), of which the seeds (T1 seeds) were harvested and sown to generate progeny T1 plants. These plants were analysed as described above in Example 3 and the A T1 plants were allowed to reach maturity and to set T2 seeds.

The expression pattern of the promoters of the present invention was studied in T0 plants, T1 seeds, T1 plants and T2 seeds and in all the tissues (including seeds and seed tissues) as described in Example 3. The specific expression patterns as reported from the T0 and T1 seeds and described in Example 3 were confirmed in the following T1 generation and T2 seeds. It is concluded that the expression pattern of the promoters of the present are stably inherited in plants of subsequent generations.

Example 5

Stability of Expression Patterns of the Promoters of the Present Invention in Other Plants The above-mentioned plant analyses were performed on rice plants. This choice was based on the practical consideration that plant genetic engineering is most profitable for crop plants. Also in other crop plants, such as for example *Zea Mays*, the reporter constructs comprising the promoters according to the present invention are introduced and transformed plant are evaluated as described hereinabove. The expression patterns of the promoters according to the present invention are conserved among plants. Therefore, the promoters according to the present invention are also suitable for driving and/or regulating expression of an operably linked nucleic acid in monocots, such as corn.

For many other purposes such as research and horticulture, (small) herbs are being genetically modified, which involves the use of promoters. Therefore the reporter constructs comprising the promoters according to the present invention are introduced into other plants species such as for example *Arabidopsis thaliana* and transformed plants are evaluated as described hereinabove. The expression patterns of the promoters according to the present invention are conserved among plants. Therefore, the promoters according to the present invention are also suitable for driving and/or regulating expression of an operably linked nucleic acid in other plant species such as for example dicots, such as *Arabidopsis*.

The invention claimed is:

1. A genetic construct comprising:
   (a) an isolated promoter capable of driving and/or regulating expression, comprising an isolated nucleic acid sequence comprising the sequence of SEQ ID NO 18; and
   (b) a heterologous nucleic acid sequence operably linked to said isolated promoter; and optionally
   (c) a 3' transcription terminator.

2. An expression cassette comprising a genetic construct as defined in claim 1.

3. A transformation vector comprising a genetic construct as defined in claim 1.

4. An expression vector comprising a genetic construct as defined in claim 1.

5. A host cell comprising an isolated promoter as defined in claim 1.

6. The host cell according to claim 5, selected from the group consisting of a bacteria, algae, fungi, yeast, plant, insect and animal host cell.

7. A transgenic plant cell comprising the genetic construct according to claim 1.

8. The transgenic plant cell according to claim 7, wherein said cell is a monocot plant cell.

9. The transgenic plant cell according to claim 7, wherein said cell is a dicot plant cell.

10. A transgenic plant comprising a transgenic plant cell as defined in claim 7.

11. A transgenic plant according to claim 10, wherein said plant is selected from the group consisting of rice, maize, wheat, barley, millet, oats, rye, sorghum, soybean, sunflower, canola. sugarcane, alfalfa, bean, pea, flax, lupinus, rapeseed, tobacco, tomato, potato, squash, papaya, poplar and cotton.

12. A plant part from a plant as defined in claim 11, wherein the plant part comprises the genetic construct.

13. A plant part as defined in claim 12, selected from the group consisting of a harvestable part, a propagule and a progeny of the plant, wherein the plant part comprises the genetic construct.

14. A method for driving and/or regulating expression of a nucleic acid in a plant or plant cell, comprising introducing the genetic construct of claim 1 into a plant or plant cell.

15. The method according to claim 14, wherein said expression is constitutive.

16. A method for the production of a transgenic plant, comprising:
   (a) introducing into a plant cell the genetic construct according to claim 1 and
   (b) cultivating said plant cell under conditions promoting plant growth.

17. A method for the production of a transgenic plant, comprising:
   (a) introducing into a plant cell an expression cassette as defined in claim 2; and
   (b) cultivating said plant cell under conditions promoting plant growth.

18. A method for the production of a transgenic plant, comprising:
   (a) introducing into a plant cell a transformation vector as defined in claim 3; and
   (b) cultivating said plant cell under conditions promoting plant growth.

19. A method for the production of a transgenic plant, comprising:
   (a) introducing into a plant cell an expression vector as defined in claim 4; and
   (b) cultivating said plant cell under conditions promoting plant growth.

* * * * *